United States Patent
Le Tiran et al.

(10) Patent No.: US 9,115,159 B2
(45) Date of Patent: Aug. 25, 2015

(54) PHOSPHATE COMPOUNDS, A PROCESS FOR THEIR PREPARATION AND PHARMACEUTICAL COMPOSITIONS CONTAINING THEM

(71) Applicants: LES LABORATOIRES SERVIER, Suresnes Cedex (FR); VERNALIS (R&D) Ltd., Berkshire (GB)

(72) Inventors: Arnaud Le Tiran, Croissy sur Seine (FR); Thierry Le Diguarher, Saint Denis de l'Hôtel (FR); Jérôme-Benoit Starck, Rueil-Malmaison (FR); Jean-Michel Henlin, Suresnes (FR); Anne-Françoise Guillouzic, Nanterre (FR); Guillaume De Nanteuil, Suresnes (FR); Olivier Geneste, Rueil-Malmaison (FR); James Edward Paul Davidson, Great Shelford (GB); James Brooke Murray, Linton (GB); I-Jen Chen, Cambridge (GB)

(73) Assignees: LES LABORATOIRES SERVIER, Suresnes Cedex (FR); VERNALIS (R&D) LTD, Winnersh (GB)

( * ) Notice: Subject to any disclaimer, the term of this patent is extended or adjusted under 35 U.S.C. 154(b) by 0 days.

(21) Appl. No.: 14/337,577

(22) Filed: Jul. 22, 2014

(65) Prior Publication Data
US 2015/0031648 A1 Jan. 29, 2015

(30) Foreign Application Priority Data
Jul. 23, 2013 (FR) ...................... 13 57259

(51) Int. Cl.
| | |
|---|---|
| *A61K 31/675* | (2006.01) |
| *C07F 9/6561* | (2006.01) |
| *C07F 9/09* | (2006.01) |
| *A61K 45/06* | (2006.01) |
| *A61N 5/10* | (2006.01) |
| *C07F 9/6558* | (2006.01) |

(52) U.S. Cl.
CPC ............ *C07F 9/6561* (2013.01); *A61K 31/675* (2013.01); *A61K 45/06* (2013.01); *A61N 5/10* (2013.01); *C07F 9/09* (2013.01); *C07F 9/65583* (2013.01)

(58) Field of Classification Search
None
See application file for complete search history.

(56) References Cited

U.S. PATENT DOCUMENTS

| | | | |
|---|---|---|---|
| 7,713,994 | B2 | 5/2010 | Tsou et al. |
| 7,902,218 | B2 | 3/2011 | Thompson, III et al. |
| 8,263,607 | B2 | 9/2012 | Shishikura et al. |

FOREIGN PATENT DOCUMENTS

| | | |
|---|---|---|
| RU | 2468010 | 11/2012 |
| WO | WO 2012/162385 | 11/2012 |
| WO | WO 2013/096049 | 6/2013 |
| WO | WO 2013/096051 | 6/2013 |
| WO | WO 2013/096055 | 6/2013 |
| WO | WO 2013/096059 | 6/2013 |
| WO | WO 2013/098080 | 6/2013 |
| WO | WO 2013/110890 | 8/2013 |

OTHER PUBLICATIONS

International Search Report for PCT/FR2014/051887 dated Nov. 4, 2014.
Bundgaard, H., Textbook of Drug Design and Development, p. 113-191, 1991.
French Preliminary Search Report for FR1357259 of May 8, 2014.
Perez, H., et al., Bioorganic and Medicinal Chemistry Letters, vol. 22, No. 12, p. 3946-3950, May 2, 2012.
Porter, J., et al., Bioorganic and Medicinal Chemistry Letters, vol. 19, No. 1, p. 230-233, Oct. 31, 2008.
Porter, J., et al., Bioorganic and Medicinal Chemistry Letters, vol. 19, No. 6, p. 1767-1772, Mar. 15, 2009.

*Primary Examiner* — Zinna Northington Davis
(74) *Attorney, Agent, or Firm* — Hueschen and Sage

(57) ABSTRACT

Compounds of formula (I):

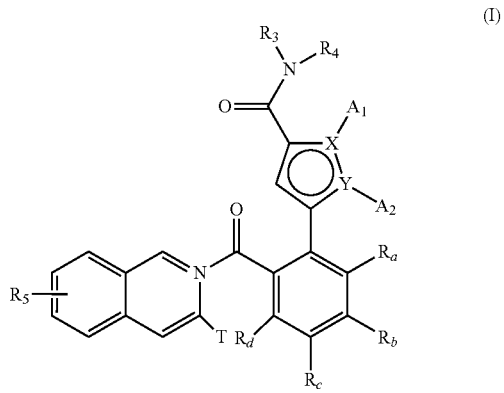

wherein X, Y, $A_1$, $A_2$, $R_a$, $R_b$, $R_c$, $R_d$, $R_3$, $R_4$, T and $R_5$ are as defined in the description.
Medicinal products containing the same which are useful in treating pathologies involving a deficit in apoptosis, such as cancer, auto-immune diseases, and diseases of the immune system.

15 Claims, No Drawings

PHOSPHATE COMPOUNDS, A PROCESS FOR THEIR PREPARATION AND PHARMACEUTICAL COMPOSITIONS CONTAINING THEM

The present invention relates to new phosphate compounds, to a process for their preparation and to pharmaceutical compositions containing them.

The compounds of the present invention are new and have very valuable pharmacological and pharmacokinetic characteristics for use in the field of apoptosis and cancerology.

Apoptosis, or programmed cell death, is a physiological process that is crucial for embryonic development and maintenance of tissue homeostasis.

Apoptotic-type cell death involves morphological changes such as condensation of the nucleus, DNA fragmentation and also biochemical phenomena such as the activation of caspases which cause damage to key structural components of the cell, so inducing its disassembly and death. Regulation of the process of apoptosis is complex and involves the activation or repression of several intracellular signalling pathways (Cory S. et al., Nature Review Cancer, 2002, 2, 647-656).

Deregulation of apoptosis is involved in certain pathologies. Increased apoptosis is associated with neurodegenerative diseases such as Parkinson's disease, Alzheimer's disease and ischaemia. Conversely, deficits in the implementation of apoptosis play a significant role in the development of cancers and their chemoresistance, in auto-immune diseases, inflammatory diseases and viral infections. Accordingly, absence of apoptosis is one of the phenotypic signatures of cancer (Hanahan D. et al., Cell 2000, 100, 57-70).

The anti-apoptotic proteins of the Bcl-2 family are associated with numerous pathologies. The involvement of proteins of the Bcl-2 family is described in numerous types of cancer, such as colorectal cancer, breast cancer, small-cell lung cancer, non-small-cell lung cancer, bladder cancer, ovarian cancer, prostate cancer, chronic lymphoid leukaemia, follicular lymphoma, myeloma, etc. Overexpression of the anti-apoptotic proteins of the Bcl-2 family is involved in tumorigenesis, in resistance to chemotherapy and in the clinical prognosis of patients affected by cancer. There is, therefore, a therapeutic need for compounds that inhibit the anti-apoptotic activity of the proteins of the Bcl-2 family.

In addition to being new, the compounds of the present invention have pharmacological and pharmacokinetic properties making it possible to use them in pathologies involving a defect in apoptosis, such as, for example, in the treatment of cancer, auto-immune diseases and diseases of the immune system.

The present invention relates more especially to a phosphate compound of formula (I):

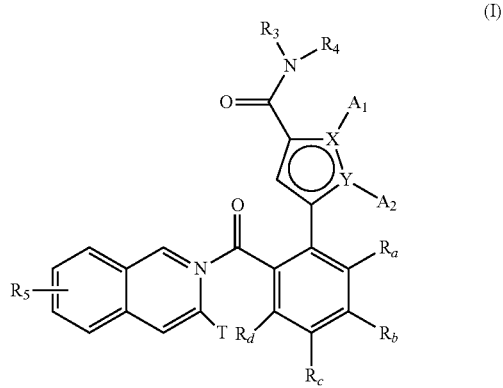

wherein:
X and Y represent a carbon atom or a nitrogen atom, it being understood that they may not simultaneously represent two carbons atoms or two nitrogen atoms,
$A_1$ and $A_2$, together with the atoms carrying them, form an optionally substituted, aromatic or non-aromatic heterocycle Het composed of 5, 6 or 7 ring members which may contain, in addition to the nitrogen represented by X or by Y, from one to 3 hetero atoms selected independently from oxygen, sulphur and nitrogen, it being understood that the nitrogen in question may be substituted by a group representing a hydrogen atom, a linear or branched $(C_1-C_6)$alkyl group or a group —C(O)—O-Alk wherein Alk is a linear or branched $(C_1-C_6)$alkyl group,
or $A_1$ and $A_2$ independently of one another represent a hydrogen atom, a linear or branched $(C_1-C_6)$polyhaloalkyl, a linear or branched $(C_1-C_6)$alkyl group or a cycloalkyl,
T represents a hydrogen atom, a linear or branched $(C_1-C_6)$alkyl group optionally substituted by from one to three halogen atoms, a group $(C_1-C_4)$alkyl-$NR_1R_2$, or a group $(C_1-C_4)$alkyl-$OR_6$,
$R_1$ and $R_2$ independently of one another represent a hydrogen atom or a linear or branched $(C_1-C_6)$alkyl group,
or $R_1$ and $R_2$ form with the nitrogen atom carrying them a heterocycloalkyl,
$R_3$ represents a linear or branched $(C_1-C_6)$alkyl group, a linear or branched $(C_2-C_6)$alkenyl group, a linear or branched $(C_2-C_6)$alkynyl group, a cycloalkyl group, a $(C_3-C_{10})$cycloalkyl-$(C_1-C_6)$alkyl group wherein the alkyl moiety is linear or branched, a heterocycloalkyl group, an aryl group or a heteroaryl group, it being understood that one or more of the carbon atoms of the preceding groups, or of their possible substituents, may be deuterated,
$R_4$ represents an aryl group, a heteroaryl group, a cycloalkyl group or a linear or branched $(C_1-C_6)$alkyl group, it being understood that one or more of the carbon atoms of the preceding groups, or of their possible substituents, may be deuterated,
$R_5$ represents a hydrogen or halogen atom, a linear or branched $(C_1-C_6)$alkyl group, or a linear or branched $(C_1-C_6)$alkoxy group,
$R_6$ represents a hydrogen atom or a linear or branched $(C_1-C_6)$alkyl group,
$R_a$, $R_b$, $R_c$ and $R_d$, each independently of the others, represent $R_7$, a halogen atom, a linear or branched $(C_1-C_6)$ alkoxy group, a hydroxy group, a linear or branched $(C_1-C_6)$polyhaloalkyl group, a trifluoromethoxy group, —$NR_7R_7'$, nitro, $R_7$—CO—$(C_0-C_6)$alkyl-, $R_7$—CO—NH—$(C_0-C_6)$alkyl-, $NR_7R_7'$—CO—$(C_0-C_6)$alkyl-, $NR_7R_7'$—CO—$(C_0-C_6)$alkyl-O—, $R_7$—$SO_2$—NH—$(C_0-C_6)$alkyl-, $R_7$—NH—CO—NH—$(C_0-C_6)$alkyl-, $R_7$—O—CO—NH—$(C_0-C_6)$alkyl-, a heterocycloalkyl group, or the substituents of one of the pairs $(R_a,R_b)$, $(R_b,R_c)$ or $(R_c,R_d)$ form together with the carbon atoms carrying them a ring composed of from 5 to 7 ring members, which may contain from one to 2 hetero atoms selected from oxygen and sulphur, it also being understood that one or more carbon atoms of the ring defined hereinbefore may be deuterated or substituted by from one to 3 groups selected from halogen and linear or branched $(C_1-C_6)$alkyl,
$R_7$ and $R_7'$ independently of one another represent a hydrogen, a linear or branched $(C_1-C_6)$alkyl, a linear or branched $(C_2-C_6)$alkenyl, a linear or branched $(C_2-C_6)$ alkynyl, an aryl or a heteroaryl, or $R_7$ and $R_7'$ together with nitrogen atom carrying them form a heterocycle composed of from 5 to 7 ring members, the compound of formula (I) being such that at least one of the carbon atoms contained in it is substituted by one of the following phosphate groups: —OPO(OM)(OM'), —OPO(OM)(O⁻M₁⁺), —OPO(O⁻M₁⁺)(O⁻M₂⁺), —OPO(O⁻)(O⁻)M₃²⁺, —OPO(OM)(O[CH₂CH₂O]ₙCH₃), or —OPO(O⁻M₁⁺)(O[CH₂CH₂O]ₙCH₃), wherein M and M' independently of one another represent a hydrogen atom, a linear or branched (C₁-C₆)alkyl group, a linear or branched (C₂-C₆)alkenyl group, a linear or branched (C₂-C₆)alkynyl group, a cycloalkyl or a heterocycloalkyl both composed of 5 or 6 ring members, while M₁⁺ and M₂⁺ independently of one another represent a pharmaceutically acceptable monovalent cation, and M₃²⁺ represents a pharmaceutically acceptable divalent cation and n is an integer from 1 to 5, it being understood that:
"aryl" means a phenyl, naphthyl, biphenyl or indenyl group,
"heteroaryl" means any mono- or bi-cyclic group composed of from 5 to 10 ring members, having at least one aromatic moiety and containing from 1 to 4 hetero atoms selected from oxygen, sulphur and nitrogen (including quaternary nitrogens),
"cycloalkyl" means any mono- or bi-cyclic, non-aromatic, carbocyclic group containing from 3 to 10 ring members,
"heterocycloalkyl" means any mono- or bi-cyclic, non-aromatic, condensed or spiro group composed of 3 to 10 ring members and containing from 1 to 3 hetero atoms selected from oxygen, sulphur, SO, SO₂ and nitrogen,
it being possible for the aryl, heteroaryl, cycloalkyl and heterocycloalkyl groups so defined and the groups alkyl, alkenyl, alkynyl and alkoxy to be substituted by from 1 to 3 groups selected from optionally substituted, linear or branched (C₁-C₆)alkyl, (C₃-C₆)spiro, linear or branched, optionally substituted (C₁-C₆)alkoxy, (C₁-C₆)alkyl-S—, hydroxy, oxo (or N-oxide where appropriate), nitro, cyano, —COOR', —OCOR', NR'R", linear or branched (C₁-C₆) polyhaloalkyl, trifluoromethoxy, (C₁-C₆)alkylsulphonyl, halogen, optionally substituted aryl, heteroaryl, aryloxy, arylthio, cycloalkyl, heterocycloalkyl optionally substituted by one or more halogen atoms or alkyl groups, it being understood that R' and R" independently of one another represent a hydrogen atom or an optionally substituted, linear or branched (C₁-C₆)alkyl group,
it being possible for the Het group defined in formula (I) to be substituted by from one to three groups selected from linear or branched (C₁-C₆)alkyl, hydroxy, linear or branched (C₁-C₆)alkoxy, NR₁'R₁" and halogen, it being understood that R₁' and R₁" are as defined for the groups R' and R" mentioned hereinbefore,
to its enantiomers and diastereoisomers, and to addition salts thereof with a pharmaceutically acceptable acid or base.

Among the pharmaceutically acceptable acids there may be mentioned, without implying any limitation, hydrochloric acid, hydrobromic acid, sulphuric acid, phosphonic acid, acetic acid, trifluoroacetic acid, lactic acid, pyruvic acid, malonic acid, succinic acid, glutaric acid, fumaric acid, tartaric acid, maleic acid, citric acid, ascorbic acid, oxalic acid, methanesulphonic acid, camphoric acid etc.

Among the pharmaceutically acceptable bases there may be mentioned, without implying any limitation, sodium hydroxide, potassium hydroxide, triethylamine, tert-butylamine etc.

Preferred compounds of the invention include compounds of formula (I) wherein R₄ represents phenyl substituted in the para position by a group of formula —OPO(OM)(OM'), —OPO(OM)(O⁻M₁⁺), —OPO(O⁻M₁⁺)(O⁻M₂⁺), —OPO(O)(O⁻)M₃²⁺, —OPO(OM)(O[CH₂CH₂O]ₙCH₃), or —OPO(O⁻M₁⁺)(O[CH₂CH₂O]ₙCH₃), wherein M and M' independently of one another represent a hydrogen atom, a linear or branched (C₁-C₆)alkyl group, a linear or branched (C₂-C₆) alkenyl group, a linear or branched (C₂-C₆)alkynyl group, a cycloalkyl or a heterocycloalkyl both composed of 5 or 6 ring members, while M₁⁺ and M₂⁺ independently of one another represent a pharmaceutically acceptable monovalent cation, and M₃²⁺ represents a pharmaceutically acceptable divalent cation and n is an integer from 1 to 5, it being understood that the phenyl group may optionally be substituted by one or more halogen atoms.

Preference is given to compounds of formula (I) wherein R₄ represents a phenyl or a pyrimidin-5-yl group, both substituted in the para position by a group of formula —OPO(O⁻M₁⁺)(O⁻M₂⁺), and even more especially by a group of formula —OPO(O⁻Na⁺)(O⁻Na⁺).

Advantageously, X represents a carbon atom and Y represents a nitrogen atom. Even more advantageously, the group:

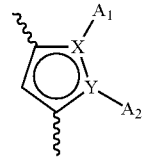

represents a 5,6,7,8-tetrahydroindolizine, an indolizine or a dimethylated pyrrole.

T preferably represents a methyl, (morpholin-4-yl)methyl or 3-(morpholin-4-yl)propyl group.

In preferred compounds of the invention, $R_a$ and $R_d$ each represent a hydrogen atom and ($R_b$,$R_c$), together with the carbon atoms carrying them, form a 1,3-dioxolane group or a 1,4-dioxane group; or $R_a$, $R_c$ and $R_d$ each represent a hydrogen atom and $R_b$ represents a hydrogen or a halogen.

In another embodiment of the invention, $R_a$ and $R_d$ each represent a hydrogen atom, $R_b$ represents a halogen atom and $R_c$ a methoxy group.

Alternatively, $R_a$, $R_b$ and $R_d$ each advantageously represent a hydrogen atom and $R_c$ represents a group NR₇R₇'—CO—(C₀-C₆)alkyl-O—, and even more preferably $R_c$ represents a 2-oxo-2-(piperidin-1-yl)ethoxy group.

Furthermore, $R_3$ advantageously represents a group selected from phenyl, 1H-indole, 1H-pyrrolo[2,3-b]pyridine, pyridine, 1H-pyrazole, 1H-pyrrole and 2,3-dihydro-1H-pyrrolo[2,3-b]pyridine, those groups optionally having one or more substituents selected from linear or branched (C₁-C₆) alkyl (more preferably methyl), cyano and trideuteriomethyl.

Among the preferred compounds of the invention there may be mentioned:
4-[{[3-(6-{[(3S)-3-(morpholin-4-ylmethyl)-3,4-dihydroisoquinolin-2(1H)-yl]carbonyl}-1,3-benzodioxol-5-yl)-5,6,7,8-tetrahydroindolizin-1-yl]carbonyl}(phenyl) amino]phenyl disodium phosphate,
4-[{[5-(5-chloro-2-{[(3S)-3-(morpholin-4-ylmethyl)-3,4-dihydroisoquinolin-2(1H)-yl]carbonyl}phenyl)-1,2-dimethyl-1H-pyrrol-3-yl]carbonyl}(pyridin-4-yl) amino]phenyl disodium phosphate,
4-({[5-(5-chloro-2-{[(3S)-3-(morpholin-4-ylmethyl)-3,4-dihydroisoquinolin-2(1H)-yl]carbonyl}phenyl)-1,2-dimethyl-1H-pyrrol-3-yl]carbonyl}[1-(trideuteriomethyl)-1H-pyrazol-4-yl]amino)phenyl disodium phosphate, 4-[{[5-(5-chloro-2-{[(3S)-3-(morpholin-4-ylmethyl)-3,4-dihydroisoquinolin-2(1H)-yl]carbonyl}phenyl)-1,2-dimethyl-1H-pyrrol-3-yl]carbonyl}(5-cyano-1,2-dimethyl-1H-pyrrol-3-yl)amino]phenyl disodium phosphate, 4-[{[5-(5-chloro-2-{[(3S)-3-(morpholin-4-ylmethyl)-3,4-dihydroisoquinolin-2(1H)-yl]carbonyl}phenyl)-1,2-dimethyl-1H-pyrrol-3-yl]carbonyl}(5-cyano-1-methyl-1H-pyrrol-3-yl)amino]phenyl disodium phosphate, 4-[{[5-(5-chloro-2-{[(3S)-3-(morpholin-4-ylmethyl)-3,4-dihydroisoquinolin-2(1H)-yl]carbonyl}phenyl)-1,2-dimethyl-1H-pyrrol-3-yl]carbonyl}(1-methyl-1H-pyrazol-4-yl)amino]phenyl disodium phosphate, 4-[(5-cyano-1,2-dimethyl-1H-pyrrol-3-yl) {[5-(5-fluoro-2-{[(3S)-3-(morpholin-4-ylmethyl)-3,4-dihydroisoquinolin-2(1H)-yl]carbonyl}phenyl)-1,2-dimethyl-1H-pyrrol-3-yl]carbonyl}amino]phenyl disodium phosphate, 4-[{[5-(5-fluoro-2-{[(3S)-3-(morpholin-4-ylmethyl)-3,4-dihydroisoquinolin-2(1H)-yl]carbonyl}phenyl)-1,2-dimethyl-1H-pyrrol-3-yl]carbonyl}(1-methyl-1H-pyrazol-4-yl)amino]phenyl disodium phosphate, their enantiomers and diastereoisomers, and addition salts thereof with a pharmaceutically acceptable acid or base.

Pharmacokinetic study of the phosphate compounds of formula (I) showed that they were converted in vivo into compounds of formula (I') characterised in that the phosphate function was metabolised into a hydroxy function. The compounds of formula (I) accordingly behave as prodrugs of compounds of formula (I') having the following formula:

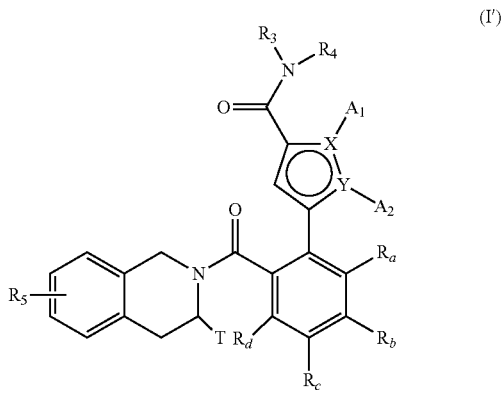

wherein:
X and Y represent a carbon atom or a nitrogen atom, it being understood that they may not simultaneously represent two carbons atoms or two nitrogen atoms, $A_1$ and $A_2$, together with the atoms carrying them, form an optionally substituted, aromatic or non-aromatic heterocycle Het composed of 5, 6 or 7 ring members which may contain, in addition to the nitrogen represented by X or by Y, from one to 3 hetero atoms selected independently from oxygen, sulphur and nitrogen, it being understood that the nitrogen in question may be substituted by a group representing a hydrogen atom, a linear or branched ($C_1$-$C_6$)alkyl group or a group —C(O)—O-Alk wherein Alk is a linear or branched ($C_1$-$C_6$)alkyl group, or $A_1$ and $A_2$ independently of one another represent a hydrogen atom, a linear or branched ($C_1$-$C_6$) polyhaloalkyl, a linear or branched ($C_1$-$C_6$)alkyl group or a cycloalkyl, T represents a hydrogen atom, a linear or branched ($C_1$-$C_6$)alkyl group optionally substituted by from one to three halogen atoms, a group ($C_1$-$C_4$)alkyl-$NR_1R_2$, or a group ($C_1$-$C_4$)alkyl-$OR_6$, $R_1$ and $R_2$ independently of one another represent a hydrogen atom or a linear or branched ($C_1$-$C_6$)alkyl group,
or $R_1$ and $R_2$ form with the nitrogen atom carrying them a heterocycloalkyl, $R_3$ represents a linear or branched ($C_1$-$C_6$)alkyl group, a linear or branched ($C_2$-$C_6$)alkenyl group, a linear or branched ($C_2$-$C_6$)alkynyl group, a cycloalkyl group, a ($C_3$-$C_{10}$)cycloalkyl-($C_1$-$C_6$)alkyl group wherein the alkyl moiety is linear or branched, a heterocycloalkyl group, an aryl group or a heteroaryl group, it being understood that one or more of the carbon atoms of the preceding groups, or of their possible substituents, may be deuterated, $R_4$ represents an aryl group, a heteroaryl group, a cycloalkyl group or a linear or branched ($C_1$-$C_6$)alkyl group, it being understood that one or more of the carbon atoms of the preceding groups, or of their possible substituents, may be deuterated, $R_5$ represents a hydrogen or halogen atom, a linear or branched ($C_1$-$C_6$)alkyl group, or a linear or branched ($C_1$-$C_6$)alkoxy group, $R_6$ represents a hydrogen atom or a linear or branched ($C_1$-$C_6$)alkyl group, $R_a$, $R_b$, $R_c$ and $R_d$, each independently of the others, represent $R_7$, a halogen atom, a linear or branched ($C_1$-$C_6$) alkoxy group, a hydroxy group, a linear or branched ($C_1$-$C_6$)polyhaloalkyl group, a trifluoromethoxy group, —$NR_7R_7'$, nitro, $R_7$—CO—($C_0$-$C_6$)alkyl-, $R_7$—CO—NH—($C_0$-$C_6$)alkyl-, $NR_7R_7'$—CO—($C_0$-$C_6$)alkyl-, $NR_7R_7'$—CO—($C_0$-$C_6$)alkyl-O—, $R_7$—$SO_2$—NH—($C_0$-$C_6$)alkyl-, $R_7$—NH—CO—NH—($C_0$-$C_6$)alkyl-, $R_7$—O—CO—NH—($C_0$-$C_6$)alkyl-, a heterocycloalkyl group, or the substituents of one of the pairs ($R_a$,$R_b$), ($R_b$,$R_c$) or ($R_c$,$R_d$) form together with the carbon atoms carrying them a ring composed of from 5 to 7 ring members, which may contain from one to 2 hetero atoms selected from oxygen and sulphur, it also being understood that one or more carbon atoms of the ring defined hereinbefore may be deuterated or substituted by from one to 3 groups selected from halogen and linear or branched ($C_1$-$C_6$)alkyl, $R_7$ and $R_7'$ independently of one another represent a hydrogen, a linear or branched ($C_1$-$C_6$)alkyl, a linear or branched ($C_2$-$C_6$)alkenyl, a linear or branched ($C_2$-$C_6$) alkynyl, an aryl or a heteroaryl, or $R_7$ and $R_7'$ together with nitrogen atom carrying them form a heterocycle composed of from 5 to 7 ring members, it being understood that:
"aryl" means a phenyl, naphthyl, biphenyl or indenyl group,
"heteroaryl" means any mono- or bi-cyclic group composed of from 5 to 10 ring members, having at least one aromatic moiety and containing from 1 to 4 hetero atoms selected from oxygen, sulphur and nitrogen (including quaternary nitrogens),
"cycloalkyl" means any mono- or bi-cyclic, non-aromatic, carbocyclic group containing from 3 to 10 ring members,
"heterocycloalkyl" means any mono- or bi-cyclic, non-aromatic, condensed or spiro group composed of 3 to 10 ring members and containing from 1 to 3 hetero atoms selected from oxygen, sulphur, SO, $SO_2$ and nitrogen, it being possible for the aryl, heteroaryl, cycloalkyl and heterocycloalkyl groups so defined and the groups alkyl, alkenyl, alkynyl and alkoxy to be substituted by from 1 to 3 groups selected from optionally substituted, linear or branched $(C_1-C_6)$alkyl, $(C_3-C_6)$spiro, linear or branched, optionally substituted $(C_1-C_6)$alkoxy, $(C_1-C_6)$alkyl-S—, hydroxy, oxo (or N-oxide where appropriate), nitro, cyano, —COOR', —OCOR', NR'R", linear or branched $(C_1-C_6)$ polyhaloalkyl, trifluoromethoxy, $(C_1-C_6)$alkylsulphonyl, halogen, optionally substituted aryl, heteroaryl, aryloxy, arylthio, cycloalkyl, heterocycloalkyl optionally substituted by one or more halogen atoms or alkyl groups, it being understood that R' and R" independently of one another represent a hydrogen atom or an optionally substituted, linear or branched $(C_1-C_6)$alkyl group, it being possible for the Het group defined in formula (I') to be substituted by from one to three groups selected from linear or branched $(C_1-C_6)$alkyl, hydroxy, linear or branched $(C_1-C_6)$alkoxy, $NR_1'R_1''$ and halogen, it being understood that $R_1'$ and $R_1''$ are as defined for the groups R' and R" mentioned hereinbefore, their enantiomers and diastereoisomers, and addition salts thereof with a pharmaceutically acceptable acid or base.

The compounds of formula (I') have pro-apoptotic properties and as a result are of major therapeutic value in the treatment of cancers, auto-immune diseases and diseases of the immune system. In the present invention it has been shown that, by administering the phosphate compounds of formula (I), the in vivo exposure to the compounds of formula (I') was optimised. The solubility of the compounds of formula (I) is in fact much greater than that of the compounds of formula (I'). Consequently, using the compounds of formula (I) in the manufacture of pharmaceutical compositions is especially advantageous from the galenic point of view.

The invention relates also to a process for the preparation of compounds of formula (I), which process is characterised in that there is used as starting material the compound of formula (II):

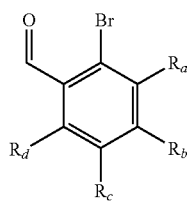

(II)

wherein $R_a$, $R_b$, $R_c$ and $R_d$ are as defined for formula (I'), which compound of formula (II) is subjected to a Heck reaction, in an aqueous or organic medium, in the presence of a palladium catalyst, of a base, of a phosphine and of the compound of formula (III):

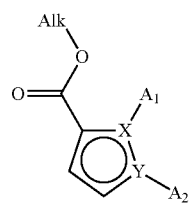

(III)

wherein the groups $A_1$, $A_2$, X and Y are as defined for formula (I') and Alk represents a linear or branched $(C_1-C_6)$alkyl, to obtain the compound of formula (IV):

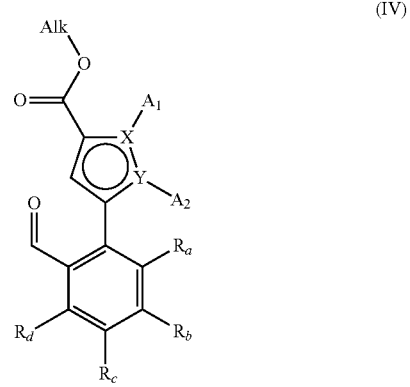

(IV)

wherein $A_1$, $A_2$, X, Y, $R_a$, $R_b$, $R_c$ and $R_d$ are as defined for formula (I') and Alk is as defined hereinbefore, the aldehyde function of which compound of formula (IV) is oxidised to a carboxylic acid to form the compound of formula (V):

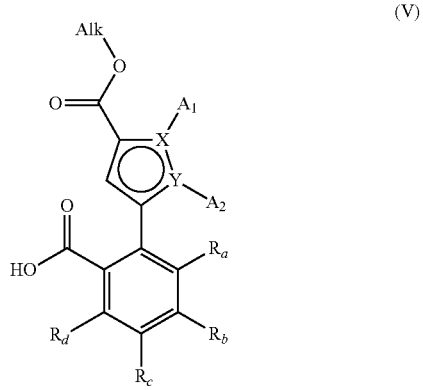

(V)

wherein $A_1$, $A_2$, X, Y, $R_a$, $R_b$, $R_c$ and $R_d$ are as defined for formula (I') and Alk is as defined hereinbefore, which compound of formula (V) is then subjected to peptide coupling with a compound of formula (VI):

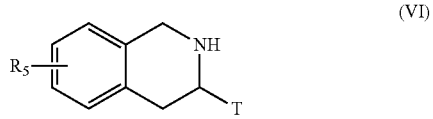

(VI)

wherein T and $R_5$ are as defined for formula (I'), to yield the compound of formula (VII):

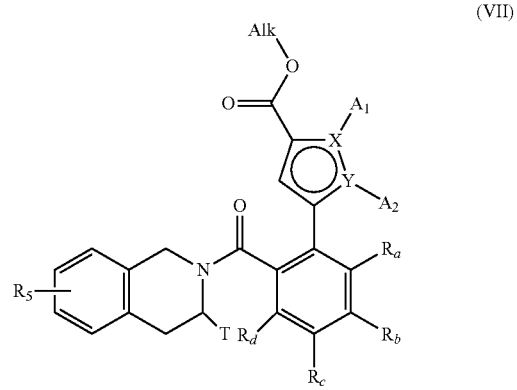

(VII)

wherein $A_1$, $A_2$, X, Y, $R_a$, $R_b$, $R_c$, $R_d$, T and $R_5$ are as defined for formula (I') and Alk is as defined hereinbefore, the ester function of which compound of formula (VII) is hydrolysed to yield the corresponding carboxylic acid or carboxylate, which may be converted into an acid derivative such as the corresponding acyl chloride or anhydride before being coupled with an amine $NHR_3R_4$ wherein $R_3$ and $R_4$ have the same meanings as for formula (I'), before being subjected to the action of a pyrophosphate, phosphonate or phosphoryl compound under basic conditions, it being possible for the compound thereby obtained to be optionally hydrolysed or hydrogenolysed to yield the compound of formula (I), which compound of formula (I) may be purified according to a conventional separation technique, which is converted, if desired, into its addition salts with a pharmaceutically acceptable acid or base and which is optionally separated into its isomers according to a conventional separation technique, it being understood that, at any time considered appropriate in the course of the above-described process, certain groups (hydroxy, amino . . . ) of the reagents or intermediates of synthesis may be protected and then deprotected according to the requirements of synthesis.

The compounds of formulae (II), (III), (VI) and the amine $NHR_3R_4$ are either commercially available or can be obtained by the person skilled in the art using conventional chemical reactions described in the literature.

More specifically, the phosphate compounds of formula (I) according to the invention will be useful in the treatment of chemo- or radio-resistant cancers and also in malignant haemopathies and small-cell lung cancer.

Among the cancer treatments envisaged there may be mentioned, without implying any limitation, cancers of the bladder, brain, breast and uterus, chronic lymphoid leukaemias, colorectal cancer, cancers of the oesophagus and liver, lymphoblastic leukaemias, non-Hodgkin lymphomas, melanomas, malignant haemopathies, myelomas, ovarian cancer, non-small-cell lung cancer, prostate cancer and small-cell lung cancer. Among non-Hodgkin lymphomas, there may be mentioned more preferably follicular lymphomas, mantle cell lymphomas, diffuse large B-cell lymphomas, small lymphocytic lymphomas and marginal zone B-cell lymphomas.

The present invention relates also to pharmaceutical compositions comprising at least one compound of formula (I) in combination with one or more pharmaceutically acceptable excipients.

Among the pharmaceutical compositions according to the invention there may be mentioned more especially those that are suitable for oral, parenteral, nasal, per- or trans-cutaneous, rectal, perlingual, ocular or respiratory administration, especially tablets or dragées, sublingual tablets, sachets, paquets, capsules, glossettes, lozenges, suppositories, creams, ointments, dermal gels, and drinkable or injectable ampoules.

The dosage varies according to the sex, age and weight of the patient, the administration route, the nature of the therapeutic indication, or of any associated treatments, and ranges from 0.01 mg to 1 g per 24 hours in one or more administrations.

Furthermore, the present invention relates also to the association of a compound of formula (I) with an anticancer agent selected from genotoxic agents, mitotic poisons, anti-metabolites, proteasome inhibitors, kinase inhibitors and antibodies, and also to pharmaceutical compositions comprising that type of association and their use in the manufacture of medicaments for use in the treatment of cancer.

The compounds of the invention may also be used in association with radiotherapy in the treatment of cancer.

The following Preparations and Examples illustrate the invention without limiting it in any way.

Preparation 1: 6-[1-(Methoxycarbonyl)-5,6,7,8-tetrahydro-3-indolizinyl]-1,3-benzodioxole-5-carboxylic acid Step A: 1-Formyl-2-piperidine-carboxylic acid To a solution of 40 g of a racemic mixture of 2-piperidine-carboxylic acid (0.310 mmol) in 300 mL of formic acid placed at 0° C. there are added, dropwise, 200 mL (2.15 mmol) of acetic anhydride. The batch is then stirred at ambient temperature overnight. Then, the reaction mixture is cooled to 0° C., hydrolysed by adding 250 mL of water, and stirred for half an hour at 0° C. before being concentrated to dryness. The oil thereby obtained is taken up in 200 mL of methanol and then concentrated to dryness. The title product is obtained in the form of an oil in a yield of 98%. It is used directly, without being otherwise purified, in the next Step.

$^1$H NMR: δ (400 MHz; dmso-d6; 300° K): 13.0 (m, 1H OH); 8.0-8.05 (2s, 1H aldehyde); 4.9-4.5 (2d, 1H a to the N and COOH); 4.1-2.6 (m, 2H a to the N); 2.2-1.2 (m, 6H piperidine)

IR: ν: —OH: 2000-3000 cm$^{-1}$ acid; ν: >C=O 1703 cm$^{-1}$ wide band

Step B: Methyl 5,6,7,8-tetrahydro-1-indolizine-carboxylate

To a solution of 10 g of the carboxylic acid obtained in Step A (63.6 mmol) in 65 mL of dichloroethane there are successively added 13.4 g of tosyl chloride (70.4 mmol), 11.5 mL of methyl 2-chloroacrylate (113.5 mmol) and then, dropwise, 17.8 mL of N,N,N-triethylamine (127.2 mmol). The reaction mixture is then refluxed for 1 hour 30 minutes. It is then placed at ambient temperature, and there are then added 5 mL of methyl 2-chloroacrylate (48.9 mmol) and, dropwise, 9 mL of N,N,N-triethylamine (64 mmol). The batch is refluxed overnight.

The reaction mixture is then diluted with methylene chloride, washed successively with 1M HCl solution, saturated aqueous $NaHCO_3$ solution and then with brine until a neutral pH is obtained. The organic phase is then dried over $MgSO_4$, filtered, concentrated to dryness and purified by chromatography over silica gel (heptane/AcOEt gradient). The title product is obtained in the form of an oil.

$^1$H NMR: δ (400 MHz; CDCl$_3$; 300° K): 6.55-6.40 (d, 2H, tetrahydroindolizine); 3.91 (t, 3H methyl ester); 3.78 (s, 3H tetrahydroindolizine); 3.08 (t, 2H, tetrahydroindolizine); 1.95-1.85 (m, 4H, tetrahydroindolizine)

IR: ν:>C=O 1692 cm$^{-1}$ ester

Step C: Methyl 3-(6-formyl-1,3-benzodioxol-5-yl)-5,6,7,8-tetrahydro-1-indolizine-carboxylate To a solution of 6.4 g of the ester obtained in Step B (35.7 mmol) in 12 mL of N,N-dimethylacetamide, there are successively added 12.3 g of 6-bromo-1,3-benzodioxole-5-carbaldehyde (53.6 mmol) and 7 g of potassium acetate (71.4 mmol), and then the batch is stirred under argon for 20 minutes. There are then added 1.3 g of palladium catalyst dichlorobis(triphenylphosphine)palladium(II) (PdCl$_2$(PPh$_3$)$_2$) (1.8 mmol). The reaction mixture is then heated at 130° C. for one hour before adding 139 μL of H$_2$O thereto. Heating is maintained at that same temperature overnight. The mixture is allowed to return to ambient temperature and it is then diluted with AcOEt. Animal charcoal (25 g per g of product) is added and the batch is stirred at ambient temperature for 1 hour and then filtered. The organic phase is then washed with water, dried over magnesium sulphate and concentrated to dryness. The crude product thereby obtained is purified by chromatography over silica gel (heptane/AcOEt gradient). The title product is obtained in the form of an oil.

$^1$H NMR: δ: (400 MHz; dmso-d6; 353° K): 9.65 (s, 1H, H aldehyde); 7.3-7.15 (2s, 2H, aromatic Hs); 6.45 (s, 1H tetrahydroindolizine); 6.20 (s, 2H methylenedioxy); 3.70 (s, 3H methyl ester); 3.5-4.0 (m, 2H tetrahydroindolizine); 3.05 (m, 2H tetrahydroindolizine); 1.85 (m, 4H tetrahydroindolizine)

IR: ν: >C=O 1695 cm$^{-1}$ ester; ν: >C=O 1674 cm$^{-1}$

Step D: 6-[1-(Methoxycarbonyl)-5,6,7,8-tetrahydro-3-indolizinyl]-1,3-benzodioxole-5-carboxylic acid A solution containing 3.37 g of the compound obtained in Step C (10.3 mmol) in 9.3 mL of acetone and 8.8 mL (80.24 mmol) of 2-methyl-2-butene is prepared and placed at 0° C. There are added, dropwise, 9.3 mL of an aqueous solution containing a mixture of 3.3 g of sodium chlorite (NaClO$_2$) (36.05 mmol) and 3.6 g of sodium dihydrogen phosphate monohydrate (NaH$_2$PO$_4$) (25.75 mmol). The batch is then stirred at ambient temperature for 7 hours. The reaction mixture is then concentrated in order to remove the acetone. The solid then obtained is filtered off, washed with water and then dried at 40° C. in vacuo overnight. The title product is obtained in the form of a solid, which is subsequently used without being otherwise purified.

$^1$H NMR: δ (400 MHz; dmso-d6; 300° K): 12.10 (m, 1H, H carboxylic acid); 7.40-6.88 (2s, 2H, aromatic Hs); 6.20 (s, 1H, H tetrahydroindolizine); 6.18 (s, 2H, H methylenedioxy); 3.70 (s, 3H, methyl ester); 3.55 (t, 2H tetrahydroindolizine); 3.00 (t, 2H tetrahydroindolizine); 1.80 (m, 4H, H tetrahydroindolizine)

IR: ν: —OH: 3000-2000 cm$^{-1}$ acid; ν: >C=O 1686-1676 cm$^{-1}$ ester+acid; ν: >C=C<1608 cm$^{-1}$

Preparation 2: 2-[1-(Methoxycarbonyl)-5,6,7,8-tetrahydro-3-indolizinyl]benzoic acid The procedure is in accordance with the protocol described in Preparation 1, replacing the 6-bromo-1,3-benzodioxole-5-carbaldehyde used in Step C by 2-bromo-benzaldehyde.

Preparation 3: 6-[1-(Methoxycarbonyl)-3-indolizinyl]-1,3-benzodioxole-5-carboxylic acid

Step A: 1-(Carboxymethyl)-1,2-dihydropyridinium bromide

To a solution of 16.2 mL of pyridine (200 mmol) in 120 mL of ethyl acetate there are added, in portions, 27.8 g (200 mmoles) of bromoacetic acid. The batch is then stirred at ambient temperature overnight. The precipitate thereby obtained is filtered off and then washed with cold ethyl acetate. After drying, the title product is obtained in the form of a powder which is used directly in the next Step.

$^1$H NMR: δ (400 MHz; dmso-d6; 300° K): 9.15 (d, 2H, aromatic Hs pyridine); 8.7 (t, 1H, aromatic H); 8.25 (t, 2H, aromatic H); 5.65 (s, 2H, H CH$_2$COOH)

IR: ν: C=O: 1732 cm$^{-1}$; —OH acid: 2800 cm$^{-1}$

Step B: Methyl 1-indolizinecarboxylate

To a suspension of 6.55 g of the pyridinium salt obtained in Step A (30 mmol) in 240 mL of toluene there are successively added 16.7 mL of methyl acrylate (150 mmol), 4.2 mL of triethylamine (30 mmol) and then, in portions, 20.9 g of MnO$_2$ (240 mmol). The batch is then heated at 90° C. for 3 hours. After cooling, the reaction mixture is filtered over a cake of Celite and concentrated to dryness. The title product is then isolated by purification over silica gel (heptane/AcOEt gradient: 0-10%) in the form of an oil which crystallises in the cold state.

$^1$H NMR: δ (300 MHz; dmso-d6; 300° K): 8.5 (d, 1H, H indolizine); 8.05 (d, 1H, H indolizine); 7.6 (s, 1H, H indolizine); 7.15 (m, 2H, H indolizine); 6.85 (m, 1H, H indolizine); 4.25 (q, 2H, —C(O)CH$_2$CH$_3$); 1.35 (t, 3H, —C(O)CH$_2$CH$_3$)

IR: ν: C=O ester: 1675 cm$^{-1}$; aromatic C=C moieties: 1634 cm$^{-1}$

Step C: 6-[1-(Methoxycarbonyl)-3-indolizinyl]-1,3-benzodioxole-5-carboxylic acid The procedure is in accordance with the protocol described in Steps C and D of Preparation 1.

Preparation 4: 4-Chloro-2-[4-(ethoxycarbonyl)-1,5-dimethyl-1H-pyrrol-2-yl]-benzoic acid

Step A: Ethyl 1,2-dimethyl-1H-pyrrole-3-carboxylate

To a solution of 10 g of ethyl 2-methyl-1H-pyrrole-3-carboxylate (65.3 mmol) and 8.95 mL (130.6 mmol) of methyl iodide in 70 mL of dimethylformamide placed at 0° C. there are added, in three portions, 2.61 g (65.3 mmol) of sodium hydride 60%. The batch is then stirred at 0° C. for 1 hour. Then, the reaction mixture is hydrolysed by the addition of 420 mL of ice-cold water. The reaction mixture is then diluted with ethyl acetate, successively washed with 0.1M HCl solution, saturated aqueous LiCl solution and then brine. The organic phase is then dried over MgSO$_4$, filtered, concentrated to dryness and purified by chromatography over silica gel (petroleum ether/AcOEt gradient).

$^1$H NMR: δ (400 MHz; dmso-d6; 300K): 6.65 (d, 1H pyrrole); 6.3 (Id, 1H pyrrole); 4.1 (1q, 2H, OCH$_2$CH$_3$); 3.5 (s, 3H N-pyrrole); 2.4 (s, 3H pyrrole); 1.5 (it, 3H OCH$_2$CH$_3$)

IR: ν: >C=O: 1688 cm$^{-1}$; ν: C—O—C: 1172 cm$^{-1}$

Step B: Ethyl 5-(5-chloro-2-formylphenyl)-1,2-dimethyl-1H-pyrrole-3-carboxylate To a solution of 10.5 g of the compound obtained in Step A (62.8 mmol) in 65 mL of N,N-dimethylacetamide there are successively added 15.2 g of 2-bromo-4-chlorobenzaldehyde (69 mmol), 12.3 g of potassium acetate (125.6 mmol) and then the batch is stirred under argon for 20 minutes. There are then added 2.2 g of palladium catalyst PdCl$_2$(PPh$_3$)$_2$ (3.14 mmol). The reaction mixture is then heated at 130° C. overnight. The mixture is allowed to return to ambient temperature and it is then diluted with dichloromethane. Animal charcoal is added (30 g) and the batch is stirred at ambient temperature for 1 hour and then filtered. The organic phase is then washed with water, dried over magnesium sulphate and concentrated to dryness. The crude product thereby obtained is purified by chromatography over silica gel (petroleum ether/AcOEt gradient). The title product is obtained in the form of a solid.

$^1$H NMR: δ (400 MHz; dmso-d6; 300K): 9.8 (s, 1H, formyl); 7.91-7.69-7.61 (d, 3H, aromatic Hs); 6.5 (s, 1H pyrrole); 4.2 (q, 2H, OCH$_2$CH$_3$); 3.4 (s, 3H, CH$_3$—N-pyrrole); 2.55 (s, 3H pyrrole); 1.28 (t, 3H, OCH$_2$CH$_3$)

Step C: 4-Chloro-2-[4-(ethoxycarbonyl)-1,5-dimethyl-1H-pyrrol-2-yl]benzoic acid

A solution is prepared containing 12.85 g of the compound obtained in Step B (42 mmol) and 35.7 mL (336 mmol) of 2-methyl-2-butene in a mixture containing 20 mL of acetone and 20 mL of tetrahydrofuran. There are added, dropwise, 200 mL of an aqueous solution containing a mixture of 13.3 g of sodium chlorite (NaClO$_2$) (147 mmol) and 14.5 g of sodium dihydrogen phosphate monohydrate (NaH$_2$PO$_4$.H$_2$O) (105 mmol). The batch is then vigorously stirred at ambient temperature for 7 hours. The reaction mixture is then concentrated to remove the acetone. Ethyl acetate is added, and the organic phase is washed with water and then concentrated to dryness. The residue is then taken up in a minimum of ethyl ether. The solid then obtained is filtered off, washed with ether and then dried in vacuo at 40° C. overnight. The title product is obtained in the form of a solid, which is subsequently used without being otherwise purified.

$^1$H NMR: δ (400 MHz; dmso-d6; 300K): 13 (m, 1H COOH); 7.85-7.6-7.41 (d, dd, wd, 3H, aromatic Hs); 6.3 (s, 1H, H pyrrole); 4.15 (q, 2H, OCH$_2$CH$_3$); 3.25 (s, 3H, CH$_3$—N-pyrrole); 2.5 (s, 3H, CH$_3$-pyrrole); 1.25 (t, 3H, OCH$_2$CH$_3$)
IR: v: —OH: 3100-2500 cm$^{-1}$ acid; v: >C=O: 1681 cm$^{-1}$ ester+acid Preparation 5: 6-[4-(Ethoxycarbonyl)-1,5-dimethyl-1H-pyrrol-2-yl]-1,3-benzodioxole-5-carboxylic acid The procedure is in accordance with the process of Preparation 4, replacing the 2-bromo-4-chlorobenzaldehyde used in Step B by 6-bromo-1,3-benzodioxole-5-carbaldehyde.

Preparation 6: 4-Fluoro-3-methoxy-2-[4-(ethoxycarbonyl)-1,5-dimethyl-1H-pyrrol-2-yl]benzoic acid The procedure is in accordance with the process of Preparation 4, replacing the 2-bromo-4-chlorobenzaldehyde used in Step B by 2-bromo-4-fluoro-3-methoxybenzaldehyde.

Preparation 7: 4-Fluoro-2-[4-(ethoxycarbonyl)-1,5-dimethyl-1H-pyrrol-2-yl]benzoic acid The procedure is in accordance with the process of Preparation 4, replacing the 2-bromo-4-chlorobenzaldehyde used in Step B by 2-bromo-4-fluorobenzaldehyde.

Preparation 8: 7-[4-(Methoxycarbonyl)-1,5-dimethyl-1H-pyrrol-2-yl]-2,3-dihydro-1,4-benzodioxin-6-carboxylic acid The procedure is in accordance with the process of Preparation 4, replacing the ethyl 2-methyl-1H-pyrrole-3-carboxylate in Step A by methyl 2-methyl-1H-pyrrole-3-carboxylate and the 2-bromo-4-chlorobenzaldehyde used in Step B by 7-bromo-2,3-dihydro-1,4-benzodioxin-6-carbaldehyde.

Preparation 9: 5-Benzyloxy-2-(1-methoxycarbonyl-5,6,7,8-tetrahydroindolizin-3-yl)benzoic acid Step A: Methyl 3-(4-benzyloxy-2-formyl-phenyl)-5,6,7,8-tetrahydroindolizine-1-carboxylate 5-Benzyloxy-2-bromo-benzaldehyde (12.3 g, 42.2 mmol) is introduced into a flask in the presence of potassium acetate (8.3 g; 84.2 mmol) and 120 mL of dimethylacetamide. After degassing under argon, dichlorobis(triphenylphosphine)palladium (II) (1.04 g, 1.5 mmol) is added and the mixture is then degassed under argon before being heated at 100° C. for 16 hours. After returning to ambient temperature, the reaction mixture is poured into 200 mL of ethyl acetate, filtered over Celite, and washed with water and then with brine. The combined aqueous phases are extracted with ethyl acetate. The organic phases are dried over sodium sulphate, filtered and concentrated under reduced pressure. The residue obtained is purified by chromatography over silica gel in order to obtain the title product.

Step B: 5-Benzyloxy-2-(1-methoxycarbonyl-5,6,7,8-tetrahydroindolizin-3-yl)benzoic acid To a solution of the compound obtained in Step B (4.63 g, 11.89 mmol) in 300 mL of acetone there is added 2-methyl-2-butene (6.31 mL, 59 mmol). A solution of sodium dihydrogen phosphate monohydrate (6.56 g, 47.6 mmol) and sodium chlorite (2.69 g, 23.8 mmol) in 40 mL of water is then poured in dropwise whilst maintaining the temperature below 20° C. After stirring for 30 minutes at ambient temperature, the mixture is acidified with 2M HCl solution and then the phases are separated. The aqueous phase is extracted with ethyl acetate. The combined organic phases are dried over sodium sulphate, filtered and evaporated to dryness to provide the expected compound.

Preparation 1': (3S)-3-(4-Morpholinylmethyl)-1,2,3,4-tetrahydroisoquinoline

Step A: Benzyl (3S)-3-(4-morpholinylcarbonyl)-3,4-dihydro-2(1H)-isoquinoline-carboxylate To a solution of 5 g of (3S)-2-[(benzyloxy)carbonyl]-1,2,3,4-tetrahydro-3-isoquinolinecarboxylic acid (16 mmol) in 160 mL of dichloromethane there are added 1.5 mL of morpholine (17.6 mmol), then 9 mL of N,N,N-triethylamine (64 mmol), 3.3 g of 1-ethyl-3-(3'-dimethylaminopropyl)-carbodiimide (EDC) (19.2 mmol) and 2.6 g of hydroxybenzotriazole (HOBt) (19.2 mmol). The reaction mixture is stirred at ambient temperature overnight; it is then poured into aqueous ammonium chloride solution and extracted with ethyl acetate. The organic phase is then dried over magnesium sulphate, and then filtered and evaporated to dryness. The crude product thereby obtained is then purified by chromatography over silica gel (dichloromethane/methanol gradient). The product is obtained in the form of a foam.

$^1$H NMR: δ (400 MHz; dmso-d6; 353K): 7.30 (m, 5H benzyl); 7.15 (m, 4H, aromatic Hs); 5.2-5.0 (m, 3H, 2H benzyl, 1H dihydroisoquinoline); 4.75-4.5 (2d, 2H dihydroisoquinoline); 3.55-3.3 (m, 8H morpholine); 3.15-2.9 (2dd, 2H dihydroisoquinoline)
IR: v: >C=O: 1694; 1650 cm$^{-1}$ Step B: Benzyl (3S)-3-(4-morpholinylmethyl)-3,4-dihydro-2(1H)-isoquinolinecarboxylate To a solution of 5.3 g of the product obtained in Step A (13.9 mmol) in 278 mL of tetrahydrofuran there are added 14 mL of borane-dimethylsulphide complex (BH$_3$Me$_2$S) (27.8 mmol) at ambient temperature. The batch is heated for 4 hours at 80° C. It is allowed to return to ambient temperature and there are then added 7 mL (14 mmol) of BH$_3$Me$_2$S. The reaction mixture is again heated at 80° C. for 2 hours. The tetrahydrofuran is then evaporated off and then there is slowly added methanol and then 5.6 mL of 5M hydrochloric acid (27.8 mmol). The mixture is stirred at ambient temperature overnight, and then at 80° C. for 1 hour. Saturated aqueous NaHCO$_3$ solution is then added to the reaction mixture placed at 0° C. until a pH of 8 is obtained, and extraction with ethyl acetate is then carried out. The organic phase is then dried over magnesium sulphate, and then filtered and evaporated to dryness. The title product is obtained in the form of an oil.

$^1$H NMR: δ (400 MHz; dmso-d6; 353K): 7.43-7.30 (unresolved peak, 5H benzyl); 7.19 (m, 4H, aromatic Hs); 5.16 (m, 2H, 2H benzyl); 4.79-4.29 (d, 2H dihydroisoquinoline); 4.58 (m, 1H dihydroisoquinoline); 3.50 (m, 4H morpholine); 3.02-2.80 (dd, 2H dihydroisoquinoline); 2.42-2.28 (unresolved peak, 5H, 4H morpholine, 1H morpholine); 2.15 (dd, 1H morpholine)

IR: v: >CH: 2810 cm$^{-1}$; v: >C=O: 1694 cm$^{-1}$; v: >C—O—C<: 1114 cm$^{-1}$; v: >CH—Ar: 751; 697 cm$^{-1}$

Step C: (3S)-3-(4-Morpholinylmethyl)-1,2,3,4-tetrahydroisoquinoline

To a solution of 4.9 g of the compound of Step B (13.4 mmol) in 67 mL of ethanol there is added 0.980 g of palladium dihydroxide (20% by weight) at ambient temperature. The reaction mixture is placed under 1.2 bars of hydrogen at ambient temperature for 4 hours. It is then passed through a Whatman filter and the palladium is then rinsed several times with ethanol. The filtrate is evaporated to dryness. The title product is obtained in the form of an oil.

$^1$H NMR: δ (400 MHz; dmso-d6; 300K): 7.12-7.0 (unresolved peak, 4H, aromatic Hs); 3.92 (s, 2H tetrahydroisoquinoline); 3.60 (t, 4H morpholine); 2.98 (m, 1H tetrahydroisoquinoline); 2.68 (dd, 1H tetrahydroisoquinoline); 2.5-2.3 (unresolved peak, 8H, 1H tetrahydroisoquinoline, 6H morpholine, 1H NH)

IR: v: >NH: 3322 cm$^{-1}$; v: >C—O—C<: 1115 cm$^{-1}$; v: >CH—Ar: 742 cm$^{-1}$

Preparation 2':
(3R)-3-Methyl-1,2,3,4-tetrahydroisoquinoline hydrochloride

Step A: {(3S)-2-[(4-Methylphenyl)sulphonyl]-1,2,3,4-tetrahydroisoquinolin-3-yl}methyl 4-methylbenzenesulphonate To a solution of 30.2 g of [(3S)-1,2,3,4-tetrahydroisoquinolin-3-yl]methanol (185 mmol) in 750 mL of dichloromethane there are successively added 91.71 g of tosyl chloride (481 mmol) and then, dropwise, 122.3 mL of N,N,N-triethylamine (740 mmol). The reaction mixture is then stirred at ambient temperature for 20 hours. It is then diluted with dichloromethane, washed successively with 1M HCl solution, saturated aqueous NaHCO$_3$ solution and then brine until neutral. The organic phase is then dried over MgSO$_4$, filtered and concentrated to dryness. The solid obtained is then dissolved in a minimum volume of dichloromethane and then cyclohexane is added until a precipitate is formed. This precipitate is then filtered off and washed with cyclohexane. After drying, the title product is obtained in the form of crystals.

$^1$H NMR: δ (400 MHz; dmso-d6; 300° K): 7.75 (d, 2H, aromatic Hs, ortho O-tosyl); 7.6 (d, 2H, aromatic Hs, ortho N-tosyl); 7.5 (d, 2H, aromatic Hs, meta O-tosyl); 7.3 (d, 2H, aromatic Hs, meta N-tosyl); 7.15-6.9 (m, 4H, aromatic Hs, tetrahydroisoquinoline); 4.4-4.15 (dd, 2H, aliphatic Hs, tetrahydroisoquinoline); 4.25 (m, 1H, aliphatic H, tetrahydroisoquinoline); 4.0-3.8 (2dd, 2H, aliphatic Hs, CH$_2$—O-tosyl); 2.7 (2dd, 2H, aliphatic Hs, tetrahydroisoquinoline); 2.45 (s, 3H, O—SO$_2$-Ph-CH$_3$); 2.35 (s, 3H, N—SO$_2$-Ph-CH$_3$)

IR: v: —SO$_2$: 1339-1165 cm$^{-1}$

Step B: (3R)-3-Methyl-2-[(4-methylphenyl)sulphonyl]-1,2,3,4-tetrahydroisoquinoline To a suspension of 8.15 g (214.8 mmol) of LiAlH$_4$ in 800 mL of methyl tert-butyl ether (MTBE) there are added 101.2 g of the ditosyl compound obtained in Step A (214.8 mmol) dissolved in 200 mL of MTBE. The batch is then heated at 50° C. for 2 hours. It is allowed to cool and placed at 0° C., and there are then added, dropwise, 12 mL of 5M NaOH solution. The batch is stirred at ambient temperature for 45 minutes. The solid thereby obtained is then filtered off and washed with MTBE and then with dichloromethane. The filtrate is then concentrated to dryness. The title product is then obtained in the form of a solid.

$^1$H NMR: δ (400 MHz; dmso-d6; 300° K): 7.70 (d, 2H, aromatic Hs, ortho N-tosyl); 7.38 (d, 2H, aromatic Hs, meta N-tosyl); 7.2-7.0 (m, 4H, aromatic Hs, tetrahydroisoquinoline); 4.4 (m, 2H, aliphatic Hs, tetrahydroisoquinoline); 4.3 (m, 1H, aliphatic H, tetrahydroisoquinoline); 2.85-2.51 (2dd, 2H, aliphatic Hs, tetrahydroisoquinoline); 2.35 (s, 3H, N—SO$_2$-Ph-CH$_3$); 0.90 (d, 3H, tetrahydroisoquinoline-CH$_3$)

IR: v: —SO$_2$: 1332-1154 cm$^{-1}$

Step C:
(3R)-3-Methyl-1,2,3,4-tetrahydroisoquinoline

To a solution of 31.15 g (103.15 mmol) of the monotosyl compound obtained in Step B in 500 mL of anhydrous methanol there are added, in portions, 3.92 g (161 mmol) of magnesium turnings. The batch is stirred in the presence of ultrasound for 96 hours. The reaction mixture is then filtered and the solid is washed several times with methanol. The filtrate is then concentrated to dryness. After purification by chromatography over silica gel (dichloromethane/EtOH/NH$_4$OH gradient), the title product is obtained in the form of an oil.

$^1$H NMR: δ (400 MHz; dmso-d6; 300° K): 7.05 (m, 4H, aromatic Hs, tetrahydroisoquinoline); 3.90 (m, 2H, aliphatic Hs, tetrahydroisoquinoline); 2.85 (m, 1H, aliphatic H, tetrahydroisoquinoline); 2.68-2.4 (2dd, 2H, aliphatic Hs, tetrahydro-isoquinoline); 1.12 (d, 3H, tetrahydroisoquinoline-CH$_3$); 2.9-2.3 (m, broad, 1H, HN (tetrahydroisoquinoline))

IR: v: —NH: 3248 cm$^{-1}$

Step D:
(3R)-3-Methyl-1,2,3,4-tetrahydroisoquinoline hydrochloride

To a solution of 14.3 g (97.20 mmol) of the compound obtained in Step C in 20 mL of anhydrous ethanol there are added, dropwise, 100 mL of a 1M solution of HCl in ether. The batch is stirred at ambient temperature for 1 hour and then filtered. The crystals thereby obtained are washed with ethyl ether. After drying, the title product is obtained in the form of crystals.

$^1$H NMR: δ (400 MHz; dmso-d6; 300° K): 9.57 (m, broad, 2H, NH$_2^+$ (tetrahydro-isoquinoline); 7.22 (m, 4H, aromatic Hs, tetrahydroisoquinoline); 4.27 (s, 2H, aliphatic Hs, tetrahydroisoquinoline); 3.52 (m, 1H, aliphatic H, tetrahydroisoquinoline); 3.03-2.85 (2dd, 2H, aliphatic Hs, tetrahydroisoquinoline); 1.39 (d, 3H, tetrahydroisoquinoline-CH$_3$)

IR: ν: —NH₂⁺: 3000-2300 cm⁻¹; ν: aromatic —CH: 766 cm⁻¹

Preparation 3': (3R)-3-[3-(Morpholin-4-yl)propyl]-1,2,3,4-tetrahydroisoquinoline

Step A: {(3S)-2-[(4-Methylphenyl)sulphonyl]-1,2,3,4-tetrahydroisoquinolin-3-yl}methyl 4-methylbenzenesulphonate The procedure is the same as that of Step A of Preparation 2'.

Step B: tert-Butyl 2-({(3R)-2-[(4-methylphenyl)sulphonyl]-1,2,3,4-tetrahydroisoquinolin-3-yl}methyl)-3-(morpholin-4-yl)-3-oxopropanoate To a suspension of 1 g of NaH (60%) (25.08 mmol) in 30 mL of MTBE there are added, dropwise, a solution of 5 g of tert-butyl 3-morpholino-3-oxopropanoate (21.81 mmol) in 20 mL of anhydrous MTBE. This suspension is stirred at ambient temperature for 1 hour and then the compound obtained in Step A is added in the form of a powder. The batch is stirred at 60° C. for 30 hours. 100 mL of saturated aqueous ammonium chloride solution are added. The resulting solution is extracted with dichloromethane. The organic phase is then dried over MgSO₄, filtered and concentrated to dryness. After purification by chromatography over silica gel (dichloromethane/MeOH gradient), the expected product is obtained in the form of an oil.

¹H NMR (500 MHz, dmso-d6) δ ppm: 7.63/7.59 (2d, 2 H), 7.3/7.26 (2d, 2 H), 7.13 (m, 2 H), 7.09/6.97 (2t, 2 H), 4.64/4.55/4.36/4.28 (2AB, 2 H), 4.25/4.11 (2m, 1 H), 3.81 (m, 1 H), 3.73-3.48 (m, 4 H), 3.57-3.32 (m, 4 H), 2.51 (m, 2 H), 2.32/2.31 (2s, 3 H), 1.88/1.79 (2m, 2 H), 1.39/1.38 (2s, 9 H)

IR (ATR) cm⁻¹: ν: >C=O: 1731 (ester); ν: >C=O: 1644 (amide); ν: —SO2: 1334-1156; ν: >C—O—C<: 1115; γ: >CH—Ar: 815-746-709

Step C: 2-({(3R)-2-[(4-Methylphenyl)sulphonyl]-1,2,3,4-tetrahydroisoquinolin-3-yl}methyl)-3-(morpholin-4-yl)-3-oxopropanoic acid To a solution of 9.5 g (17.97 mmol) of the compound obtained in Step B in 40 mL of dioxane there are added, dropwise, 20 mL of a 4M solution of HCl in dioxane. The batch is stirred at ambient temperature for 48 hours and then the solution is concentrated to dryness. After drying, the expected product is obtained in the form of an oil.

¹H NMR (400 MHz, dmso-d6) δ ppm: 12.75 (m, 1 H), 7.6 (2*d, 2 H), 7.3 (2*d, 2 H), 7.1/6.95 (2*m, 4 H), 4.7-4.2 (d, 2 H), 4.25/4.12 (2*m, 1 H), 3.9-3.3 (m, 9 H), 2.55 (d, 2 H), 2.3 (2*s, 3 H), 1.8 (t, 2 H)

IR (ATR) cm⁻¹: ν: —OH: 3500 to 2000; ν: >C=O: 1727 (acid); ν: >C=O: 1634 (amide); ν: —SO2: 1330-1155

Step D: 3-{(3R)-2-[(4-Methylphenyl)sulphonyl]-1,2,3,4-tetrahydroisoquinolin-3-yl}-1-(morpholin-4-yl)propan-1-one To a solution of 7.80 g (16.51 mmol) of the compound obtained in Step C in 100 mL of DMSO there are added 1.16 g (19.83 mmol) of solid sodium chloride and then, dropwise, 5 mL of water. The batch is stirred at 130° C. for 1 hour and then the solution is concentrated to ¾. The reaction mixture is then diluted with dichloromethane and washed successively with saturated aqueous lithium chloride solution and then with brine. The organic phase is then dried over MgSO₄, filtered and concentrated to dryness. After purification by chromatography over silica gel (cyclohexane/ethyl acetate gradient), the expected product is obtained in the form of an oil.

¹H NMR (400 MHz, dmso-d6) δ ppm: 7.65 (d, 2 H), 7.3 (d, 2 H), 7.15/7 (2 m, 4 H), 4.6 (d, 1 H), 4.25 (d, 1 H), 4.2 (m, 1 H), 3.5 (m, 4 H), 3.4 (2 m, 4 H), 2.6 (2 dd, 2 H), 2.35 (s, 3 H), 2.3 (m, 2 H), 1.5 (quad., 2 H)

IR (ATR) cm⁻¹: ν: >C=O: 1639; ν: —SO2: 1331-1156; γ: >CH—Ar: 815-675

Step E: (3R)-2-[(4-Methylphenyl)sulphonyl]-3-[3-(morpholin-4-yl)propyl]-1,2,3,4-tetrahydroisoquinoline To a solution of 6.0 g (14.0 mmol) of the compound obtained in Step D in 60 mL of MTBE and 14 mL of dichloromethane there are added 1.06 g (28 mmol) of LAH in portions over 5 minutes. The batch is stirred at ambient temperature for 15 hours. There are added, dropwise, 1.5 mL of water and stirring is carried out for 15 minutes. There are then added, dropwise, 1.5 mL of 5M sodium hydroxide solution and stirring is carried out for 15 minutes. The reaction mixture is then diluted with MTBE and dichloromethane. The suspension is then filtered and the precipitate is washed with MTBE and dichloromethane. The organic phase is then dried over MgSO₄, filtered and concentrated to dryness. After purification by chromatography over silica gel (dichloromethane/EtOH/NH₄OH gradient), the expected product is obtained in the form of an oil.

¹H NMR (400 MHz, dmso-d6) δ ppm: 7.68 (d, 2 H), 7.32 (d, 2 H), 7.1 (unresolved peak, 4 H), 4.65/4.23 (AB, 2 H), 4.2 (m, 1 H), 3.55 (t, 4 H), 2.7/2.6 (ABx, 2 H), 2.35 (s, 3 H), 2.25 (t, 4 H), 2.2 (t, 2 H), 1.4/1.3 (2m, 4 H).

IR (ATR) cm⁻¹: ν: —SO2: 1333-1158

Step F: (3R)-3-[3-(Morpholin-4-yl)propyl]-1,2,3,4-tetrahydroisoquinoline

To a solution of 1.50 g (3.62 mmol) of the compound obtained in Step E in 20 mL of anhydrous methanol there are added 2.0 g (82.3 mmol), in portions, of magnesium turnings. The batch is stirred in the presence of ultrasound for 96 hours. The reaction mixture is then filtered, the solid is washed several times with methanol, and the filtrate is concentrated to dryness. After purification by chromatography over silica gel (dichloromethane/EtOH/NH₄OH gradient), the expected product is obtained in the form of an oil.

¹H NMR (400 MHz, dmso-d6) δ ppm: 7.3 (d, 2 H), 7.1 (t, 2 H), 7.1 (d+t, 3 H), 7 (d, 2 H), 3.9 (s, 2 H), 3.55 (t, 4 H), 2.75 (m, 1 H), 2.72/2.45 (dd, 2 H), 2.35 (t, 4 H), 2.25 (t, 2 H), 1.6 (m, 2 H), 1.45 (m, 2 H)

IR (ATR) cm⁻¹: ν: >NH2+/NH+: 3500-2300; ν: >C—O—C<: 1115

High-Resolution Mass Spectrometry (ESI+−/FIA/HR):
Empirical formula: $C_{16}H_{24}N_2O$
[M+H]⁺ calculated: 261.1961
[M+H]⁺ measured: 261.1959

Preparation 4': (3R)-3-(4-Morpholinylmethyl)-1,2,3,4-tetrahydroisoquinoline

The procedure is in accordance with the process of Preparation 1', replacing the (3S)-2-[(benzyloxy)carbonyl]-1,2,3, 4-tetrahydro-3-isoquinolinecarboxylic acid used in Step A by (3R)-2-[(benzyloxy)carbonyl]-1,2,3,4-tetrahydro-3-isoquinolinecarboxylic acid.

Preparation 1": 4-{[tert-Butyl(dimethyl)silyl]oxy}-N-phenylaniline

To a solution of 12 g of 4-anilinophenol (64.7 mmol) in 200 mL of acetonitrile there are added, at ambient temperature, 6.7 g of imidazole (97.05 mmol) and 11.7 g of tert-butyl (chloro)dimethylsilane (77.64 mmol). The batch is stirred at 70° C. for 4 hours. The reaction mixture is then poured into water and extracted with ether. The organic phase is then dried over magnesium sulphate, then filtered and evaporated to dryness. The crude product thereby obtained is then purified by chromatography over silica gel (petroleum ether/dichloromethane gradient). The title product is obtained in the form of a powder.

$^1$H NMR: δ (400 MHz; dmso-d6; 300K): 7.84 (s, 1H NH); 7.17 (t, 2H aniline); 6.98 (d, 2H phenoxy); 6.94 (d, 2H aniline); 6.76 (d, 2H phenoxy); 6.72 (t, 1H aniline); 0.95 (s, 9H tert-butyl); 0.15 (s, 6H dimethyl)

IR: ν: >NH: 3403 cm$^{-1}$; ν:>Ar: 1597 cm$^{-1}$

Preparation 2": N-(4-{[tert-Butyl(dimethyl)silyl]oxy}phenyl)-1-methyl-1H-indol-5-amine The procedure is in accordance with the process of Preparation 5", replacing the 4-bromo-1-methyl-1H-pyrazole used in Step B by 5-bromo-1-methyl-1H-indole.

Preparation 3": N-(4-{[tert-Butyl(dimethyl)silyl]oxy}phenyl)-1-methyl-1H-pyrrolo[2,3-b]pyridin-5-amine The procedure is in accordance with the process of Preparation 5", replacing the 4-bromo-1-methyl-1H-pyrazole used in Step B by 5-bromo-1-methyl-1H-pyrrolo[2,3-b]pyridine (obtained in accordance with a protocol from the literature: *Heterocycles*, 60(4), 865, 2003).

IR: ν: —NH—: 3278 cm$^{-1}$; ν: aromatic —C=C— moieties: 1605 cm$^{-1}$

Preparation 4": N-(4-{[tert-Butyl(dimethyl)silyl]oxy}phenyl)pyridin-4-amine

The procedure is in accordance with the process of Preparation 5", replacing the 4-bromo-1-methyl-1H-pyrazole used in Step B by 4-bromopyridine.

IR: ν —NH—: 3200 and 2500 cm$^{-1}$; ν —Si—O—: 902 cm$^{-1}$; ν —Si—C—: 820 cm$^{-1}$ Preparation 5": N-(4-{[tert-Butyl(dimethyl)silyl]oxy}phenyl)-1-methyl-1H-pyrazol-4-amine Step A: 4-{[tert-Butyl(dimethyl)silyl]oxy}aniline The title compound is obtained starting from 4-aminophenol in THF in the presence of imidazole and tert-butyl(chloro)dimethylsilane in accordance with the protocol described in the literature (S. Knaggs et al, *Organic & Biomolecular Chemistry*, 3(21), 4002-4010; 2005).

$^1$H NMR: δ (400 MHz; dmso-d6; 300K): 6.45-6.55 (dd, 4H, aromatic Hs); 4.60 (m, 2H, NH$_2$-Ph); 0.90 (s, 9H, Si (CH$_2$)$_2$CH(CH$_3$)$_2$); 0.10 (s, 6H, Si (CH$_2$)$_2$CH(CH$_3$)$_2$)

IR: ν: —NH$_2^+$: 3300-3400 cm$^{-1}$

Step B: N-[4-[tert-Butyl(dimethyl)silyl]oxyphenyl]-1-methyl-pyrazol-4-amine

To a solution of 30.8 g (0.137 mol) of the compound of Step A in 525 mL of anhydrous toluene there are successively added 29.8 g of sodium tert-butylate (0.310 mol), 4.55 g of Pd$_2$(dba)$_3$ (also referred to as tris(dibenzylideneacetone)dipalladium(0)) (4.96 mmol), 4.81 g of 2-di-tert-butylphosphino-2',4',6'-tri-isopropyl-1,1'-biphenyl (9.91 mmol) and 12.8 mL of 4-bromo-1-methyl-1H-pyrazole (0.124 mol). The batch is degassed under argon for 30 minutes and then refluxed for 3 hours. It is allowed to cool. The reaction mixture is concentrated to dryness and then taken up in dichloromethane, filtered over Celite and then concentrated to dryness again. The residue is then purified by chromatography over silica gel (gradient CH$_2$Cl$_2$/AcOEt) to provide the expected product in the form of a solid.

$^1$H NMR: δ (400 MHz; dmso-d6; 300K): 7.55 (s, 1H, pyrazole); 7.23 (s, 1H, pyrazole); 7.18 (broad s, 1H, NH$_2$-Ph); 6.64 (m, 4H, aromatic Hs); 3.77 (s, 3H, CH$_3$-pyrazole); 0.90 (s, 9H, Si(CH$_2$)$_2$CH(CH$_3$)$_2$); 0.12 (s, 6H, Si(CH$_2$)$_2$CH (CH$_3$)$_2$)

IR: ν —NH$^+$: 3275 cm$^{-1}$; ν Ar and C=N: 1577 and 1502 cm$^{-1}$; ν —Si—C—: 1236 cm$^{-1}$; ν —Si—O—: 898 cm$^{-1}$; ν —Si—C—: 828, 774 cm$^{-1}$ Preparation 6": N-{4-[(tert-Butyldimethylsilyl)oxy]phenyl}-1-trideuteriomethyl-1H-pyrazol-4-amine Step A: 4-Bromo-1-trideuteriomethyl-1H-pyrazole 4-Bromo-1H-pyrazole (9.05 g, 61.6 mmol) is added in portions to a suspension of sodium hydride (60% in oil) (2.83 g, 70.8 mmol) in tetrahydrofuran (90 mL) cooled in an ice bath. After having taken away the ice bath, the solution is stirred at ambient temperature for 0.5 hours. It is again cooled in an ice bath and iodomethane-d$_3$ (5.0 mL, 80.3 mmol) is added. The solution is stirred at ambient temperature for 19 hours. The suspension is then concentrated. The evaporation residue is triturated with tert-butyl methyl ether (90 mL) and filtered. The filtrate is concentrated in vacuo to obtain the expected compound in the form of an oil.

$^1$H NMR (400 MHz, CDCl$_3$) δ ppm: 7.37 (s, 1 H), 7.43 (s, 1 H)

Step B: N-{4-[(tert-Butyldimethylsilyl)oxy]phenyl}-1-trideuteriomethyl-1H-pyrazol-4-amine 4-Bromo-1-trideuteriomethyl-1H-pyrazole (9.6 g, 58.5 mmol), 4-[(tert-butyldimethyl-silyl)oxy]aniline (14.4 g, 64.6 mmol) and toluene (150 mL) are added to a 500-ml three-necked flask. The solution is degassed with nitrogen for 15 minutes, and then sodium tert-butylate (11.4 g, 0.12 mol), 2-di-tert-butylphosphino-2',4',6'-triisopropylbiphenyl (0.77 g, 1.81 mmol) and tris(dibenzylideneacetone)dipalladium(0) (1.64 g, 1.79 mmol) are successively added. The suspension is heated at 85° C. for 1.5 hours. The reaction mixture is then cooled to ambient temperature and water (270 mL) is added. The mixture is stirred for 30 minutes. Celite (30 g) is then added and the suspension is filtered on a bed of Celite. The phases of the filtrate are separated and the aqueous phase is extracted with ethyl acetate (3×200 mL). The combined organic phases are dried over sodium sulphate and filtered. The product is purified by chromatography over silica gel (ethyl acetate/heptane gradient). The product obtained is recrystallized from heptane (80 mL) to obtain the expected compound.

$^1$H NMR (400 MHz, CDCl$_3$) δ ppm: 0.16 (s, 6 H), 0.97 (s, 9 H), 4.92 (s, 1 H), 6.61-6.73 (m, 4 H), 7.25 (s, 1 H), 7.36 (s, 1 H)
$^{13}$C NMR (100 MHz, CDCl$_3$) δ ppm: −4.37, 18.28, 25.86, 38.67 (sept., $^1J_{C-D}$=21.0 Hz), 115.12, 120.73, 123.76, 126.52, 134.74, 141.07, 148.43
MS (ESI): [M+H]$^+$307.08

Preparation 7″: 4-({4-[(tert-Butyldimethylsilyl)oxy]phenyl}amino)-1,5-dimethyl-1H-pyrrole-2-carbonitrile

Step A: 4-Bromo-1,5-dimethyl-1H-pyrrole-2-carbonitrile

A solution of bromine (6.58 mL, 0.13 mol) in acetic acid (60 mL) is added dropwise, with the aid of a dropping funnel, to a solution of 1,5-dimethyl-1H-pyrrole-2-carbonitrile (15.0 g, 0.12 mol) in acetic acid (300 mL). The batch is stirred at ambient temperature for 24 hours. The reaction mixture is then poured into a beaker containing 300 mL of water.

The solid formed is filtered off and rinsed with water. It is then dissolved in dichloromethane (300 mL) and the organic phase is washed with brine, dried over sodium sulphate, filtered and concentrated in vacuo to yield the expected product in the form of a solid.
$^1$H NMR (CDCl$_3$) δ ppm: 2.25 (s, 3 H), 3.67 (s, 3 H), 6.74 (s, 1 H)

Step B: 4-({4-[(tert-Butyldimethylsilyl)oxy]phenyl}amino)-1,5-dimethyl-1H-pyrrole-2-carbonitrile A solution of the compound of the above Step (1.5 g, 7.53 mmol), 4-[(tert-butyldimethylsilyl)oxy]aniline (2.02 g, 9.04 mmol), sodium tert-butylate (1.45 g, 15.06 mmol) and 2-di-tert-butylphosphino-2',4',6'-triisopropylbiphenyl (0.13 g, 0.30 mmol) in toluene (20 mL) is purged with nitrogen. Tris(dibenzylideneacetone)-dipalladium(0) (0.28 g, 0.30 mmol) is added, and then the reaction mixture is heated at 90° C. until the reaction is complete (monitored by TLC). Heating is stopped and the mixture is allowed to return to ambient temperature. Water (75 mL) is added and the mixture is extracted with ethyl acetate (3×75 mL). The combined organic phases are washed with brine and then concentrated. The crude product is purified by flash chromatography over silica gel (ethyl acetate/heptane gradient). The product thereby obtained is dissolved in heptane in the warm state and is allowed to precipitate, with stirring, at ambient temperature, and then at 0° C. The solid is filtered off and the operation is repeated on the filtrate to yield the expected compound in the form of a solid.
$^1$H NMR (400 MHz, CDCl$_3$) δ ppm: 0.15 (s, 6 H), 0.97 (s, 9 H), 2.13 (s, 3 H), 3.66 (s, 3 H), 4.68 (br. s, 1 H), 6.49 (d, J=8.5 Hz, 2 H), 6.64 (s, 1 H), 6.66 (d, J=8.7 Hz, 2 H)
$^{13}$C NMR (100 MHz, CDCl$_3$) δ ppm: 4.34, 9.72, 18.30, 25.88, 32.94, 101.27, 114.37, 114.70, 116.41, 120.73, 124.52, 131.23, 141.54, 148.27
MS (ESI+): [M+H]$^+$ measured: 342.3

Preparation 8″: 4-[(4-{[tert-Butyl(dimethyl)silyl]oxy}phenyl)amino]-1-methyl-1H-pyrrole-2-carbonitrile

Step A: 1-Methyl-1H-pyrrole-2-carbonitrile

N,N-Dimethylformamide (3 mL) and 1,4-diazabicyclo[2.2.2]octane (0.49 g, 4.3 mmol) are added to a solution of pyrrole-2-carbonitrile (4 g, 43.4 mmol) in dimethyl carbonate (56 mL). The solution is stirred at 90° C. for 15 hours, and is then heated at 110° C. for 8 hours. The mixture is cooled to ambient temperature, and then ethyl acetate (80 mL) is added. The phases are separated and the organic phase is washed with water (2×80 mL) and 1M aqueous hydrochloric acid solution (1×80 mL). The combined aqueous phases are extracted again with ethyl acetate (1×80 mL). The combined organic phases are washed with brine (1×80 mL), dried over magnesium sulphate, filtered and concentrated in vacuo to obtain the expected product in the form of a liquid.
$^1$H NMR (400 MHz, CDCl$_3$) δ ppm: 3.78 (m, 2 H), 6.12-6.18 (m, 1 H), 6.74-6.82 (m, 1 H)

Step B: 4-Bromo-1-methyl-1H-pyrrole-2-carbonitrile

N-Bromosuccinimide (6.2 g, 34.9 mmol) is added to a solution of 1-methyl-1H-pyrrole-2-carbonitrile (3.7 g, 34.9 mmol) in N,N-dimethylformamide (150 mL). The solution is stirred for 15 hours at ambient temperature. Another amount of N-bromosuccinimide (2.0 g, 11 mmol) is added and the mixture is stirred for 3 hours. The product is purified by chromatography over silica gel (ethyl acetate/heptane gradient) to obtain the expected product in the form of a solid.
$^1$H NMR (400 MHz, CDCl$_3$) δ ppm: 3.77 (s, 3 H), 6.75 (d, J=1.7 Hz, 1 H), 6.80 (d, J=1.7 Hz, 1 H)

Step C: 4-[(tert-Butyldimethylsilyl)oxy]phenyl}amino)-1-methyl-1H-pyrrole-2-carbonitrile Nitrogen is bubbled through a solution of 4-bromo-1-methyl-1H-pyrrole-2-carbonitrile (2.82 g, 15.2 mmol) and 4-[(tert-butyldimethylsilyl)oxy]aniline (4.08 g, 18.3 mmol) in toluene (55 mL) for 5 minutes. Sodium tert-butylate (2.92 g, 30.4 mmol), tris(dibenzylideneacetone)dipalladium(0) (556 mg, 0.6 mmol) and 2-di-tert-butylphosphino-2',4',6'-triisopropylbiphenyl (255 mg, 0.6 mmol) are then added to the reaction mixture. The mixture is stirred for 1 hour at 80° C. under nitrogen. The suspension is then cooled to ambient temperature and filtered over Celite. The Celite cake is then rinsed with ethyl acetate. The filtrate is washed with water and then with brine. The organic phase is dried over magnesium sulphate, filtered and concentrated in vacuo. The product is purified twice by chromatography over silica gel (AcOEt/heptane gradient), and then by trituration in heptane to obtain the expected product in the form of a solid.
$^1$H NMR (400 MHz, CDCl$_3$) δ ppm: 0.16 (s, 6 H), 0.97 (s, 9 H), 3.73 (s, 3 H), 6.57 (d, J=1.9 Hz, 1 H), 6.64-6.66 (m, 1 H), 6.70 (s, 4 H); NMR
$^{13}$C NMR (100 MHz, CDCl$_3$) δ ppm: −4.48, 18.17, 25.72, 35.46, 103.01, 113.56, 113.69, 115.92, 119.55, 120.67, 129.04, 139.94, 148.85
MS (ESI+): [M+H]$^+$ 328.25

The amines NHR$_3$R$_4$ wherein R$_3$ and R$_4$, each independently of the other, represent an aryl or heteroaryl group are obtained in accordance with processes described in the literature (Surry D. S. et al., Chemical Science, 2011, 2, 27-50, Charles M. D. et al., Organic Letters, 2005, 7, 3965-3968). The reaction protecting the hydroxy function of the 4-anilinophenol described in Preparation 1″ can be applied to various secondary amines NHR$_3$R$_4$ (as defined hereinbefore) having one or more hydroxy functions, when they are available commercially. Alternatively, the secondary amines having at least one hydroxy substituent may be synthesised directly in a protected form, i.e. starting from reagents whose hydroxy function has been protected beforehand. Among the protecting groups, tert-butyl(dimethyl)silyloxy and benzyloxy are especially preferred.

Among the amines NHR$_3$R$_4$ having a hydroxy substituent that are used for synthesising the compounds of the invention there may be mentioned: 4-(4-toluidino)phenol, 4-(4-chloroanilino)phenol, 4-(3-fluoro-4-methylanilino)phenol, 4-[4-(trifluoromethoxy)anilino]-phenol, 4-[4-hydroxyanilino]phenol, {4-[(1-methyl-1H-indol-6-yl)amino]phenyl}-methanol, 4-(2,3-dihydro-1H-indol-6-ylamino)phenol, 4-[(1-methyl-2,3-dihydro-1H-indol-6-yl)amino]phenol, 4-[(1-methyl-1H-indol-6-yl)amino]phenol, 4-[(1-methyl-1H-indol-6-yl)amino]cyclohexanol, 4-[(1-methyl-1,2,3,4-tetrahydro-6-quinolinyl)amino]phenol, 4-[(4-methyl-3,4-dihydro-2H-1,4-benzoxazin-7-yl)amino]phenol, 4-[4-(diethylamino)anilino]-phenol, 4-(2,3-dihydro-1H-inden-5-ylamino)phenol, 4-[(1-methyl-1H-indazol-5-yl)amino]phenol, 4-[(1'-methyl-1',2'-dihydrospiro[cyclopropane-1,3'-indol]-5'-yl)amino]phenol, 4-[(1,3,3-trimethyl-2,3-dihydro-1H-indol-5-yl)amino]phenol, 4-[4-methoxy-3-(trifluoromethyl)anilino]phenol, 4-[4-(methylsulphanyl)-3-(trifluoromethyl)anilino]phenol, 2-fluoro-4-[(1-methyl-1H-indol-5-yl)amino]phenol, 4-[(1-ethyl-1H-indol-5-yl)amino]phenol, 4-[(1-ethyl-2,3-dihydro-1H-indol-5-yl)amino]phenol, 4-[(1-isopropyl-2,3-dihydro-1H-indol-5-yl)amino]phenol, 4-(butylamino)phenol, 3-[(1-methyl-1H-indol-5-yl)amino]-1-propanol, 4-[(1-methyl-1H-indol-5-yl)amino]-1-butanol, 4-[(3-fluoro-4-methylphenyl)-amino]phenol, 4-[(3-chloro-4-methylphenyl)amino]phenol, 4-[(4-fluorophenyl)amino]-phenol, 4-[(1-methyl-1H-pyrrolo[2,3-b]pyridin-5-yl)amino]phenol, 4-[(4-fluorophenyl)-amino]phenol, 4-[(2-fluorophenyl)amino]phenol, 4-[(3-fluorophenyl)amino]phenol, 4-[(2,4-difluorophenyl)amino]phenol, 4-[(3,4-difluorophenyl)amino]phenol, 3-[(4-hydroxy-phenyl)amino]benzonitrile, 4-[(3-methoxyphenyl)amino]phenol, 4-[(3,5-difluorophenyl)-amino]phenol, 4-[(3-methylphenyl)amino]phenol, 4-[(4-hydroxyphenyl)amino]benzonitrile, 4-[(3-chlorophenyl)amino]phenol, 4-(pyrimidin-2-ylamino)phenol, 4-[(cyclobutyl-methyl)amino]phenol, 2-[(4-hydroxyphenyl)amino]benzonitrile, 4-{[(1-methyl-1H-pyrazol-4-yl)methyl]amino}phenol, 4-[(cyclopropylmethyl)amino]phenol, 4-{[(1-methyl-1H-pyrazol-3-yl)methyl]amino}phenol, 4-(but-2-yn-1-ylamino)phenol, 4-(pyrazin-2-yl-amino)phenol, 4-(pyridin-2-ylamino)phenol, 4-(pyridazin-3-ylamino)phenol, 4-(pyrimidin-5-ylamino)phenol, 4-(pyridin-3-ylamino)phenol, 4-[(3,5-difluoro-4-methoxyphenyl)-amino]phenol, 4-(pyridin-4-ylamino)phenol, 4-[(3-fluoro-4-methoxyphenyl)amino]phenol, 2-(phenylamino)pyrimidin-5-ol, 5-[(4-hydroxyphenyl)amino]-2-methoxybenzonitrile and 4-{[3-(trifluoromethyl)phenyl]amino}phenol.

The hydroxy function(s) of the secondary amines listed above is (are) protected beforehand by a suitable protecting group prior to any coupling to an acid derivative of the compound of formula (VII) as defined in the preceding general process.

EXAMPLE 1

4-[{[3-(6-{[(3S)-3-(Morpholin-4-ylmethyl)-3,4-dihydroisoquinolin-2(1H)-yl]carbonyl}-1,3-benzodioxol-5-yl)-5,6,7,8-tetrahydroindolizin-1-yl]carbonyl}(phenyl)amino]phenyl disodium phosphate Step A: Methyl 3-{6-[((3S)-3-(4-morpholinylmethyl)-3,4-dihydro-2(1H)-isoquinolinyl)-carbonyl]-1,3-benzodioxol-5-yl}-5,6,7,8-tetrahydro-1-indolizinecarboxylate To a solution of 2 g of the compound of Preparation 1 (5.83 mmol) in 20 mL of dichloromethane there are added, at ambient temperature, 5.5 mL of N,N,N-triethylamine (6.96 mmol), 2.12 g of the compound of Preparation 1' (6.96 mmol), and then 0.94 g of hydroxybenzotriazole (HOBT) and 1.34 g of 1-ethyl-3-(3'-dimethylaminopropyl)-carbodiimide (EDC) (6.96 mmol). The reaction mixture is then stirred at ambient temperature overnight and then it is poured into saturated aqueous ammonium chloride solution and extracted with ethyl acetate. The organic phase is then dried over magnesium sulphate and then filtered and evaporated to dryness. The crude product thereby obtained is then purified by chromatography over silica gel (heptane/AcOEt gradient). The title product is obtained in the form of an oil.

$^1$H NMR: δ (500 MHz; dmso-d6; 300° K): 7.2-6.9 (m, 4H, aromatic Hs); 7.04-7.03-7.00 (m, 1H, aromatic H); 6.85 (m, 1H, aromatic H); 6.35-6.26-6.06 (m, 1H, H tetrahydroindolizine); 6.15-6.12 (m, 2H, H methylenedioxy); 5.06-4.84 (m, 1H, H dihydroisoquinoline); 4.86-4.17 (m, 2H, H dihydroisoquinoline); 3.65-3.6-3.55 (m, 3H, H methyl ester); 3.43-4.26 (m, 2H, H tetrahydroindolizine); 3.58-3.5 (m, 4H, H morpholine); 2.37-3.05 (m, 4H, 2H dihydroisoquinoline, 2H tetrahydroindolizine); 1.68-2.56 (m, 4H, H morpholine); 1.4-2.0 (m, 4H, H tetrahydroindolizine)

IR: ν: >C=O 1695 cm$^{-1}$ ester; ν: >C=O 1625 cm$^{-1}$ amide; ν: >C—O—C<1214-1176-1115 cm$^{-1}$; >CH—Ar 772-744 cm$^{-1}$ Step B: Lithium 3-[6-[(3S)-3-(morpholinomethyl)-3,4-dihydro-1H-isoquinoline-2-carbonyl]-1,3-benzodioxol-5-yl]-5,6,7,8-tetrahydro-1-indolizine-carboxylate To a solution of 4.6 g of the compound of Step A (8.26 mmol) in 24 mL of dioxane there is added a solution of lithium hydroxide (675 mg, 16.1 mmol). The batch is placed in a microwave oven at 140 W, 100° C. for a period of 2 hours 30 minutes. The reaction mixture is then filtered and evaporated. The solid thereby obtained is dried at 40° C. in an oven in the presence of P$_2$O$_5$.

$^1$H NMR: δ (400 MHz; dmso-d6; 353° K): 6.7-7.15 (unresolved peak, 6H, aromatic Hs); 6.21 (s, 1H, aromatic H); 6.03 (s, 2H, H methylenedioxy); 4.0-5.0 (unresolved peak, 3H dihydroisoquinoline); 3.4-3.6 (unresolved peak, 3H tetrahydroindolizine, 3H morpholine); 2.5-3.1 (unresolved peak, 4H, 2H tetrahydroindolizine, 2H morpholine); 1.5-2.4 (unresolved peak, 10H morpholine)

IR: ν:>C=O broad 1567 cm$^{-1}$ acetate; ν: 1236 cm$^{-1}$

Step C: N-(4-{[tert-Butyl(dimethyl)silyl]oxy}phenyl)-3-{6-[((3S)-3-(4-morpholinyl-methyl)-3,4-dihydro-2(1H)-isoquinolinyl)carbonyl]-1,3-benzodioxol-5-yl}-N-phenyl-5,6,7,8-tetrahydro-1-indolizine carboxamide To a solution of 2.6 g of the compound of Step B (4.73 mmol) in 47 mL of dichloromethane there are added, dropwise, 1.2 mL of oxalyl chloride (14.2 mmol) at 0° C. The reaction mixture is stirred at ambient temperature for 11 hours and then co-evaporated several times with dichloromethane. The product thereby obtained is suspended in 37 mL of dichloromethane, and is then added to a solution of 2.1 g of the compound obtained in Preparation 1" (7.1 mmol) in 10 mL of dichloromethane in the presence of 0.6 mL of pyridine (7.1 mmol). The batch is stirred at ambient temperature overnight.

The reaction mixture is concentrated and purified by chromatography over silica gel (dichloromethane/methanol gradient). The title product is obtained in the form of a foam.

¹H NMR: δ (500 MHz; dmso-d6; 300° K): 6.9-7.3 (9H, aromatic Hs); 6.88 (2H, aromatic Hs); 6.72-6.87 (2H, aromatic Hs); 6.64 (2H, aromatic Hs); 6.13 (2H methylenedioxy); 5.05-4.74 (1H dihydroisoquinoline); 4.25-4.13 (2H dihydroisoquinoline); 3.44-3.7 (4H morpholine); 3.62-3.52 (2H tetrahydroindolizine); 3.0-2.6 (4H, 2H tetrahydroindolizine, 2H dihydroisoquinoline); 2.54-1.94 (6H morpholine); 1.91-1.53 (4H tetrahydroindolizine); 0.92 (9H tert-butyl); 0.17 (6H dimethyl)

IR: ν:>C=O: 1632 $cm^{-1}$; ν: >C—O—C<: 1237 $cm^{-1}$; ν: —Si—O—C—: 1035 $cm^{-1}$; —Si—C—: 910 $cm^{-1}$; >CH—Ar: 806 $cm^{-1}$

Step D: N-(4-Hydroxyphenyl)-3-{6-[((3S)-3-(4-morpholinylmethyl)-3,4-dihydro-2(1H)-isoquinolinyl)carbonyl]-1,3-benzodioxol-5-yl}-N-phenyl-5,6,7,8-tetrahydro-1-indolizine carboxamide hydrochloride To a solution of 1.9 g of the compound obtained in Step C (2.3 mmol) in 4 mL of methanol there is added 0.646 g (11.5 mmol) of potassium hydroxide dissolved in 8 mL of methanol. The batch is stirred at ambient temperature for 30 minutes. The reaction mixture is then diluted with dichloromethane and washed successively with 1M HCl solution, saturated aqueous $NaHCO_3$ solution and then brine until a neutral pH is reached. The organic phase is then dried over magnesium sulphate, filtered and evaporated. The crude product thereby obtained is purified by chromatography over silica gel (dichloromethane/methanol gradient). The solid is then dissolved in dichloromethane, and 2 mL of 1M ethereal HCl are added. The batch is stirred for 1 hour and then evaporated to dryness. The hydrochloride thereby obtained is dissolved in a mixture of water/acetonitrile until dissolution is complete, and is then lyophilised.

Elemental Microanalysis: (%, Theoretical:Measured)
% C=69.11:68.95; % H=5.8:5.46; % N=7.5:7.51; % Cl–=4.74:4.48

Optical rotation: $(α)_D^{20}$=+50.8° (c=9 mg/mL, MeOH)

Step E: 4-[{[3-(6-{[(3S)-3-(Morpholin-4-ylmethyl)-3,4-dihydroisoquinolin-2(1H)-yl]-carbonyl}-1,3-benzodioxol-5-yl)-5,6,7,8-tetrahydroindolizin-1-yl]carbonyl}(phenyl)-amino]phenyl dibenzyl phosphate To a suspension of 82 mg of sodium hydride (2.06 mmol) in 10 mL of anhydrous THF there are added, in portions and at 0° C., 700 mg of the compound of Step D. After stirring for 30 minutes at 0° C. and for 30 minutes at ambient temperature, tetrabenzyl pyrophosphate is added at 0° C. and the reaction mixture is stirred overnight at ambient temperature. After evaporating off the solvent, the crude reaction product is diluted with dichloromethane (30 mL), washed with saturated aqueous $NaHCO_3$ solution and then with brine. The organic phase is then dried over $MgSO_4$, filtered, concentrated to dryness and purified by chromatography over silica gel (gradient $CH_2Cl_2$/MeOH). The title product is then obtained in the form of a solid.

¹H NMR: δ (500 MHz; DMSO-d6; 300K): 7.34 (m, 10H, phenyl); 7.30-6.71 (m, 15H, aryl); 6.06 (s, 1H, methylenedioxy); 5.30-4.97 (m, 1H, pyrrole); 5.11 (m, 4H, benzyl): 5.03-3.64 (m, 1H, tertiary C THIQ); 4.91-4.09 (m, 2H, secondary C THIQ); 3.99-3.48 (m, 2H, secondary C THIQ); 3.54-3.44 (m, 4H, morpholine); 2.89-2.65 (m, 3H, secondary C THIQ); 2.51-1.87 (m, 4H, secondary C THID); 2.36-1.85 (m, 2H, secondary C THIQ); 1.91-1.45 (m, 4H, secondary C THID)

Step F: 4-[{[3-(6-{[(3S)-3-(Morpholin-4-ylmethyl)-3,4-dihydroisoquinolin-2(1H)-yl]-carbonyl}-1,3-benzodioxol-5-yl)-5,6,7,8-tetrahydroindolizin-1-yl]carbonyl}(phenyl)-amino]phenyl disodium phosphate 50 mg of $Pd(OH)_2$ are added to a solution of the product obtained in Step E (505 mg; 0.52 mmol) in methanol (10 mL), and then the reaction mixture is placed under a hydrogen atmosphere (1 bar) for 5 hours. After filtering off the catalyst and concentrating to dryness, the crude reaction product is dissolved in methanol (5 mL) and treated with 0.95 mL of 1M sodium hydroxide solution. The solvents are then evaporated off and the crude reaction product is purified by chromatography over an OASIS® phase (acetonitrile/$H_2O$ gradient) to obtain a white solid.

Elemental Microanalysis:

|  | % C | % H | % N | % Na |
| --- | --- | --- | --- | --- |
| Calculated | 61.87 | 4.95 | 6.71 | 5.51 |
| Found | 61.45 | 4.46 | 6.61 | 5.38 |

IR: ν: —C=O: 1628 $cm^{-1}$; ν: C—O—C: 1234 $cm^{-1}$; ν: P=O: 115 $cm^{-1}$; ν: P—O: 985 $cm^{-1}$;
ν: CH—Ar: 876 $cm^{-1}$

High-Resolution Mass Spectrometry (ESI+):
Empirical formula: $C_{43}H_{41}N_4Na_2O_9P$
[M+H]+ calculated: 835.2479
[M+H]+ measured: 835.2467

EXAMPLE 2

4-[{[3-(6-{[(3R)-3-Methyl-3,4-dihydroisoquinolin-2(1H)-yl]carbonyl}-1,3-benzodioxol-5-yl)-5,6,7,8-tetrahydroindolizin-1-yl]carbonyl}(phenyl)amino]-phenyl disodium phosphate Step A: N-(4-Hydroxyphenyl)-3-(6-{[(3R)-3-methyl-3,4-dihydroisoquinolin-2(1H)-yl]carbonyl}-1,3-benzodioxol-5-yl)-N-phenyl-5,6,7,8-tetrahydroindolizine-1-carboxamide The procedure is in accordance with a protocol analogous to that described in Steps A-D of Example 1 replacing the product of Preparation 1' in Step A by that of Preparation 2', it being understood that the product thereby obtained is not subjected to a step of conversion into salt form in the presence of HCl in ether.

Elemental Microanalysis: (%, Theoretical:Measured)
% C=74.86:74.88; % H=5.64:5.31; % N=6.72:6.78

Step B: 4-[{[3-(6-{[(3R)-3-Methyl-3,4-dihydroisoquinolin-2(1H)-yl]carbonyl}-1,3-benzodioxol-5-yl)-5,6,7,8-tetrahydroindolizin-1-yl]carbonyl}(phenyl)amino]phenyl disodium phosphate The procedure is in accordance with a protocol analogous to that described in Steps E and F of Example 1.

High-Resolution Mass Spectrometry (ESI+):
Empirical formula: $C_{39}H_{36}N_3O_8P$
[M+H]+ calculated: 706.2313
[M+H]+ measured: 706.2324

EXAMPLE 3

4-[(1-Methyl-1H-indol-5-yl){[3-(2-{[(3S)-3-(morpholin-4-ylmethyl)-3,4-dihydroisoquinolin-2(1H)-yl]carbonyl}phenyl)-5,6,7,8-tetrahydroindolizin-1-yl]-carbonyl}amino]phenyl disodium phosphate Step A: 3-{5-Chloro-2-[((3S)-3-(4-morpholinylmethyl)-3,4-dihydro-2(1H)-isoquinolinyl)-carbonyl]phenyl}-N-(4-hydroxyphenyl)-N-(1-methyl-1H-indol-5-yl)-5,6,7,8-tetrahydro-1-indolizine carboxamide hydrochloride The procedure is in accordance with a protocol analogous to that described in Steps A-D of Example 1 replacing, on the one hand, the compound of Preparation 1 used in Step A by the compound of Preparation 2 and, on the other hand, the compound of Preparation 1" used in Step C by that of Preparation 2".

Elemental Microanalysis:

|  | % C | % H | % N | % Cl⁻ |
|---|---|---|---|---|
| Calculated | 68.04 | 5.72 | 8.82 | 4.91 |
| Found | 67.84 | 5.46 | 8.64 | 5.21 |

Optical rotation: $(\alpha)_D^{20}$=+55.9° (c=7 mg/mL, MeOH)

Step B: 4-[(1-Methyl-1H-indol-5-yl){[3-(2-{[(3S)-3-(morpholin-4-ylmethyl)-3,4-dihydroisoquinolin-2(1H)-yl]carbonyl}phenyl)-5,6,7,8-tetrahydroindolizin-1-yl]-carbonyl}amino]phenyl disodium phosphate The procedure is in accordance with a protocol analogous to that described in Steps E and F of Example 1.
High-Resolution Mass Spectrometry (ESI+):
Empirical formula: $C_{45}H_{44}N_5Na_2O_7P$
[M−2Na+3H]⁺ calculated: 800.3208 [M−2Na+3H]+ measured: 800.3211

EXAMPLE 4

4-[{[3-(6-{[(3R)-3-Methyl-3,4-dihydroisoquinolin-2(1H)-yl]carbonyl}-1,3-benzodioxol-5-yl)indolizin-1-yl]carbonyl}(1-methyl-1H-pyrrolo[2,3-b]pyridin-5-yl)amino]phenyl disodium phosphate Step A: N-(4-Hydroxyphenyl)-3-(6-{[(3R)-3-methyl-3,4-dihydroisoquinolin-2(1H)-yl]-carbonyl}-1,3-benzodioxol-5-yl)-N-(1-methyl-1H-pyrrolo[2,3-b]pyridin-5-yl)-indolizine-1-carboxamide hydrochloride The procedure is in accordance with a protocol analogous to that described in Steps A-D of Example 1 replacing, on the one hand, the compounds of Preparations 1 and 1' used in Step A by the compounds of Preparations 3 and 2' and, on the other hand, the compound of Preparation 1" used in Step C by that of Preparation 3".
Elemental Microanalysis: (%, Theoretical:Measured)
% C=69.14:70.09; % H=4.81:4.55; % N=9.83:10.09; % Cl−=4.98:3.26

Step B: 4-[{[3-(6-{[(3R)-3-Methyl-3,4-dihydroisoquinolin-2(1H)-yl]carbonyl}-1,3-benzodioxol-5-yl)indolizin-1-yl]carbonyl}(1-methyl-1H-pyrrolo[2,3-b]pyridin-5-yl)-amino]phenyl diethyl phosphate To a suspension of the compound obtained in Step A (1.5 mmol) in 10 mL of anhydrous $CH_2Cl_2$ there are added triethylamine (0.42 mL; 3 mmol), and then diethyl cyanophosphonate (0.24 mL; 1.65 mmol) dropwise at ambient temperature. After stirring overnight at ambient temperature, the reaction mixture is diluted with $CH_2Cl_2$, washed with saturated aqueous $NaHCO_3$ solution and then with brine. The organic phase is then dried over $MgSO_4$, filtered, concentrated to dryness and purified by chromatography over silica gel ($CH_2Cl_2$/MeOH gradient). The title product is then obtained in the form of a solid.

Step C: 4-[{[3-(6-{[(3R)-3-Methyl-3,4-dihydroisoquinolin-2(1H)-yl]carbonyl}-1,3-benzodioxol-5-yl)indolizin-1-yl]carbonyl}(1-methyl-1H-pyrrolo[2,3-b]pyridin-5-yl)amino]-phenyl disodium phosphate 0.4 mL of trimethylsilyl bromide (3 mmol) is added dropwise at ambient temperature to a solution of the product obtained in Step B (0.78 mmol) in $CH_2Cl_2$(12 mL). The reaction mixture is stirred for 5 hours, and then a solution of $Na_2CO_3$ (580 mg) in water (4 mL) is slowly added at 0° C. After stirring for 30 minutes, the reaction mixture is concentrated to dryness, diluted with anhydrous methanol (25 mL) and microfiltered. The filtrate is dried and purified by chromatography over an OASIS® phase (acetonitrile/$H_2O$ gradient).
High-Resolution Mass Spectrometry (ESI+):
Empirical formula: $C_{45}H_{44}N_5Na_2O_7P$
[M−2Na+3H]⁺ calculated: 800.3211
[M−2Na+3H]+ measured: 800.3201

EXAMPLE 5

4-[{[3-(6-{[(3R)-3-Methyl-3,4-dihydroisoquinolin-2(1H)-yl]carbonyl}-1,3-benzodioxol-5-yl)indolizin-1-yl]carbonyl}(pyridin-4-yl)amino]phenyl disodium phosphate Step A: N-(4-Hydroxyphenyl)-3-(6-{[(3R)-3-methyl-3,4-dihydroisoquinolin-2(1H)-yl]-carbonyl}-1,3-benzodioxol-5-yl)-N-(pyridin-4-yl)indolizine-1-carboxamide hydrochloride The procedure is in accordance with a protocol analogous to that described in Steps A-D of Example 1 replacing, on the one hand, the compounds of Preparations 1 and 1' used in Step A by the compounds of Preparations 3 and 2' and, on the other hand, the compound of Preparation 1" used in Step C by that of Preparation 4".
Elemental Microanalysis: (%, Theoretical:Measured)
% C=69.24:69.12; % H=4.74:4.23; % N=8.5:8.45; % Cl−=5.38:5.2

Step B: 4-[{[3-(6-{[(3R)-3-Methyl-3,4-dihydroisoquinolin-2(1H)-yl]carbonyl}-1,3-benzodioxol-5-yl)indolizin-1-yl]carbonyl}(pyridin-4-yl)amino]phenyl diethyl phosphate To a suspension of 950 mg of the compound obtained in Step A (1.5 mmol) in 10 mL of anhydrous $CH_2Cl_2$ there are added triethylamine (0.42 mL; 3 mmol), and then diethyl cyanophosphonate (0.24 mL; 1.65 mmol) dropwise at ambient temperature. After stirring overnight at ambient temperature, the reaction mixture is diluted with $CH_2Cl_2$, washed with saturated aqueous $NaHCO_3$ solution and then with brine. The organic phase is then dried over $MgSO_4$, filtered, concentrated to dryness and purified by chromatography over silica gel ($CH_2Cl_2$/MeOH gradient). The title product is then obtained in the form of a solid.
$^1$H NMR: δ (500 MHz; DMSO-d6; 300K): 8.5-8.0 (m, 5H); 7.2-7.1 (m, 1H); 6.85-6.65 (m, 1H); 7.3-6.8 (m, 10H); 6.25-6.10 (bs, 1H); 6.2 (bs, 2H); 5.1-3.7 (6d, 2H); 4.7-3.8 (m, 1H); 4.15 (m, 4H); 3.0-1.7 (m, 2H); 1.25 (m, 6H); 0.85-0.24 (m, 3H)

Step C: 4-[{[3-(6-{[(3R)-3-Methyl-3,4-dihydroisoquinolin-2(1H)-yl]carbonyl}-1,3-benzodioxol-5-yl)indolizin-1-yl]carbonyl}(pyridin-4-yl)amino]phenyl disodium phosphate 0.4 mL of trimethylsilyl bromide (3 mmol) is added dropwise at ambient temperature to a solution of the product obtained in Step B (591 mg; 0.78 mmol) in $CH_2Cl_2$ (12 mL). The reaction mixture is stirred for 5 hours, and then a solution of $Na_2CO_3$ (580 mg) in water (4 mL) is slowly added at 0° C. After stirring for 30 minutes, the reaction mixture is concentrated to dryness, diluted with anhydrous methanol (25 mL) and microfiltered. The filtrate is dried and purified by chromatography over an OASIS® phase (acetonitrile/$H_2O$ gradient).
$^1$H NMR: δ (500 MHz; $D_2O$; 300K): 8.23-7.98 (m, 2H, pyridyl); 7.01-6.97 (m, 2H, pyridyl); 7.88-7.80 (m, 1H, indolizine); 7.18-6.57 (m, 13H, aromatic Hs THIQ+aryl+ indolizine+phenol); 6.17-6.15 (m, 1H, indolizine): 5.96 (m, 2H, methylenedioxy); 4.61-3.76 (m, 1H, ternary C THIQ); 4.16 (m, 2H, secondary C THIQ); 2.86-2.31 (m, 2H, secondary C THIQ); 0.94-0.76 (m, 3H, primary C THIQ)
IR: ν: —C=O: 1620 $cm^{-1}$; ν: C—O—C: 1218 $cm^{-1}$; ν: P=O: 1107 $cm^{-1}$ ν: P—O: 981 $cm^{-1}$ ν: CH—Ar: 881-741 $cm^{-1}$
High-Resolution Mass Spectrometry (ESI+):
Empirical formula: $C_{38}H_{29}N_4Na_2O_8P$
$[M-2Na+3H]^+$ calculated: 703.1952
$[M-2Na+3H]^+$ measured: 703.1951

EXAMPLE 6

4-[{[3-(6-{[(3S)-3-(Morpholin-4-ylmethyl)-3,4-dihydroisoquinolin-2(1H)-yl]carbonyl}-1,3-benzodioxol-5-yl)-5,6,7,8-tetrahydroindolizin-1-yl]carbonyl}(phenyl)amino]phenyl dibenzyl phosphate The procedure is in accordance with the protocol described in Steps A-E of Example 1.
$^1$H NMR: δ (500 MHz; DMSO-d6; 300K): 7.34 (m, 10H, phenyl); 7.30-6.71 (m, 15H, aryl); 6.06 (s, 1H, methylenedioxy); 5.30-4.97 (m, 1H, pyrrole); 5.11 (m, 4H, benzyl): 5.03-3.64 (m, 1H, tertiary C THIQ); 4.91-4.09 (m, 2H, secondary C THIQ); 3.99-3.48 (m, 2H, secondary C THIQ); 3.54-3.44 (m, 4H, morpholine); 2.89-2.65 (m, 3H, secondary C THIQ); 2.51-1.87 (m, 4H, secondary C THID); 2.36-1.85 (m, 2H, secondary C THIQ); 1.91-1.45 (m, 4H, secondary C THID)

EXAMPLE 7

Diethyl 4-[{[3-(6-{[(3R)-3-methyl-3,4-dihydroisoquinolin-2(1H)-yl]-carbonyl}-1,3-benzodioxol-5-yl)indolizin-1-yl]carbonyl}(pyridin-4-yl)amino]phenyl phosphate The procedure is in accordance with the protocol described in Steps A and B of Example 5.
$^1$H NMR: δ (500 MHz; DMSO-d6; 300K): 8.5-8.0 (m, 5H); 7.2-7.1 (m, 1H); 6.85-6.65 (m, 1H); 7.3-6.8 (m, 10H); 6.25-6.10 (bs, 1H); 6.2 (bs, 2H); 5.1-3.7 (6d, 2H); 4.7-3.8 (m, 1H); 4.15 (m, 4H); 3.0-1.7 (m, 2H); 1.25 (m, 6H); 0.85-0.24 (m, 3H)

EXAMPLE 8

4-[{[3-(6-{[(3S)-3-(Morpholin-4-ylmethyl)-3,4-dihydroisoquinolin-2(1H)-yl]carbonyl}-1,3-benzodioxol-5-yl)-5,6,7,8-tetrahydroindolizin-1-yl]carbonyl}-(phenyl)amino]phenyl dihydrogen phosphate hydrochloride 100 mg of $Pd(OH)_2$ are added to a solution of the product obtained in Step E of Example 1 (500 mg; 0.51 mmol) in methanol (10 mL), and then the reaction mixture is placed under a hydrogen atmosphere (1 bar) for 5 hours. After filtering off the catalyst and concentrating to dryness, the crude reaction product is immediately purified by chromatography over a C18 phase (acetonitrile/$H_2O$+0.2% HCl gradient) to obtain a solid.
High-Resolution Mass Spectrometry (ESI+):
Empirical formula: $C_{43}H_{43}N_4O_9P$
$[M+H]^+$ calculated: 791.2846
$[M+H]^+$ measured: 791.2852

EXAMPLE 9

4-[{[5-(5-Chloro-2-{[(3R)-3-methyl-3,4-dihydroisoquinolin-2(1H)-yl]-carbonyl}phenyl)-1,2-dimethyl-1H-pyrrol-3-yl]carbonyl}(pyridin-4-yl)amino]phenyl disodium phosphate Step A: 5-(5-Chloro-2-{[(3R)-3-methyl-3,4-dihydroisoquinolin-2(1H)-yl]carbonyl}-phenyl)-N-(4-hydroxyphenyl)-1,2-dimethyl-N-(pyridin-4-yl)-1H-pyrrole-3-carboxamide hydrochloride The procedure is in accordance with a protocol analogous to that described in Steps A-D of Example 1 replacing, on the one hand, the compounds of Preparations 1 and 1' used in Step A by the compounds of Preparations 4 and 2' and, on the other hand, the compound of Preparation 1" used in Step C by that of Preparation 4".
Elemental Microanalysis: (%, Theoretical:Measured)
% C=66.99:66.88; % H=5.14:5.28; % N=8.93:8.87; % Cl-=5.65:4.98 High-resolution mass spectrometry (ESI+):
Empirical formula: $C_{35}H_{32}ClN_4O_3$
$[M+H]^+$ calculated: 591.2157
$[M+H]^+$ measured: 591.2178

Step B: 4-[[{5-(5-Chloro-2-{[(3R)-3-methyl-3,4-dihydroisoquinolin-2(1H)-yl]carbonyl}-phenyl)-1,2-dimethyl-1H-pyrrol-3-yl]carbonyl}(pyridin-4-yl)amino]phenyl disodium phosphate The procedure is in accordance with a protocol analogous to that described in Steps B and C of Example 4.

EXAMPLE 10

4-[{[1,2-Dimethyl-5-(6-{[(3S)-3-(morpholin-4-ylmethyl)-3,4-dihydroisoquinolin-2(1H)-yl]carbonyl}-1,3-benzodioxol-5-yl)-1H-pyrrol-3-yl]carbonyl}(1-methyl-1H-pyrrolo[2,3-b]pyridin-5-yl)amino]phenyl disodium phosphate Step A: N-(4-Hydroxyphenyl)-1,2-dimethyl-N-(1-methyl-1H-pyrrolo[2,3-b]pyridin-5-yl)-5-(6-{[(3S)-3-(morpholin-4-ylmethyl)-3,4-dihydroisoquinolin-2(1H)-yl]carbonyl}-1,3-benzodioxol-5-yl)-1H-pyrrole-3-carboxamide hydrochloride The procedure is in accordance with a protocol analogous to that described in Steps A-D of Example 1 replacing, on the one hand, the compound of Preparation 1 used in Step A by the compound of Preparation 5 and, on the other hand, the compound of Preparation 1" used in Step C by that of Preparation 3".
Elemental Microanalysis: (%, Measured(Theoretical))
%C=66.41(66.62);% H=5.08(5.59);% N=10.85(10.84);% Cl−=4.68(4.57)

Step B: 4-[{[1,2-Dimethyl-5-(6-{[(3S)-3-(morpholin-4-ylmethyl)-3,4-dihydroisoquinolin-2(1H)-yl]carbonyl}-1,3-benzodioxol-5-yl)-1H-pyrrol-3-yl]carbonyl}(1-methyl-1H-pyrrolo[2,3-b]pyridin-5-yl)amino]phenyl disodium phosphate The procedure is in accordance with a protocol analogous to that described in Steps B and C of Example 4.

EXAMPLE 11

4-[{[1,2-Dimethyl-5-(6-{[(3S)-3-(morpholin-4-ylmethyl)-3,4-dihydroisoquinolin-2(1H)-yl]carbonyl}-1,3-benzodioxol-5-yl)-1H-pyrrol-3-yl]carbonyl}(1-methyl-1H-pyrazol-4-yl)amino]phenyl disodium phosphate Step A: N-(4-Hydroxyphenyl)-1,2-dimethyl-N-(1-methyl-1H-pyrazol-4-yl)-5-(6-{[(3S)-3-(morpholin-4-ylmethyl)-3,4-dihydroisoquinolin-2(1H)-yl]carbonyl}-1,3-benzodioxol-5-yl)-1H-pyrrole-3-carboxamide hydrochloride The procedure is in accordance with a protocol analogous to that described in Steps A-D of Example 1 replacing, on the one hand, the compound of Preparation 1 used in Step A by the compound of Preparation 5 and, on the other hand, the compound of Preparation 1" used in Step C by that of Preparation 5".
Elemental Microanalysis: (%, Measured(Theoretical))
% C=64.25(64.59);% H=5.4(5.7);% N=11.41(11.59); % Cl−=4.93(4.89)

Step B: 4-[{[1,2-Dimethyl-5-(6-{[(3S)-3-(morpholin-4-ylmethyl)-3,4-dihydroisoquinolin-2(1H)-yl]carbonyl}-1,3-benzodioxol-5-yl)-1H-pyrrol-3-yl]carbonyl}(1-methyl-1H-pyrazol-4-yl)amino]phenyl disodium phosphate The procedure is in accordance with a protocol analogous to that described in Steps E and F of Example 1.
IR (cm$^{-1}$): ν: C=O: 1628; ν: (phosphate; ether): 1238, 1143, 1113, 985; γ: >CH Ar: 740
Elemental Microanalysis:

|  | % C | % H | % N |
|---|---|---|---|
| Calculated | 57.64 | 4.84 | 10.34 |
| Found | 56.62 | 4.54 | 10.14 |

High-Resolution Mass Spectrometry (ESI+−/FIA/HR):
Empirical formula: $C_{39}H_{39}ClN_6Na_2O_9P$
[M−Na+H]$^+$ calculated: 791.2565
[M−Na+H]$^+$ measured: 791.2564

EXAMPLE 12

4-[{[1,2-Dimethyl-5-(6-{[(3R)-3-[3-(morpholin-4-yl)propyl]-3,4-dihydro-isoquinolin-2(1H)-yl]carbonyl}-1,3-benzodioxol-5-yl)-1H-pyrrol-3-yl]carbonyl}(1-methyl-1H-pyrrolo[2,3-b]pyridin-5-yl)amino]phenyl disodium phosphate Step A: N-(4-Hydroxyphenyl)-1,2-dimethyl-N-(1-methyl-1H-pyrrolo[2,3-b]pyridin-5-yl)-5-(6-{[(3R)-3-[3-(morpholin-4-yl)propyl]-3,4-dihydroisoquinolin-2(1H)-yl]carbonyl}-1,3-benzodioxol-5-yl)-1H-pyrrole-3-carboxamide hydrochloride The procedure is in accordance with a protocol analogous to that described in Steps A-D of Example 1 replacing, on the one hand, the compounds of Preparations 1 and 1' used in Step A by the compounds of Preparations 5 and 3' and, on the other hand, the compound of Preparation 1" used in Step C by that of Preparation 3".
Elemental Microanalysis: (%, Measured(Theoretical))
% C=67.63(68.06);% H=5.27(5.95);% N=10.08(10.13);% Cl−=4.53(4.27)
High-Resolution Mass Spectrometry (ESI+):
Empirical formula: $C_{35}H_{32}ClN_4O_3$
[M+H]$^+$ calculated: 793.3708
[M+H]$^+$ measured: 793.3704

Step B: 4-[{[1,2-Dimethyl-5-(6-{[(3R)-3-[3-(morpholin-4-yl)propyl]-3,4-dihydroisoquinolin-2(1H)-yl]carbonyl}-1,3-benzodioxol-5-yl)-1H-pyrrol-3-yl]carbonyl}(1-methyl-1H-pyrrolo[2,3-b]pyridin-5-yl)amino]phenyl disodium phosphate The procedure is in accordance with a protocol analogous to that described in Steps E and F of Example 1.
Unless otherwise mentioned, the compounds of the following Examples are synthesised in accordance with the process of Example 1 using: (i) the appropriate acid obtained according to one of Preparations 1 to 9 and (ii) the appropriate tetrahydroisoquinoline compound obtained according to one of Preparations 1' to 4' and, in Step C: (iii) the suitable NHR$_3$R$_4$ amine (a non-exhaustive list is proposed in Preparations 1" to 8").

EXAMPLE 13

4-[{[5-(5-Chloro-2-{[(3S)-3-(morpholin-4-ylmethyl)-3,4-dihydroisoquinolin-2(1H)-yl]carbonyl}phenyl)-1,2-dimethyl-1H-pyrrol-3-yl]carbonyl}(pyridin-4-yl)amino]phenyl disodium phosphate Step A: 5-(5-Chloro-2-{[(3S)-3-(morpholin-4-ylmethyl)-3,4-dihydroisoquinolin-2(1H)-yl]carbonyl}phenyl)-N-(4-hydroxyphenyl)-1,2-dimethyl-N-(pyridin-4-yl)-1H-pyrrole-3-carboxamide hydrochloride The procedure is in accordance with a protocol analogous to that described in Steps A-D of Example 1 replacing, on the one hand, the compound of Preparation 1 used in Step A by the compound of Preparation 4 and, on the other hand, the compound of Preparation 1" used in Step C by that of Preparation 4". The product obtained is finally subjected to a step of conversion into salt form in the presence of 1M HCl in ether.

After filtration and lyophilisation in a mixture of acetonitrile/water, the expected compound is obtained.
High-Resolution Mass Spectrometry (ESI+):
  Empirical formula: $C_{39}H_{38}ClN_5O_4$
  $[M+H]^+$ calculated: 676.2685
  $[M+H]^+$ measured: 676.2684

Step B: 4-[{[5-(5-Chloro-2-{[(3S)-3-(morpholin-4-ylmethyl)-3,4-dihydroisoquinolin-2(1H)-yl]carbonyl}phenyl)-1,2-dimethyl-1H-pyrrol-3-yl]carbonyl}(pyridin-4-yl)amino]-phenyl disodium phosphate The procedure is in accordance with a protocol analogous to that described in Steps B and C of Example 16.
$^{31}$P NMR (500 MHz, $D_2O$) δ ppm: −0.05
IR ($cm^{-1}$): ν: C=O: 1631; ν: (phosphate; ether): 1243, 1136, 1112, 982; γ: >CH Ar: 883, 745
Elemental Microanalysis:

|  | % C | % H | % N |
|---|---|---|---|
| Calculated | 58.54 | 4.66 | 8.75 |
| Found | 58.23 | 4.51 | 8.76 |

High-Resolution Mass Spectrometry (ESI+):
  Empirical formula: $C_{39}H_{37}ClN_5Na_2O_7P$
  $[M-Na+2H]^+$ calculated: 778.2168
  $[M-Na+2H]^+$ measured: 778.2169

EXAMPLE 14

4-[{[5-(5-Fluoro-4-methoxy-2-{[(3S)-3-(morpholin-4-ylmethyl)-3,4-dihydroisoquinolin-2(1H)-yl]carbonyl}phenyl)-1,2-dimethyl-1H-pyrrol-3-yl]-carbonyl}(1-methyl-1H-pyrazol-4-yl)amino]phenyl disodium phosphate

EXAMPLE 15

4-[{[5-(5-Fluoro-2-{[(3S)-3-(morpholin-4-ylmethyl)-3,4-dihydroisoquinolin-2(1H)-yl]carbonyl}phenyl)-1,2-dimethyl-1H-pyrrol-3-yl]carbonyl}(1-methyl-1H-pyrazol-4-yl)amino]phenyl disodium phosphate Step A: 5-(5-Fluoro-2-{[(3S)-3-(morpholin-4-ylmethyl)-3,4-dihydroisoquinolin-2(1H)-yl]carbonyl}phenyl)-N-(4-hydroxyphenyl)-1,2-dimethyl-N-(1-methyl-1H-pyrazol-4-yl)-1H-pyrrole-3-carboxamide hydrochloride The procedure is in accordance with a protocol analogous to that described in Steps A-D of Example 1 replacing, on the one hand, the compound of Preparation 1 used in Step A by the compound of Preparation 7 and, on the other hand, the compound of Preparation 1" used in Step C by that of Preparation 5". The product obtained is finally subjected to a step of conversion into salt form in the presence of HCl in ether. After filtration and lyophilisation in a mixture of acetonitrile/water, the expected compound is obtained.
Elemental Microanalysis: (%, Measured (Theoretical))
  % C=65.69(65.28);% H=5.38(5.77);% N=11.18(12.02); % Cl−=5.61(5.07)

Step B: 4-[{[5-(5-Fluoro-2-{[(3S)-3-(morpholin-4-ylmethyl)-3,4-dihydroisoquinolin-2(1H)-yl]carbonyl}phenyl)-1,2-dimethyl-1H-pyrrol-3-yl]carbonyl}(1-methyl-1H-pyrazol-4-yl)amino]phenyl disodium phosphate The procedure is in accordance with a protocol analogous to that described in Steps B and C of Example 16.
$^{31}$P NMR (400/500 MHz, $CD_3OD$) δ ppm: −0.5
IR ($cm^{-1}$): ν: C=O: 1628; ν: (phosphate; ether): 1238, 1114, 983
Elemental Microanalysis:

|  | % C | % H | % N |
|---|---|---|---|
| Calculated | 58.02 | 4.87 | 10.68 |
| Found | 59.03 | 4.98 | 10.14 |

High-Resolution Mass Spectrometry (ESI+):
  Empirical formula: $C_{38}H_{38}FN_6Na_2O_7$
  $[M-2Na+3H]^+$ calculated: 743.2752
  $[M-2Na+3H]^+$ measured: 743.2760

EXAMPLE 16

4-[{[1,2-Dimethyl-5-(7-{[(3S)-3-(morpholin-4-ylmethyl)-3,4-dihydroisoquinolin-2(1H)-yl]carbonyl}-2,3-dihydro-1,4-benzodioxin-6-yl)-1H-pyrrol-3-yl]carbonyl}(1-methyl-1H-pyrazol-4-yl)amino]phenyl disodium phosphate Step A: N-(4-Hydroxyphenyl)-1,2-dimethyl-N-(1-methyl-1H-pyrazol-4-yl)-5-(7-{[(3S)-3-(morpholin-4-ylmethyl)-3,4-dihydroisoquinolin-2(1H)-yl]carbonyl}-2,3-dihydro-1,4-benzodioxin-6-yl)-1H-pyrrole-3-carboxamide hydrochloride The procedure is in accordance with a protocol analogous to that described in Steps A-D of Example 1 replacing, on the one hand, the compound of Preparation 1 used in Step A by the compound of Preparation 8 and, on the other hand, the compound of Preparation 1" used in Step C by that of Preparation 5". The product obtained is finally subjected to a step of conversion into salt form in the presence of 1M HCl in ether. After filtration and lyophilisation in a mixture of acetonitrile/water, the expected compound is obtained.
Elemental Microanalysis: (%, Theoretical:Measured)
  % C=64.99:64.67; % H=5.86:5.67; % N=11.37:11.27; % Cl−=4.8:4.71
High-Resolution Mass Spectrometry (ESI+):
  Empirical formula: $C_{40}H_{43}N_6O_{61}$
  $[M+H]^+$ calculated: 703.3236
  $[M+H]^+$ measured: 703.3239

Step B: 4[-{[1,2-Dimethyl-5-(7-{[(3S)-3-(morpholin-4-ylmethyl)-3,4-dihydroisoquinolin-2(1H)-yl]carbonyl}-2,3-dihydro-1,4-benzodioxin-6-yl)-1H-pyrrol-3-yl]carbonyl}(1-methyl-1H-pyrazol-4-yl)amino]phenyl N,N,N',N'-tetramethylphosphorodiamidate To a solution of 125 mg of the compound of Step A (0.18 mmol) in dichloromethane (6 mL) there are added 55 μL of diazabicyclo[5.4.0]undec-7-ene (DBU; 0.36 mmol), and then 33 μL of bisdimethylaminophosphoryl chloride (0.19 mmol) and 2 mg of dimethylamino-4-pyridine (0.02 mmol). The reaction mixture is stirred for 15 hours, diluted with dichloromethane and then with saturated aqueous sodium carbonate solution. The aqueous phase is extracted with dichloromethane; the organic phases are then combined, washed with water and with brine and dried over magnesium sulphate. After evaporating off the solvents, the crude reaction product is used directly in the next Step.

Step C: 4-[{[1,2-Dimethyl-5-(7-{[(3S)-3-(morpholin-4-ylmethyl)-3,4-dihydroisoquinolin-2(1H)-yl]carbonyl}-2,3-dihydro-1,4-benzodioxin-6-yl)-1H-pyrrol-3-yl]carbonyl}(1-methyl-1H-pyrazol-4-yl)amino]phenyl disodium phosphate 4 mL of trifluoroacetic acid are added dropwise to a solution of 125 mg of the compound of Step B (0.15 mmol) in a 1:1 mixture of acetonitrile and water (5 mL). After stirring for 20 hours at ambient temperature, the reaction mixture is evaporated to dryness, keeping the temperature of the water bath below 40° C., and then the residue is treated with a solution of sodium carbonate (95 mg; 0.9 mmol) in water (4 mL). After stirring for 2 hours at ambient temperature, the reaction mixture is evaporated to dryness and then 6 mL of anhydrous ethanol are added. The solid is filtered off, and the filtrate is concentrated to dryness, and then purified over an OASIS® phase (acetonitrile/water gradient).
$^{31}$P NMR (500 MHz, D$_2$O) δ ppm: 0.9
IR (cm$^{-1}$): ν: C=O: 1623; ν: (phosphate; ether): 1235, 1162, 1115, 1065, 985; γ: >CH Ar: 745
High-Resolution Mass Spectrometry (ESI+):
  Empirical formula: C$_{40}$H$_{41}$N$_6$Na$_2$O$_9$P
  [M−2Na+3H]$^+$ calculated: 783.2902
  [M−2Na+3H]$^+$ measured: 783.2907

EXAMPLE 17

5-[{[5-(5-Fluoro-2-{[(3S)-3-(morpholin-4-ylmethyl)-3,4-dihydroisoquinolin-2(1H)-yl]carbonyl}phenyl)-1,2-dimethyl-1H-pyrrol-3-yl]carbonyl}(pyridin-4-yl)amino]pyrimidin-2-yl disodium phosphate

EXAMPLE 18

5-[{[5-(5-Chloro-2-{[(3S)-3-(morpholin-4-ylmethyl)-3,4-dihydroisoquinolin-2(1H)-yl]carbonyl}phenyl)-1,2-dimethyl-1H-pyrrol-3-yl]carbonyl}(pyridin-4-yl)amino]pyrimidin-2-yl disodium phosphate

EXAMPLE 19

4-({[5-(5-Chloro-2-{[(3S)-3-(morpholin-4-ylmethyl)-3,4-dihydroisoquinolin-2(1H)-yl]carbonyl}phenyl)-1,2-dimethyl-1H-pyrrol-3-yl]carbonyl}[1-(trideuteriomethyl)-1H-pyrazol-4-yl]amino)phenyl disodium phosphate Step A: 5-(5-Chloro-2-{[(3S)-3-(morpholin-4-ylmethyl)-3,4-dihydroisoquinolin-2(1H)-yl]carbonyl}phenyl)-N-(4-hydroxyphenyl)-1,2-dimethyl-N-[1-(trideuteriomethyl)-1H-pyrazol-4-yl]-1H-pyrrole-3-carboxamide hydrochloride The procedure is in accordance with a protocol analogous to that described in Steps A-D of Example 1 replacing, on the one hand, the compound of Preparation 1 used in Step A by the compound of Preparation 4 and, on the other hand, the compound of Preparation 1" used in Step C by that of Preparation 6". The product obtained is finally subjected to a step of conversion into salt form in the presence of 1M HCl in ether. After filtration and lyophilisation in a mixture of acetonitrile/water, the expected compound is obtained.
Elemental Microanalysis: (%, Theoretical:Measured)
  % C=63.51:63.41; % H=5.63:5.42; % N=11.69:11.61; % Cl$^−$=4.93:4.85
High-Resolution Mass Spectrometry (ESI+−/FIA/HR, ESI−/FIA):
  Empirical formula: C$_{38}$H$_{36}$ClD$_3$N$_6$O$_4$
  [M+H]$^+$ calculated: 682.2982
  [M+H]$^+$ measured: 682.2986

Step B: 4-({[5-(5-Chloro-2-{[(3S)-3-(morpholin-4-ylmethyl)-3,4-dihydroisoquinolin-2(1H)-yl]carbonyl}phenyl)-1,2-dimethyl-1H-pyrrol-3-yl]carbonyl}[1-(trideuteriomethyl)-1H-pyrazol-4-yl]amino)phenyl disodium phosphate The procedure is in accordance with a protocol analogous to that described in Steps B and C of Example 16.
$^{31}$P NMR (500 MHz, D$_2$O) δ ppm: 4.8
IR (cm$^{-1}$): ν: C=O: 1626; ν: (phosphate; ether): 1243, 1141, 1115, 982; γ: >CH Ar:880, 831
High-Resolution Mass Spectrometry (ESI/FIA/HR and MS/MS):
  Empirical formula: C$_{38}$H$_{35}$ClD$_3$N$_6$Na$_2$O$_7$P
  [M+H]$^+$ calculated: 806.2285
  [M+H]$^+$ measured: 806.2280

EXAMPLE 20

4-[{[5-(5-Chloro-2-{[(3S)-3-(morpholin-4-ylmethyl)-3,4-dihydroisoquinolin-2(1H)-yl]carbonyl}phenyl)-1,2-dimethyl-1H-pyrrol-3-yl]carbonyl}(5-cyano-1,2-dimethyl-1H-pyrrol-3-yl)amino]phenyl disodium phosphate Step A: 5-(5-Chloro-2-{[(3S)-3-(morpholin-4-ylmethyl)-3,4-dihydroisoquinolin-2(1H)-yl]carbonyl}phenyl)-N-(5-cyano-1,2-dimethyl-1H-pyrrol-3-yl)-N-(4-hydroxyphenyl)-1,2-dimethyl-1H-pyrrole-3-carboxamide hydrochloride The procedure is in accordance with a protocol analogous to that described in Steps A-D of Example 1 replacing, on the one hand, the compound of Preparation 1 used in Step A by the compound of Preparation 4 and, on the other hand, the compound of Preparation 1" used in Step C by that of Preparation 7". The product obtained is finally subjected to a step of conversion into salt form in the presence of 1M HCl in ether. After filtration and lyophilisation in a mixture of acetonitrile/water, the expected compound is obtained.
$^1$H NMR (500 MHz, dmso-d6) δ ppm: 11.2 (bs, 1H), 9.39 (bs, 1H), 7.83 (d, 1 H), 7.54 (d, 1 H), 7.33 (s, 1 H), 7.14 (m, 2 H), 7 (m, 2 H), 6.8 (d, 2 H), 6.62 (d, 2 H), 6.57 (bs, 1 H), 5.26 (s, 1 H), 5.26 (m, 1 H), 4.64/4.03 (AB, 2 H), 4.01/3.92 (2m, 4 H), 3.75/3.43/3.15/3.02 (4m, 4 H), 3.59 (s, 3 H), 3.3/3.15 (2m, 2 H), 2.97 (s, 3 H), 2.69/2.52 (dd+d, 2 H), 2.06 (s, 3 H), 1.91 (s, 3 H)
Elemental Microanalysis: (%, Theoretical:Measured)
  % C=65.34:65.50; % H=5.62:5.15; % N=11.15:10.84% Cl−=4.70:4.44
High-Resolution Mass Spectrometry (ESI+):
  Empirical formula: C$_{41}$H$_{41}$ClN$_6$O$_4$
  [M+H]$^+$ calculated: 717.2952
  [M+H]$^+$ measured: 717.2951

Step B: 4-[{[5-(5-Chloro-2-{[(3S)-3-(morpholin-4-ylmethyl)-3,4-dihydroisoquinolin-2(1H)-yl]carbonyl}phenyl)-1,2-dimethyl-1H-pyrrol-3-yl]carbonyl}(5-cyano-1,2-dimethyl-1H-pyrrol-3-yl)amino]phenyl disodium phosphate The procedure is in accordance with a protocol analogous to that described in Steps B and C of Example 16.
$^{31}$P NMR (500 MHz, dmso-d6) δ ppm: 3.7
IR (cm$^{-1}$): ν: —CN: 2210 cm$^{-1}$; ν: C=O: 1623; ν: (phosphate; ether): 1227, 1133, 1110, 982; γ: >CH Ar: 884-741
Elemental Microanalysis:

|  | % C | % H | % N |
|---|---|---|---|
| Calculated | 58.54 | 4.79 | 9.99 |
| Found | 58.75 | 4.71 | 10.18 |

High-Resolution Mass Spectrometry (ESI+−/FIA/HR):
Empirical formula: $C_{41}H_{40}ClN_6Na_2O_7P$
[M−2Na+H]$^+$ calculated: 797.2614
[M−2Na+H]$^+$ measured: 797.2618

EXAMPLE 21

4-[{[5-(5-Chloro-2-{[(3S)-3-(morpholin-4-ylmethyl)-3,4-dihydroisoquinolin-2(1H)-yl]carbonyl}phenyl)-1,2-dimethyl-1H-pyrrol-3-yl]carbonyl}(5-cyano-1-methyl-1H-pyrrol-3-yl)amino]phenyl disodium phosphate Step A: 5-(5-Chloro-2-{[(3S)-3-(morpholin-4-ylmethyl)-3,4-dihydroisoquinolin-2(1H)-yl]carbonyl}phenyl)-N-(5-cyano-1-methyl-1H-pyrrol-3-yl)-N-(4-hydroxyphenyl)-1,2-dimethyl-1H-pyrrole-3-carboxamide hydrochloride The procedure is in accordance with a protocol analogous to that described in Steps A-D of Example 1 replacing, on the one hand, the compound of Preparation 1 used in Step A by the compound of Preparation 4 and, on the other hand, the compound of Preparation 1" used in Step C by that of Preparation 8". The product obtained is finally subjected to a step of conversion into salt form in the presence of 1M HCl in ether. After filtration and lyophilisation in a mixture of acetonitrile/water, the expected compound is obtained.
Elemental Microanalysis: (%, Theoretical:Measured)
% C=64.95:65.09; % H=5.45:5.20; % N=11.36:11.26; % Cl−=4.79:4.62
High-Resolution Mass Spectrometry (ESI/+):
Empirical formula: $C_{40}H_{39}Cl_1N_6O_4$
[M+H]$^+$ calculated: 703.2794
[M+H]$^+$ measured: 703.2789

Step B: 4-[{[5-(5-Chloro-2-{[(3S)-3-(morpholin-4-ylmethyl)-3,4-dihydroisoquinolin-2(1H)-yl]carbonyl}phenyl)-1,2-dimethyl-1H-pyrrol-3-yl]carbonyl}(5-cyano-1-methyl-1H-pyrrol-3-yl)amino]phenyl disodium phosphate The procedure is in accordance with a protocol analogous to that described in Steps B and C of Example 16.
$^{31}$P NMR (500 MHz, dmso-d6) δ ppm: 4.5
IR (cm$^{-1}$): ν: —CN: 2215 cm$^{-1}$; ν: C=O 1626; ν: (Phosphate; ether): 1227, 1141, 1112, 982; γ>CH Ar: 826-742
High-Resolution Mass Spectrometry (ESI+−/FIA/HR):
Empirical formula: $C_{40}H_{38}ClN_6Na_2O_7P$
[M−2Na+3H]$^+$ calculated: 783.2457
[M−2Na+3H]$^+$ measured: 783.2462

EXAMPLE 22

4-[{[3-(6-{[(3R)-3-(Morpholin-4-ylmethyl)-3,4-dihydroisoquinolin-2(1H)-yl]carbonyl}-1,3-benzodioxol-5-yl)-5,6,7,8-tetrahydroindolizin-1-yl]carbonyl}(phenyl)amino]phenyl disodium phosphate Step A: N-(4-Hydroxyphenyl)-3-{6-[((3R)-3-(4-morpholinylmethyl)-3,4-dihydro-2(1H)-isoquinolinyl)carbonyl]-1,3-benzodioxol-5-yl}-N-phenyl-5,6,7,8-tetrahydro-1-indolizine carboxamide hydrochloride The procedure is in accordance with a protocol analogous to that described in Steps A-D of Example 1 replacing the compound of Preparation 1' used in Step A by the compound of Preparation 4'. The solid is then dissolved in dichloromethane, and 2 mL of 1M HCl in ether are added. The batch is stirred for 1 hour and then evaporated to dryness. The hydrochloride thereby obtained is dissolved in a mixture of water/acetonitrile until dissolution is complete, and then lyophilised.
Elemental Microanalysis:

|  | % C | % H | % N | % Cl$^-$ |
|---|---|---|---|---|
| Calculated | 69.11 | 5.80 | 7.50 | 4.74 |
| Found | 68.89 | 5.23 | 7.41 | 4.62 |

Optical rotation: $(α)_D^{20}$=−45.10 (c=9 mg/mL, MeOH)

Step B: 4-[{[3-(6-{[(3R)-3-(Morpholin-4-ylmethyl)-3,4-dihydroisoquinolin-2(1H)-yl]carbonyl}-1,3-benzodioxol-5-yl)-5,6,7,8-tetrahydroindolizin-1-yl]carbonyl}(phenyl)-amino]phenyl disodium phosphate The procedure is in accordance with a protocol analogous to that described in Steps B and C of Example 16. $^{31}$P NMR (400/500 MHz, dmso-d6) δ ppm: 2.6
Elemental Microanalysis:

|  | % C | % H | % N |
|---|---|---|---|
| Calculated | 61.87 | 4.95 | 6.71 |
| Found | 61.33 | 4.93 | 7.14 |

High-Resolution Mass Spectrometry (ESI+−/FIA/HR):
Empirical formula: $C_{43}H_{41}N_4Na_2O_9P$
[M−2Na+H]$^+$ calculated: 791.2840
[M−2Na+H]$^+$ measured: 791.2845

EXAMPLE 23

4-[(1-Methyl-2,3-dihydro-1H-pyrrolo[2,3-b]pyridin-5-yl){[3-(2-{[(3S)-3-(morpholin-4-ylmethyl)-3,4-dihydroisoquinolin-2(1H)-yl]carbonyl}-4-[2-oxo-2-(piperidin-1-yl)ethoxy]phenyl)-5,6,7,8-tetrahydroindolizin-1-yl]carbonyl}amino]-phenyl disodium phosphate Step A: Methyl 3-[4-benzyloxy-2-[(3S)-3-(morpholinomethyl)-3,4-dihydro-1H-isoquinoline-2-carbonyl]phenyl]-5,6,7,8-tetrahydroindolizine-1-carboxylate To a solution of 14.19 g (35.0 mmol) of the compound obtained in Preparation 9 in 200 mL of dimethylformamide there are successively added 4-[[(3S)-1,2,3,4-tetrahydroisoquinolin-3-yl]methyl]morpholine (Preparation 1'; 8.13 g; 35.0 mmol), hydroxybenzotriazole (6.15 g; 45.5 mmol), 1-ethyl-3-(3'-dimethylaminopropyl)-carbodiimide hydrochloride (6.70 g; 45.5 mmol) and triethylamine (21.95 mL; 0.16 mol). The batch is then stirred overnight at ambient temperature. The reaction mixture is then poured into 400 mL of ethyl acetate and then successively washed with saturated aqueous NaHCO$_3$ solution, water and brine. The combined aqueous phases are extracted with ethyl acetate. The resulting organic phases are dried over sodium sulphate, filtered and concentrated under reduced pressure. The product obtained is purified by chromatography over silica gel to provide the title compound.

$^1$H NMR (500 MHz, dmso-d6, 300K) δ ppm: 7.5-7.3 (m, 5 H), 7.38 (d, 1 H), 7.2-6.9 (m, 4 H), 7.15 (dd, 1 H), 6.9 (d, 1 H), 6.35/6.25/6.08 (3*s, 1 H), 5.21/5.12 (3*s, 2 H), 5.09/4.85/3.7 (3*m, 1 H), 4.9-3.8 (8*d, 2 H), 4.2-3.4 (m, 2 H), 3.65/3.6/3.55 (3*s, 3 H), 3.6-3.4 (m, 4 H), 3-2.4 (m, 2 H), 2.9-1.8 (6*dd, 2 H), 2.5-1.95 (4*m, 4 H), 2.35-1.7 (6*m, 2 H), 2-1.45 (6*m, 4 H)

Step B: 3-[4-Benzyloxy-2-[(3S)-3-(morpholinomethyl)-3,4-dihydro-1H-isoquinoline-2-carbonyl]phenyl]-5,6,7,8-tetrahydroindolizine-1-carboxylic acid 40.1 mL of 1M aqueous LiOH solution are added to a solution of 12.7 g (20 mmol) of the compound obtained in the Step above in 40 mL of dioxane. The batch is heated at 100° C. overnight. The reaction mixture is poured into water and then extracted with ethyl ether. The ethereal phase is extracted once more with water. The combined aqueous phases are acidified to pH 4 by adding powdered citric acid, and then extracted with dichloromethane. The dichloromethane phase is washed with brine, dried over sodium sulphate, filtered and concentrated to dryness. The title product is obtained in the form of a meringue.

$^1$H NMR (500 MHz, dmso-d6, 300K) δ ppm: 11.35 (bs, 1 H), 7.5-7.3 (m, 5 H), 7.38 (m, 1 H), 7.2-6.9 (m, 4 H), 7.15 (m, 1 H), 6.9 (m, 1 H), 6.31/6.25/6.1 (3*s, 1 H), 5.22/5.2/5.15 (3*s, 2 H), 5.1/4.82/3.7 (3*m, 1 H), 4.85-3.8 (8*d, 2 H), 4.2-3.4 (m, 2 H), 3.6-3.45 (m, 4 H), 3-2.3 (m, 2 H), 2.9-1.8 (m, 2 H), 2.5-1.9 (6*m, 4 H), 2.35-1.8 (6*m, 2 H), 1.9-1.3 (m, 4 H)

Step C: 3-[4-Benzyloxy-2-[(3S)-3-(morpholinomethyl)-3,4-dihydro-1H-isoquinoline-2-carbonyl]phenyl]-N-[4-[tert-butyl(dimethyl)silyl]oxyphenyl]-N-(1-methylpyrrolo[2,3-b]-pyridin-5-yl)-5,6,7,8-tetrahydroindolizine-1-carboxamide The acid obtained in Step B (9 g, 11.8 mmol) is dissolved in 90 mL of 1,2-dichloroethane. 1.9 mL of 1-chloro-N,N,2-trimethylpropenylamine (14 mmol) are added thereto. After stirring for 3 hours at ambient temperature, 90 mL of toluene and 4.62 g of N-[4-[tert-butyl(dimethyl)silyl]oxyphenyl]-1-methyl-1H-pyrrolo[2,3-b]pyridin-5-amine (Preparation 3", 13 mmol) are added. The reaction mixture is heated at 110° C. for 20 hours. After returning to ambient temperature, the reaction mixture is washed with brine, dried over Na$_2$SO$_4$, filtered and concentrated to dryness. The residue obtained is purified by chromatography over silica gel (dichloromethane/ethanol gradient) to yield the expected product.

$^1$H NMR (500 MHz, dmso-d6, 300K) δ ppm: 7.95/7.8/7.75 (3*d, 1 H), 7.68/7.65/7.4 (3*d, 1 H), 7.4/7.3 (2*d, 1 H), 7.25-6.8 (m, 9 H), 7.05/6.9 (2*m, 1 H), 7-6.6 (3*bd, 2 H), 6.9 (m, 1 H), 6.75-6.45 (3*bd, 2 H), 6.7 (m, 1 H), 6.3 (2*d, 1 H), 5.15-4.95 (m, 2 H), 5.15/5.1/4.8 (3*s, 1 H), 4.95/4.6/3.5 (3*m, 1 H), 4.9-3.7 (8*d, 2 H), 3.8-3.3 (3*m, 2 H), 3.75/3.7/3.5 (3*s, 3 H), 3.45/3.3 (2*m, 4 H), 3-2.5 (3*m, 2 H), 3-2.3 (m, 2 H), 2.4-1.75 (5*m, 4 H), 2.25-1.7 (6*m, 2 H), 1.75-1.3 (m, 4 H), 0.7 (bs, 9 H), 0.1 (m, 6 H)

Step D: N-[4-[tert-Butyl(dimethyl)silyl]oxyphenyl]-3-[4-hydroxy-2-[(3S)-3-(morpholino-methyl)-3,4-dihydro-1H-isoquinoline-2-carbonyl]phenyl]-N-(1-methylpyrrolo[2,3-b]-pyridin-5-yl)-5,6,7,8-tetrahydroindolizine-1-carboxamide 0.9 g of Pd/C 10% is added to a solution, in 100 mL of ethanol, of 8.88 g (8.4 mmol) of the compound obtained in Step C, whilst bubbling through argon. The reaction mixture is placed under 1.2 bars of hydrogen at ambient temperature for 15 hours. The catalyst is filtered off and the solvent is evaporated off under reduced pressure to provide the title compound.

$^1$H NMR (500 MHz, dmso-d6, 300K) δ ppm: 8.06/7.92/7.87 (3*d, 1 H), 7.75/7.5/7.39 (3*d, 1 H), 7.5 (m, 1 H), 7.28-6.9 (m, 5 H), 6.87/6.7 (2*m, 2 H), 6.76 (m, 1 H), 6.75/6.67/6.62 (3*m, 2 H), 6.67/6.46 (m, 1 H), 6.4/6.36 (2*m, 1 H), 5.19/5.13/4.9 (3*bs, 1 H), 5.06/4.7/3.6 (3*m, 1 H), 4.97/4.2/4.15/4.07 (4*m, 2 H), 4.87/4.81 (bs, 1 H), 3.86/3.56/3.39 (3*m, 2 H), 3.78/3.57 (2*m, 3 H), 3.59/3.44 (2*m, 4 H), 2.96-2.61 (2*m, 2 H), 2.88/2.6 (2*m, 2 H), 2.59-1.81 (m, 6 H), 1.87-1.42 (m, 4 H), 0.89 (s, 9 H), 0.12 (m, 6 H)

Step E: N-[4-[tert-Butyl(dimethyl)silyl]oxyphenyl]-N-(1-methylpyrrolo[2,3-b]pyridin-5-yl)-3-[2-[(3S)-3-(morpholinomethyl)-3,4-dihydro-1H-isoquinoline-2-carbonyl]-4-[2-oxo-2-(1-piperidyl)ethoxy]phenyl]-5,6,7,8-tetrahydroindolizine-1-carboxamide The compound of Step D (3.0 g, 2.9 mmol) is dissolved in 100 mL of toluene. 1.53 g (5.8 mmol) of triphenylphosphine and 0.62 g (4.3 mmol) of 2-hydroxy-1-(1-piperidyl)ethanone are added thereto. The mixture is heated to 50° C., and then 1.01 g (4.3 mmol) of di-tert-butyl azodicarboxylate are added. The reaction mixture is stirred at 50° C. for 1 hour and is then allowed to return to ambient temperature before adding 1 mL of trifluoroacetic acid. After stirring overnight at ambient temperature, the mixture is successively washed with water, saturated NaHCO$_3$ and brine solution. The combined aqueous phases are extracted with ethyl acetate. The resulting organic phases are dried over sodium sulphate, filtered and concentrated under reduced pressure. The crude product obtained is purified by chromatography over silica gel (dichloromethane/ethanol 98/2) to yield the expected compound.

$^1$H NMR (500 MHz, dmso-d6, 300K) δ ppm: 8.06/7.92/7.87 (3*d, 1 H), 7.75/7.51/7.4 (3*d, 1 H), 7.49 (2*d, 1 H), 7.29-6.89 (m, 5 H), 6.93 (m, 1 H), 6.88/6.7 (m, 2 H), 6.75/6.67 (m, 1 H), 6.75/6.68/6.59 (3*m, 2 H), 6.4/6.36 (2*m, 1 H), 5.2/5.16/4.92 (3*m, 1 H), 5.06/4.69/3.58 (3*m, 1 H), 4.97/4.25/4.16/4.03 (4*d, 2 H), 4.89/4.81 (2*m, 2 H), 3.79/3.59 (2*m, 3 H), 3.59/3.43/3.4 (3*m, 6 H), 3.58/3.43 (2*m, 4 H), 3.03-2.61 (m, 2 H), 2.97-2.65 (m, 2 H), 2.57-1.74 (m, 6 H), 1.89-1.3 (m, 10 H), 0.89 (2bs, 9 H), 0.11 (m, 6 H)

Step F: N-(4-Hydroxyphenyl)-N-(1-methylpyrrolo[2,3-b]pyridin-5-yl)-3-[2-[(3S)-3-(morpholinomethyl)-3,4-dihydro-1H-isoquinoline-2-carbonyl]-4-[2-oxo-2-(1-piperidyl)ethoxy]phenyl]-5,6,7,8-tetrahydroindolizine-1-carboxamide A 1M solution of tetrabutylammonium fluoride (3.14 mL, 3 mmol) in tetrahydrofuran is added at ambient temperature to a solution, in 30 mL of tetrahydrofuran, of the compound obtained in Step E (2.92 g, 2.9 mmol). After stirring for 5 minutes, the reaction mixture is poured into a 50/50 mixture of ethyl acetate and saturated aqueous NaHCO$_3$ solution. The separated organic phase is washed with water and then with brine. The combined aqueous phases are extracted with ethyl acetate. The resulting organic phases are dried over sodium sulphate, filtered and concentrated under reduced pressure. The crude product obtained is purified by chromatography over silica gel (dichloromethane/ethanol/ammonia gradient) to yield the title compound.

$^1$H NMR (500 MHz, dmso-d6, 300K) δ ppm: 9.4 (m, OH), 8.1-7.8 (3*d, 1 H), 7.7-7.3 (2*m, 1 H), 7.5/7.4 (2*m, 1 H), 7.3-6.9 (m, 4 H), 7.2 (m, 1 H), 6.9 (m, 1 H), 6.8-6.5 (m, 2 H), 6.7-6.5 (m, 2 H), 6.7 (m, 1 H), 6.4 (m, 1 H), 5.3-5 (m, 1 H), 5.1/4.7/3.6 (3*m, 1 H), 5-3.6 (m, 2 H), 5-3.6 (m, 2 H), 4.8 (m, 2 H), 3.8-3.6 (m, 3 H), 3.6/3.4 (m, 2 H), 3.4 (m, 6 H), 3.1-2.5 (m, 2 H), 2.9-1.9 (m, 2 H), 2.5-1.7 (m, 4 H), 1.8-1.4 (m, 6 H), 1.6-1.3 (m, 4 H)

Step G: N-(4-Hydroxyphenyl)-N-(1-methyl-2,3-di-hydropyrrolo[2,3-b]pyridin-5-yl)-3-[2-[(3S)-3-(mor-pholinomethyl)-3,4-dihydro-1H-isoquinoline-2-car-bonyl]-4-[2-oxo-2-(1-piperidyl)ethoxy]phenyl]-5,6,7,8-tetrahydroindolizine-1-carboxamide 0.71 g (11 mmol) of sodium cyanoborohydride is added to a solution, in 20 mL of acetic acid, of the compound obtained in Step F (2.0 g, 2.2 mmol). After stirring for 14 hours at ambient temperature, 0.36 g (5.5 mmol) of sodium cyanoborohydride is again added, and then the reaction mixture is heated at 50° C. for 3 hours before a second addition of 0.1 eq. of sodium cyanoborohydride to complete the reaction in 30 minutes at 50° C. The acetic acid is evaporated off under reduced pressure, and then the residue is taken up in dichloromethane and washed with saturated aqueous NaHCO$_3$ solution, water and brine. The combined aqueous phases are extracted with dichloromethane. The resulting organic phases are dried over sodium sulphate, filtered and concentrated under reduced pressure. The crude product obtained is purified by chromatography over silica gel (dichloromethane/ethanol/ammonia gradient) to yield the title compound in the form of a meringue.

$^1$H NMR (500 MHz, dmso-d6, 300K) δ ppm: 9.3 (bs, 1 H), 7.5/7.4/7.3 (3*m, 1 H), 7.2/6.7 (2*m, 1 H), 7.2 (m, 1 H), 7.1-6.8 (m, 4 H), 6.9/6.7 (m, 1 H), 6.9 (m, 1 H), 6.8-6.5 (m, 2 H), 6.7-6.5 (m, 2 H), 5.3-5.1 (2*d, 1 H), 5.1/4.7/3.6 (3*m, 1 H), 4.9/4.2-3.5 (2*m, 1 H), 4.9/4.2-3.5 (2*, 1 H), 4.9-4.8 (m, 2 H), 3.6/3.4 (2*m, 4 H), 3.4/3.3 (m, 2 H), 3.4 (m, 6 H), 3.1-2.5 (m, 4 H), 3-2.4 (m, 2 H), 2.8/2.6 (m, 3H), 2.6-1.7 (m, 6 H), 1.9-1.3 (m, 10 H)

Step H: N-(4-Hydroxyphenyl)-N-(1-methyl-2,3-di-hydropyrrolo[2,3-b]pyridin-5-yl)-3-[2-[(3S)-3-(mor-pholinomethyl)-3,4-dihydro-1H-isoquinoline-2-car-bonyl]-4-[2-oxo-2-(1-piperidyl)ethoxy]phenyl]-5,6,7,8-tetrahydroindolizine-1-carboxamide hydrochloride The base obtained in Step G (0.60 g, 0.69 mmol) is dissolved in acetonitrile and then converted into salt form using 0.7 mL (0.7 mmol) of 1N HCl solution. The solution is filtered, frozen and then lyophilised to provide the title compound in the form of a powder.

Elemental Microanalysis: (%, Theoretical:Measured)
% C=68.02:68.06; % H=6.49:6.21; % N=10.89:10.87; % Cl=4.14:3.94

High-Resolution Mass Spectrometry (ESI+):
Empirical formula: C$_{51}$H$_{57}$N$_7$O$_6$
[M+H]$^+$ calculated: 864.4445
[M+H]$^+$ measured: 864.4443

Step I: 4-[(1-Methyl-2,3-dihydro-1H-pyrrolo[2,3-b]pyridin-5-yl){[3-(2-{[(3S)-3-(morpholin-4-ylmethyl)-3,4-dihydroisoquinolin-2(1H)-yl]carbonyl}-4-[2-oxo-2-(piperidin-1-yl)ethoxy]phenyl)-5,6,7,8-tetrahydroindolizin-1-yl]carbonyl}amino]phenyl disodium phosphate The procedure is in accordance with a protocol analogous to that described in Steps B and C of Example 16.

IR (cm$^{-1}$): ν: C=O: 1625; ν: (phosphate; ether): 1229, 1138, 1115, 982; γ: >CH Ar: 880-748-745

Elemental Microanalysis:

|  | % C | % H | % N |
|---|---|---|---|
| Calculated | 62.00 | 5.71 | 9.92 |
| Found | 61.45 | 5.53 | 9.96 |

High-Resolution Mass Spectrometry (ESI+):
Empirical formula: C$_{51}$H$_{56}$N$_7$Na$_2$O$_9$P
[M−2Na+3H]$^+$ calculated: 944.4106
[M−2Na+3H]$^+$ measured: 944.4116

EXAMPLE 24

4-[{[5-(5-Chloro-2-{[(3S)-3-(morpholin-4-ylmethyl)-3,4-dihydroisoquinolin-2(1H)-yl]carbonyl}phenyl)-1,2-dimethyl-1H-pyrrol-3-yl]carbonyl}(1-methyl-1H-pyrazol-4-yl)amino]phenyl disodium phosphate Step A: 5-(5-Chloro-2-{[(3S)-3-(morpholin-4-ylmethyl)-3,4-dihydroisoquinolin-2(1H)-yl]carbonyl}phenyl)-N-(4-hydroxyphenyl)-1,2-dimethyl-N-(1-methyl-1H-pyrazol-4-yl)-1H-pyrrole-3-carboxamide hydrochloride The procedure is in accordance with a protocol analogous to that described in Steps A-D of Example 1 replacing, on the one hand, the compound of Preparation 1 used in Step A by the compound of Preparation 4 and, on the other hand, the compound of Preparation 1" used in Step C by that of Preparation 5". The product obtained is finally subjected to a step of conversion into salt form in the presence of HCl in ether. After filtration and lyophilisation in a mixture of acetonitrile/water, the expected compound is obtained.

Elemental Microanalysis: (%, Theoretical:Measured)
% C=63.77:62.83; % H=5.63:5.83; % N=11.74:11.29; % Cl−=4.95:5.42

Step B: 4-[{[5-(5-Chloro-2-{[(3S)-3-(morpholin-4-ylmethyl)-3,4-dihydroisoquinolin-2(1H)-yl]carbonyl}phenyl)-1,2-dimethyl-1H-pyrrol-3-yl]carbonyl}(1-methyl-1H-pyrazol-4-yl)amino]phenyl disodium phosphate The procedure is in accordance with a protocol analogous to that described in Steps B and C of Example 16.

IR (cm$^{-1}$): ν: C=O: 1625; ν: (phosphate; ether): 1241, 1146, 1112, 983

Elemental Microanalysis:

|  | % C | % H | % N |
|---|---|---|---|
| Calculated | 56.83 | 4.77 | 10.46 |
| Found | 56.82 | 4.58 | 10.43 |

High-Resolution Mass Spectrometry (ESI+):
Empirical formula: $C_{38}H_{38}ClN_6Na_2O_7P$
$[M-2Na+3H]^+$ calculated: 759.2457
$[M-2Na+3H]^+$ measured: 759.2465

EXAMPLE 25

4-[(5-Cyano-1,2-dimethyl-1H-pyrrol-3-yl){[5-(5-fluoro-2-{[(3S)-3-(morpholin-4-ylmethyl)-3,4-dihydroisoquinolin-2(1H)-yl]carbonyl}phenyl)-1,2-dimethyl-1H-pyrrol-3-yl]carbonyl}amino]phenyl disodium phosphate Step A: N-(5-Cyano-1,2-dimethyl-1H-pyrrol-3-yl)-5-(5-fluoro-2-{[(3S)-3-(morpholin-4-ylmethyl)-3,4-dihydroisoquinolin-2(1H)-yl]carbonyl}phenyl)-N-(4-hydroxyphenyl)-1,2-dimethyl-1H-pyrrole-3-carboxamide hydrochloride The procedure is in accordance with a protocol analogous to that described in Steps A-D of Example 1 replacing, on the one hand, the compound of Preparation 1 used in Step A by the compound of Preparation 7 and, on the other hand, the compound of Preparation 1" used in Step C by that of Preparation 7". The product obtained is finally subjected to a step of conversion into salt form in the presence of HCl in ether. After filtration and lyophilisation in a mixture of acetonitrile/water, the expected compound is obtained.
High-Resolution Mass Spectrometry (ESI/FIA/HR and MS/MS):
Empirical formula: $C_{41}H_{41}FN_6O_4$
$[M+H]^+$ calculated: 701.3246
$[M+H]^+$ measured: 701.3282

Step B: 4-[(5-Cyano-1,2-dimethyl-1H-pyrrol-3-yl){[5-(5-fluoro-2-{[(3S)-3-(morpholin-4-ylmethyl)-3,4-dihydroisoquinolin-2(1H)-yl]carbonyl}phenyl)-1,2-dimethyl-1H-pyrrol-3-yl]carbonyl}amino]phenyl disodium phosphate The procedure is in accordance with a protocol analogous to that described in Steps B and C of Example 16.
$^{31}$P NMR (400/500 MHz, $CD_3OD$) δ ppm: −0.5
IR ($cm^{-1}$): v: —CN: 2211 $cm^{-1}$; v: C=O: 1629; v: (phosphate; ether): 1236, 1114, 984
Elemental Microanalysis:

|  | % C | % H | % N |
|---|---|---|---|
| Calculated | 59.71 | 4.89 | 10.19 |
| Found | 60.09 | 4.95 | 9.88 |

High-Resolution Mass Spectrometry (ESI+):
Empirical formula: $C_{41}H_{40}FN_6Na_2O_7P$
$[M-2Na+3H]^+$ calculated: 781.2909
$[M-2Na+3H]^+$ measured: 781.2898

Pharmacological and Pharmacokinetic Studies

For clarification purposes, and in anything which follows, compounds of formula (I') will be referred to as "drug of Example x" from which they have been derived. As for an example, N-(4-hydroxyphenyl)-3-{6-[((3S)-3-(4-morpholinylmethyl)-3,4-dihydro-2(1H)-isoquinolinyl)carbonyl]-1,3-benzodioxol-5-yl}-N-phenyl-5,6,7,8-tetrahydro-1-indolizine carboxamide will be referred to as the "drug from Example 1".

EXAMPLE A1

Induction of Caspase Activity In Vivo by Compounds of Formula (I')

The ability of the compounds of formula (I') to activate caspase 3 is evaluated in a xenograft model of RS4;11 leukaemia cells.

$1 \times 10^7$ RS4;11 cells are grafted sub-cutaneously into immunosuppressed mice (SCID strain). 25 to 30 days after the graft, the animals are treated orally with the various compounds. Sixteen hours after treatment, the tumour masses are recovered and lysed, and the caspase 3 activity is measured in the tumour lysates.

This enzymatic measurement is carried out by assaying the appearance of a fluorigenic cleavage product (DEVDase activity, Promega). It is expressed in the form of an activation factor corresponding to the ratio between the two caspase activities: the activity for the treated mice divided by the activity for the control mice.

N-(4-Hydroxyphenyl)-3-{6-[((3S)-3-(4-morpholinylmethyl)-3,4-dihydro-2(1H)-isoquinolinyl)carbonyl]-1,3-benzodioxol-5-yl}-N-phenyl-5,6,7,8-tetrahydro-1-indolizine carboxamide (also referred to as the drug from Example 1) was tested. At a dose of 100 mg/kg p.o., the in vivo caspase activation factor is 29.3.

The results obtained show that the compounds of formula (I') are capable of inducing apoptosis in RS4;11 tumour cells in vivo.

EXAMPLE A2

Quantification of the Cleaved Form of Caspase 3 In Vivo Brought About by Compounds of Formula (I')

The ability of the compounds of formula (I') to activate caspase 3 is evaluated in a xenograft model of RS4;11 leukaemia cells.

$1 \times 10^7$ RS4;11 cells are grafted sub-cutaneously into immunosuppressed mice (SCID strain). 25 to 30 days after the graft, the animals are treated orally with the various compounds. After treatment, the tumour masses are recovered and lysed, and the cleaved (activated) form of caspase 3 is quantified in the tumour lysates.

The quantification is carried out using the "Meso Scale Discovery (MSD) ELISA platform" test, which specifically assays the cleaved form of caspase 3. It is expressed in the form of an activation factor corresponding to the ratio between the quantity of cleaved caspase 3 in the treated mice divided by the quantity of cleaved caspase 3 in the control mice.

The results show that the compounds of formula (I') are capable of inducing apoptosis in RS4;11 tumour cells in vivo.

TABLE 1

Caspase activation factors (cleaved caspase 3 MSD test in the tumours of treated mice versus control mice) in vivo, after treatment by the oral route

| Compound tested | Dose (mg/kg) | Sampling time | Activation factor +/− S.E.M. |
|---|---|---|---|
| Drug from Example 13 | 12.5 | 2 hours | 24.5 +/− 7.5 |
| Drug from Example 19 | 12.5 | 2 hours | 13.5 +/− 1.2 |
| Drug from Example 20 | 12.5 | 2 hours | 52.0 +/− 8.6 |
| Drug from Example 21 | 12.5 | 2 hours | 22.6 +/− 2.4 |
| Drug from Example 24 | 25 | 2 hours | 45.7 +/− 2.0 |
| Drug from Example 25 | 12.5 | 2 hours | 38.7 +/− 10.7 |
| Drug from Example 15 | 25 | 2 hours | 29.8 +/− 4.0 |

EXAMPLE A3

Quantification of the Cleaved Form of Caspase 3 In Viva Brought about By Compounds of Formula (I)

The ability of the compounds of formula (I) to activate caspase 3 is evaluated in a xenograft model of RS4;11 leukaemia cells in accordance with the protocol given in Example A2.

TABLE 2

Caspase activation factors (cleaved caspase 3 MSD test in the tumours of treated mice versus control mice) in vivo, after treatment by the oral route

| Compound tested | Dose (mg/kg) | Sampling time | Activation factor +/− S.E.M. |
|---|---|---|---|
| Example 13 | 12.5 | 2 hours | 58.6 +/− 4.6 |
| Example 1 | 50 | 2 hours | 21.2 +/− 1.3 |
| Example 19 | 12.5 | 2 hours | 27.5 +/− 3.5 |
| Example 20 | 12.5 | 2 hours | 62.1 +/− 3.4 |
| Example 21 | 25 | 2 hours | 55.2 +/− 6.2 |
| Example 24 | 25 | 2 hours | 60.5 +/− 4.5 |
| Example 25 | 12.5 | 2 hours | 61.8 +/− 8.9 |
| Example 15 | 25 | 2 hours | 12.1 +/− 1.1 |

EXAMPLE B

Solubility of Compounds of Formula (I)

The solubility of compounds of formula (I) in water was measured and compared with that of compounds of formula (I').

More specifically, 4-[{[3-(6-{[(3S)-3-(morpholin-4-ylmethyl)-3,4-dihydroisoquinolin-2(1H)-yl]carbonyl}-1,3-benzodioxol-5-yl)-5,6,7,8-tetrahydroindolizin-1-yl]carbonyl}-(phenyl)amino]phenyl disodium phosphate (also referred to as the compound of Example 1) was tested and compared to N-(4-hydroxyphenyl)-3-{6-[((3S)-3-(4-morpholinylmethyl)-3,4-dihydro-2(1H)-isoquinolinyl)carbonyl]-1,3-benzodioxol-5-yl}-N-phenyl-5,6,7,8-tetrahydro-1-indolizine carboxamide (also referred to as the drug from Example 1).

The solubility of the compound of Example 1 in water is greater than or equal to 10 mg/mL (12.6 mM) whereas that of the associated drug is only 40 g/mL (56.2 M). The solubilities of the compounds were also measured in a medium buffered to physiological pH (cf. Table 3).

TABLE 3

Solubilities in aqueous medium (buffer solution: phosphate 0.33M, pH = 7.4) of compounds of formula (I) and the associated compounds of formula (I'), measured at four concentrations: 10 μM, 20 μM, 50 μM and 100 μM

| Compound tested | Solubility at 10 μM | Solubility at 20 μM | Solubility at 50 μM | Solubility at 100 μM |
|---|---|---|---|---|
| Example 19 | Soluble | Soluble | Soluble | Soluble |
| Drug from Example 19 | Soluble | Soluble | Soluble | Insoluble |
| Example 20 | Soluble | Soluble | Soluble | Soluble |
| Drug from Example 20 | Soluble | Insoluble | Insoluble | Insoluble |
| Example 25 | Soluble | Soluble | Soluble | Soluble |
| Drug from Example 25 | Soluble | Soluble | Insoluble | Insoluble |
| Example 1 | Soluble | Soluble | Soluble | Soluble |
| Drug from Example 1 | Insoluble | Insoluble | Insoluble | Insoluble |

The results show that the compounds of formula (I) are much more soluble than the compounds of formula (I'). Only compounds of formula (I) exhibit solubilities greater than or equal to 100 μM.

EXAMPLE C

In Vivo Conversion of Compounds of Formula (I)

The pharmacokinetic profile of the phosphate compounds of formula (I) is evaluated in a lipid formulation and in aqueous solution in female SCID mice. This is compared to the pharmacokinetic profile of compounds of formula (I') in a lipid formulation. More specifically, 4-[{[3-(6-{[(3S)-3-(morpholin-4-ylmethyl)-3,4-dihydroisoquinolin-2(1H)-yl]-carbonyl}-1,3-benzodioxol-5-yl)-5,6,7,8-tetrahydroindolizin-1-yl]carbonyl}(phenyl)-amino]phenyl disodium phosphate (also referred to as the compound of Example 1) was tested and compared to N-(4-hydroxyphenyl)-3-{6-[((3S)-3-(4-morpholinylmethyl)-3,4-dihydro-2(1H)-isoquinolinyl)carbonyl]-1,3-benzodioxol-5-yl}-N-phenyl-5,6,7,8-tetrahydro-1-indolizine carboxamide (also referred to as the drug from Example 1).

Lipid Formulation of the Compound of Example 1

The compound of Example 1 is prepared in a mixture of anhydrous ethanol/polyethylene glycol 300/water (10/40/50, v/v/v) intended for administration by the p.o. route. The study is carried out in 2 groups of SCID mice to which the compound of Example 1 is administered under the following conditions:

Group 1: 3 mg/kg p.o. (gavage, 10 mL/kg),
Group 2: 25 mg/kg p.o. (gavage, 10 mL/kg).

Blood samples are taken at the following points in time (3 samples per animal and 3 animals for each point in time): 0.25 hr, 0.5 hr, 1 hr, 2 hrs, 6 hrs and 24 hrs after oral administration.

Aqueous Formulation of the Compound of Example 1

The compound of Example 1 is also administered by the oral route in an aqueous medium to SCID mice, under the following conditions:

Group 1: 30 mg/kg p.o. dissolved in 1 mM sodium carbonate solution (gavage, 10 mL/kg),
Group 2: 100 mg/kg p.o. in water (gavage, 10 mL/kg).

Blood samples are taken at the following points in time (3 animals for each point in time and 1 sample per animal): 0.25 hr, 0.5 hr, 1 hr, 2 hrs, 4 hrs, 6 hrs and 24 hrs after oral administration.

For all formulations of the compound of Example 1, the blood thereby collected is centrifuged and the plasma is transferred to tubes containing 1M hydrochloric acid. The plasma concentrations of the phosphate compound (prodrug) and its hydroxylated homologue (drug) are determined simultaneously using a method of liquid chromatography coupled with mass spectrometric detection (TFC-LC-MS/MS). The limit of detection for both entities is 0.5 ng/mL.

Lipid Formulation of the Drug from the Compound of Example 1

The drug from Example 1 is prepared in a mixture of anhydrous ethanol/polyethylene glycol 300/water (10/40/50, v/v/v) intended for administration by the p.o. route. The study is carried out in several groups of SCID mice to which the drug from Example 1 is administered under the following conditions:

Group 1: 3 mg/kg p.o. (gavage, 10 mL/kg),
Group 2: 30 mg/kg p.o. (gavage, 10 mL/kg),
Group 3: 25 mg/kg p.o. (gavage, 10 mL/kg),
Group 4: 100 mg/kg p.o. (gavage, 10 mL/kg).

Blood samples are taken at the following points in time (3 animals for each point in time and 3 samples per animal for Groups 1-2 and 1 sample per animal for Groups 3 and 4):

p.o.: before administration and then 0.25 hr, 0.5 hr, 0.75 hr, 1 hr, 2 hrs, 4 hrs, 6 hrs, 8 hrs, 16 hrs and 24 hrs after oral administration at 3 and 30 mg/kg, p.o.: 0.5 hr, 2 hrs, 6 hrs, 16 hrs and 24 hrs after oral administration at 25 mg/kg and 0.5 hr, 1 hr, 2 hrs, 6 hrs, 16 hrs, 30 hrs and 48 hrs after oral administration at 100 mg/kg.

The plasma from the blood samples collected after administration of the lipid formulations of the drug from the compound of Example 1 are analysed by liquid chromatography coupled with mass spectrometric detection. The limit of quantification of the drug from the compound of Example 1 is less than or equal to 0.5 ng/mL.

Non-compartmental pharmacokinetic analysis is carried out on the mean values of the plasma concentrations of the compounds tested. The results are shown in Tables 4 and 5 hereinbelow.

The results show that, whatever the dose (from 3 to 100 mg/kg) and the carrier (lipid or aqueous formulation), the major part of the prodrug of formula (I) is rapidly converted in vivo into the corresponding drug of formula (I') (see Table 4). Plasma exposure of the prodrug ($C_{max}$, AUC) is low in comparison to that of the corresponding drug. The results also show that the plasma concentration of the drug so measured (after administration of the prodrug) is equivalent to or even greater than that measured after direct administration of the drug by the oral route (see Table 5).

TABLE 4

| Compound administered | Compound measured | |
|---|---|---|
| | Example 1 | Drug from Example 1 |
| Example 1, 3 mg/kg p.o. Lipid formulation | $C_{max}$ (ng/mL) = 16 $T_{max}$ (h) = 0.25 $AUC_t$ (ng · h/mL) = 5 | $C_{max}$ (ng/mL) = 342 $T_{max}$ (h) = 0.25 $AUC_t$ (ng · h/mL) = 314 |
| Example 1, 25 mg/kg p.o. Lipid formulation | $C_{max}$ (ng/mL) = 244 $T_{max}$ (h) = 0.25 $AUC_t$ (ng · h/mL) = 92 | $C_{max}$ (ng/mL) = 6204 $T_{max}$ (h) = 0.5 $AUC_t$ (ng · h/mL) = 20952 |
| Example 1, 30 mg/kg p.o. Aqueous formulation | $C_{max}$ (ng/mL) = 391 $T_{max}$ (h) = 1.0 $AUC_t$ (ng · h/mL) = 879 | $C_{max}$ (ng/mL) = 11967 $T_{max}$ (h) = 0.5 $AUC_t$ (ng · h/mL) = 49416 |

TABLE 4-continued

| Compound administered | Compound measured | |
|---|---|---|
| | Example 1 | Drug from Example 1 |
| Example 1, 100 mg/kg p.o. Aqueous formulation | $C_{max}$ (ng/mL) = 359 $T_{max}$ (h) = 2.0 $AUC_t$ (ng · h/mL) = 797 | $C_{max}$ (ng/mL) = 28066 $T_{max}$ (h) = 2.0 $AUC_t$ (ng · h/mL) = 168478 |

TABLE 5

| Compound administered | Compound measured Drug from Example 1 |
|---|---|
| Drug from Example 1, 3 mg/kg p.o. Lipid formulation | $C_{max}$ (ng/mL) = 295 $T_{max}$ (h) = 0.25 $AUC_t$ (ng · h/mL) = 225 |
| Drug from Example 1, 25 mg/kg p.o. Lipid formulation | $C_{max}$ (ng/mL) = 5070 $T_{max}$ (h) = 2.0 $AUC_t$ (ng · h/mL) = 20400 |
| Drug from Example 1, 30 mg/kg p.o. Lipid formulation | $C_{max}$ (ng/mL) = 8580 $T_{max}$ (h) = 1.0 $AUC_t$ (ng · h/mL) = 24200 |
| Drug from Example 1, 100 mg/kg p.o. Lipid formulation | $C_{max}$ (ng/mL) = 25878 $T_{max}$ (h) = 0.5 $AUC_t$ (ng · h/mL) = 148046 |

More specifically, p.o. administration of the prodrug in an aqueous carrier makes it possible to obtain plasma concentrations of the drug which are equivalent to or even greater than those obtained after direct p.o. administration of the drug in a lipid carrier. The prodrug therefore offers the benefit of ease of formulation compared to the corresponding drug, especially in an aqueous medium, which is very advantageous with a view to clinical development. Indeed, as Example D shows, the drug from Example 1 is difficult to formulate in an aqueous medium.

Aqueous Formulation of the Compounds of Examples 20 and 25

The compounds of Examples 20 and 25 are administered by the oral route in an aqueous medium to SCID mice, under the following conditions:

Group 1: 3 mg/kg p.o. in solution in 1M sodium carbonate (gavage, 10 mL/kg),
Group 2: 25 mg/kg p.o. in solution in 1M sodium carbonate (gavage, 10 mL/kg).

Blood samples are taken at the following points in time (3 animals for each point in time): 0.25 hr, 0.5 hr, 1 hr, 2 hrs, 6 hrs and 24 hrs after oral administration.

The blood thereby collected is centrifuged and the plasma is transferred to tubes containing 1M hydrochloric acid. The plasma concentrations of the phosphate compound (prodrug) and its hydroxylated homologue (drug) are determined simultaneously using a method of liquid chromatography coupled with mass spectrometric detection (TFC-LC-MS/MS). The limit of detection for both entities is 0.5 ng/mL.

Lipid Formulation of the Drug from the Compounds of Examples 20 and 25

The drugs from Examples 20 and 25 are prepared in a mixture of polyethylene glycol 300/ethanol/Phosal 50PG (30/10/60, v/v/v) intended for administration by the p.o. route to SCID mice, under the following conditions:

Group 1: 3 mg/kg p.o. (gavage, 10 mL/kg),
Group 2: 25 mg/kg p.o. (gavage, 10 mL/kg).

Blood samples are taken at the following points in time (3 animals for each point in time): 0.25 hr, 0.5 hr, 1 hr, 2 hrs, 6 hrs and 24 hrs after oral administration.

The blood thereby collected is centrifuged and the plasma is transferred to tubes containing 1M hydrochloric acid. The plasma concentrations of the drug are determined using a method of liquid chromatography coupled with mass spectrometric detection (TFC-LC-MS/MS). The limit of quantification is 0.5 ng/mL.

Non-compartmental pharmacokinetic analysis is carried out. The mean results are shown in Tables 6, 7, 8 and 9 hereinbelow.

TABLE 6

Example 20

| Compound administered | Compounds measured | |
| --- | --- | --- |
| | Example 20 | Drug from Example 20 |
| Example 20, 3 mg/kg p.o. Aqueous formulation | $C_{max}$ (ng/mL) = BLQ $T_{max}$ (h) = ND $AUC_t$ (ng · h/mL) = ND | $C_{max}$ (ng/mL) = 56 $T_{max}$ (h) = 1.0 $AUC_t$ (ng · h/mL) = 51 |
| Example 20, 25 mg/kg p.o. Aqueous formulation | $C_{max}$ (ng/mL) = 127 $T_{max}$ (h) = 0.25 $AUC_t$ (ng · h/mL) = 106 | $C_{max}$ (ng/mL) = 3701 $T_{max}$ (h) = 1.0 $AUC_t$ (ng · h/mL) = 8724 |

ND: not determined
BLQ: below the limit of quantification

TABLE 7

Example 20

| Compound administered | Compound measured Drug from Example 20 |
| --- | --- |
| Drug from Example 20, 3 mg/kg p.o. Lipid formulation | $C_{max}$ (ng/mL) = 39 $T_{max}$ (h) = 1.0 $AUC_t$ (ng · h/mL) = 55 |
| Drug from Example 20, 25 mg/kg p.o. Lipid formulation | $C_{max}$ (ng/mL) = 5524 $T_{max}$ (h) = 2.0 $AUC_t$ (ng · h/mL) = 10172 |

TABLE 8

Example 25

| Compound administered | Compounds measured | |
| --- | --- | --- |
| | Example 25 | Drug from Example 25 |
| Example 25, 3 mg/kg p.o. Aqueous formulation | $C_{max}$ (ng/mL) = 17 $T_{max}$ (h) = 1.0 $AUC_t$ (ng · h/mL) = 14 | $C_{max}$ (ng/mL) = 29 $T_{max}$ (h) = 1.0 $AUC_t$ (ng · h/mL) = 31 |
| Example 25, 25 mg/kg p.o. Aqueous formulation | $C_{max}$ (ng/mL) = 106 $T_{max}$ (h) = 1.0 $AUC_t$ (ng · h/mL) = 114 | $C_{max}$ (ng/mL) = 2232 $T_{max}$ (h) = 1.0 $AUC_t$ (ng · h/mL) = 3965 |

TABLE 9

Example 25

| Compound administered | Compound measured Drug from Example 25 |
| --- | --- |
| Drug from Example 25, 3 mg/kg p.o. Lipid formulation | $C_{max}$ (ng/mL) = 33 $T_{max}$ (h) = 1.0 $AUC_t$ (ng · h/mL) = 37 |
| Drug from Example 25, 25 mg/kg p.o. Lipid formulation | $C_{max}$ (ng/mL) = 3004 $T_{max}$ (h) = 1.0 $AUC_t$ (ng · h/mL) = 5704 |

The results show that, whatever the dose (3 or 25 mg/kg), the major part of the prodrugs of formula (I) is rapidly converted in vivo into the corresponding drugs of formula (I') (see Tables 6, 7, 8 and 9). Plasma exposures of the prodrugs ($C_{max}$, AUC) are low in comparison to exposures of the corresponding drugs. The results also show that the plasma concentrations of the drugs so measured (after administration of the prodrugs) are equivalent to those measured after direct administration of the drugs by the oral route (see Tables 7 and 9).

EXAMPLE D

In Vivo Pharmacokinetic Profile of the Compounds of Formula (I')

The pharmacokinetic profile of N-(4-hydroxyphenyl)-3-{6-[((3S)-3-(4-morpholinyl-methyl)-3,4-dihydro-2(1H)-isoquinolinyl)carbonyl]-1,3-benzodioxol-5-yl}-N-phenyl-5,6,7,8-tetrahydro-1-indolizine carboxamide (also referred to as the drug from Example 1) is also evaluated in a lipid and aqueous formulation in the Wistar rat.

The drug from Example 1 is prepared in an aqueous suspension in hydroxyethylcellulose 1% (w/v) in water and compared to a lipid formulation composed of a mixture of anhydrous ethanol/polyethylene glycol 400/Phosal 50PG (Oct. 30, 1960, v/v/v). The two formulations are administered by the oral route to male Wistar rats (3 rats per formulation) at a dose of 100 mg/kg p.o. (gavage, 10 mL/kg).

Blood samples are taken at the following points in time from each animal (3 animals/point in time): 0.25 hr, 0.5 hr, 0.75 hr, 1 hr, 2 hrs, 4 hrs, 8 hrs and 24 hrs after oral administration.

The plasma concentrations of the tested compound are determined after extraction followed by liquid chromatography coupled with mass spectrometric detection. The limit of quantification is 0.1 ng/mL. The results are presented in the Table hereinbelow:

TABLE 10

| Compound administered | Compound measured Drug from Example 1 |
| --- | --- |
| Drug from Example 1, 100 mg/kg p.o. Aqueous formulation | $C_{max}$ (ng/mL) = 816 $AUC_t$ (ng · h/mL) = 3480 |
| Drug from Example 1, 100 mg/kg p.o. Lipid formulation | $C_{max}$ (ng/mL) = 5070 $AUC_t$ (ng · h/mL) = 42900 |

The results show that the lipid formulation makes possible much better plasma exposure of the drug from Example 1 than the aqueous formulation.

EXAMPLE E

In Vitro Test on Human Caco-2 Cells

The cellular transport from A to B (Apical to Basolateral) of the phosphate compounds of formula (I) and the compounds of formula (I') (corresponding drugs) is studied in human Caco-2 cells. Each compound is deposited apically at 1 or 3 µM (in duplicate) and then incubated for 120 minutes.

Several samples are taken during the experiment;
apically: immediately after deposition (t=0) and at 120 minutes
basolaterally: at the end of the experiment (120 minutes)

The concentrations of the phosphate compound (prodrug) and/or of its hydroxylated homologue (drug) are determined by liquid chromatography coupled with mass spectrometric detection (LC-MS/MS). The limit of quantification for both entities is 2 ng/mL.

The apparent permeability ($P_{app}$) and the predicted absorbed fraction ($F_{abs}$) in humans are calculated for the prodrug, for the drug after incubation of the prodrug and for the drug after incubation of the drug (Hubatsch et al, *Nat Protoc.* 2007; 2(9), 2111-2119).

The experiment yield, which corresponds to the ratio (in percent) of the total amount of compound found at the end of the experiment versus that incubated, is also calculated.

The results have been collated in Table 11. They show that the prodrugs of the compounds of formula (I) are markedly decomposed in the course of the experiment (experiment yields of <1.5%), thereby bringing about the formation of the associated drugs in substantial amounts.

At the end, the predicted absorbed fraction in humans for the drugs formed after incubation of the prodrugs is similar to that obtained after incubation of the drugs.

TABLE 11

| Compound administered | Compounds measured | |
| --- | --- | --- |
| | Example 1 | Drug from Example 1 |
| Example 1 | $P_{app}$ ($10^{-6}$ cm/s) = 0.01<br>$F_{abs}$ (%) = ND<br>Yield (%) = 0 | $P_{app}$ ($10^{-6}$ cm/s) = 0.83<br>$F_{abs}$ (%) = 71<br>Yield (%) = 42 |
| Drug from Example 1 | | $P_{app}$ ($10^{-6}$ cm/s) = 0.65<br>$F_{abs}$ (%) = 67<br>Yield (%) = 37 |
| | Example 4 | Drug from Example 4 |
| Example 4 | $P_{app}$ ($10^{-6}$ cm/s) = 0.33<br>$F_{abs}$ (%) = ND<br>Yield (%) = 1.3 | $P_{app}$ ($10^{-6}$ cm/s) = 0.43<br>$F_{abs}$ (%) = 69<br>Yield (%) = 38 |
| Drug from Example 4 | | $P_{app}$ ($10^{-6}$ cm/s) = 0.21<br>$F_{abs}$ (%) = 46<br>Yield (%) = 20 |
| | Example 5 | Drug from Example 5 |
| Example 5 | $P_{app}$ ($10^{-6}$ cm/s) = 0.26<br>$F_{abs}$ (%) = ND<br>Yield (%) = 1.2 | $P_{app}$ ($10^{-6}$ cm/s) = 2.3<br>$F_{abs}$ (%) = 86<br>Yield (%) = 78 |
| Drug from Example 5 | | $P_{app}$ ($10^{-6}$ cm/s) = 0.7<br>$F_{abs}$ (%) = 68<br>Yield (%) = 34 |
| | Example 20 | Drug from Example 20 |
| Example 20 | $P_{app}$ ($10^{-6}$ cm/s) = 0<br>$F_{abs}$ (%) = ND<br>Yield (%) = 0.94 | $P_{app}$ ($10^{-6}$ cm/s) = 0.16<br>$F_{abs}$ (%) = 16<br>Yield (%) = 100 |
| Drug from Example 20 | | $P_{app}$ ($10^{-6}$ cm/s) = 0.29<br>$F_{abs}$ (%) = 25<br>Yield (%) = 91 |
| | Example 21 | Drug from Example 21 |
| Example 21 | $P_{app}$ ($10^{-6}$ cm/s) = 0<br>$F_{abs}$ (%) = ND<br>Yield (%) = 0.83 | $P_{app}$ ($10^{-6}$ cm/s) = 0.21<br>$F_{abs}$ (%) = 19<br>Yield (%) = 100 |
| Drug from Example 21 | | $P_{app}$ ($10^{-6}$ cm/s) = 0.27<br>$F_{abs}$ (%) = 24<br>Yield (%) = 82 |
| | Example 25 | Drug from Example 25 |
| Example 25 | $P_{app}$ ($10^{-6}$ cm/s) = 0<br>$F_{abs}$ (%) = ND<br>Yield (%) = 33 | $P_{app}$ ($10^{-6}$ cm/s) = 0.22<br>$F_{abs}$ (%) = 20<br>Yield (%) = 48 |

TABLE 11-continued

| Compound administered | Compounds measured |
| --- | --- |
| Drug from Example 25 | $P_{app}$ ($10^{-6}$ cm/s) = 0.49<br>$F_{abs}$ (%) = 40<br>Yield (%) = 100 |

ND: not determined

EXAMPLE F

Anti-Tumour Activity In Vivo

The anti-tumour activity of the compounds of the invention is evaluated in a xenograft model of RS4;11 leukaemia cells.

$1 \times 10^7$ RS4;11 cells are grafted sub-cutaneously into immunosuppressed mice (SCID strain). 25 to 30 days after the graft, when the tumour mass has reached about 150 mm³, the mice are treated orally with the various compounds in two different regimes (daily treatment for five days per week for two weeks, or two treatments per week for two weeks). The tumour mass is measured twice a week from the start of treatment.

The compounds of the invention have antitumour activity, via the oral route, in the RS4;11 leukaemia model (acute lymphoblastic leukaemia). The results obtained show that the compounds of the invention are capable of inducing significant tumour regression.

EXAMPLE G

Pharmaceutical Composition: Tablets

| 1000 tablets containing a dose of 5 mg of a compound selected from Examples 1 to 25 | 5 g |
| --- | --- |
| Wheat starch | 20 g |
| Maize starch | 20 g |
| Lactose | 30 g |
| Magnesium stearate | 2 g |
| Silica | 1 g |
| Hydroxypropylcellulose | 2 g |

The invention claimed is:
1. A phosphate compound of formula (I):

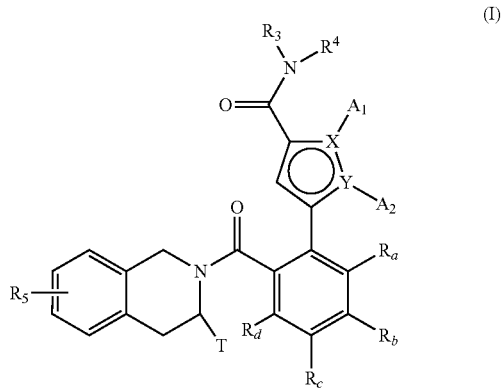

wherein:
X and Y represent a carbon atom or a nitrogen atom, wherein X and Y may not simultaneously represent two carbons atoms or two nitrogen atoms;

$A_1$ and $A_2$, together with the atoms carrying them, form an optionally substituted, aromatic or non-aromatic heterocycle Het composed of 5, 6 or 7 ring members which may have, in addition to the nitrogen represented by X or by Y, from one to 3 heteroatoms selected independently from oxygen, sulphur and nitrogen, wherein the nitrogen atom may be substituted by a hydrogen atom, a linear or branched ($C_1C_6$) alkyl group or a —C(O)—O -Alk group wherein Alk is a linear or branched ($C_1C_6$alkyl group, or $A_1$ and $A_2$ independently of one another represent a hydrogen atom, a linear or branched ($C_1$-$C_6$)polyhaloalkyl, a linear or branched ($C_1$-$C_6$)alkyl group or a cycloalkyl;

T represents a hydrogen atom, a linear or branched ($C_1$-$C_6$)alkyl group optionally substituted by from one to three halogen atoms, a ($C_1$-$C_4$)alkyl-$NR_1R_2$ group, or a ($C_1$-$C_4$)alkyl-$OR_6$ group;

$R_1$ and $R_2$ independently of one another represent a hydrogen atom or a linear or branched ($C_1C_6$)alkyl group, or $R_1$ and $R_2$ together with the nitrogen atom carrying them from a heterocycloalkyl;

$R_3$ represents a linear or branched ($C_1$-$C_6$)alkyl group, a linear or branched ($C_2$-$C_6$)alkenyl group, a linear or branched ($C_2$-$C_6$)alkynyl group, a cycloalkyl group, a ($C_3$-$C_{10}$)cycloalkyl-($C_1$-$C_6$)alkyl group wherein the alkyl moiety is linear or branched, a heterocycloalkyl group, an aryl group or a heteroaryl group, wherein one or more of the carbon atoms of the preceding groups, or of their possible substituents, may be deuterated;

$R_4$ represents an aryl group, a heteroaryl group, a cycloalkyl group or a linear or branched ($C_1$-$C_6$)alkyl group, wherein one or more of the carbon atoms of the preceding groups, or of their possible substituents, may he deuterated;

$R_5$ represents a hydrogen atom, a halogen atom, a linear or branched ($C_1C_6$)aikyl group, or a linear or branched ($C_1$-$C_6$)alkyl group:

$R_6$ represents a hydrogen atom or a linear or branched ($C_1$-$C_6$)alkenyl group;

$R_a$, $R_b$, $R_c$ and $R_d$, each independently of the others, represent, a hydrogen atom, a linear or branched ($C_1$-$C_6$)alkyl, a linear or branched ($C_2$-$C_6$)alkenyl, a linear or branched ($C_2$-$C_6$)alkynyl, an aryl, a heteroaryl, a halogen atom, a linear or branched ($C_1$-$C_6$)alkoxy group, a hydroxyl group, a linear or branched ($C_1$-$C_6$) polyhaloalkyl group, a trifluoromethoxy group, —$NR_7R_7'$, nitro, $R_7$—CO—($C_0$-$C_6$)alkyl-, $R_7$—CO—NH—($C_0$-$C_5$)alkyl-, $NR_7R_7'$—CO—($C_0$-$C_6$)alkyl-, $NR_7R_7'$—CO—($C_0$-$C_6$)alkyl-O—, $R_7$—$SO_2$—NH—($C_0$-$C_6$)alkyl-, $R_7$—NH—CO—NH—($C_0$-$C_6$)alkyl-, $R_7$—O—CO—NH—($C_0$-$C_6$)alkyl-, a heterocycloalkyl group, or the substituents of one of the pairs ($R_a$, $R_b$), ($R_b$,$R_c$) or ($R_c$,$R_d$) together with the carbon atoms carrying them form a ring composed of from 5 to 7 ring members, which ring may have from one to 2 hetero atoms selected from oxygen and sulphur, wherein one or more carbon atoms of the ring defined hereinbefore may be deuterated or substituted by from one to 3 groups selected from halogen and linear or branched ($C_1$-$C_6$)alkyl;

$R_7$ and $R_7'$ independently of one another represent a hydrogen atom, a linear or branched ($C_1$-$C_6$)alkyl, a linear or branched ($C_2$-$C_6$)alkenyl, a linear or branched ($C_2$-$C_6$)alkynyl, an aryl or a heteroaryl, or $R_7$ and $R_7'$ together with nitrogen atom carrying them form a heteroaryle composed of from 5 to 7 ring members, wherein at least one a the carbon atoms of the compound of formula (I) substituted by one of the following phosphate groups: —OPO(OM)(OM'), —OPO(OM)(O$^-$$M_1^+$), —OPO(O$^{-M}{}_1{}^+$)(O$^{-M}{}_2{}^+$), —OPO(O$^-$)(O$^-$)$M_3^{2+}$, —OPO(OM)(O[$CH_2CH_2O$]$_n$$CH_3$), or —OPO(O$^{-M}{}_1{}^{30}$)(O[$CH_2CH_2O$]$_H$$CH_3$) wherein M and M' independently of one another represent a hydrogen atom, a linear or branched ($C_1$-$C_6$)alkyl group, a linear or branched ($C_2$-$C_6$)alkenyl group, a linear or branched ($C_2$-$C_6$) alkynyl group, a cycloalkyl or a heterocycloalkyl both composed of 5 or 6 ring members, and wherein $M_1^{30}$ and $M_2^+$ independently of one another represent a pharmaceutically acceptable monovalent cation, and $M_3^{2+}$ represents a pharmaceutically acceptable divalent cation and n is an integer from 1 to 5, it being understood that:
"aryl" means a phenyl, naphthyl biphenyl or indenvl group, "hetcroaryl" means any mono- or bi-cyclic group composed of from 5 to 10 ring members, having at least one aromatic moiety and containing from 1 to 4 hetero atoms selected from oxygen, sulphur and nitrogen (including quaternary nitrogens), "cycloalkyl" means any mono- or bi-cyclic, non-aromatic, carboeyclic group containing, from 3 to 10 ring members, "heterocycloalkyr" means any mono- or bi-cyclic, non-aromatic, condensed or spiro group composed of 3 to 10 ring members and containing from 1 to 3 hetero atoms selected from oxygen, sulphur, SO, $SO_2$ and nitrogen, wherein the aryl, heteroaryl, cycloalkyl aand heterocycloalkyl groups so defined and the groups alkyl, alkenyl, alkynyl and alkoxy may be optionally substituted by from 1 to 3 groups selected from optionally substituted, linear or branched ($C_1$-$C_6$)alkyl, ($C_3$-$C_6$)spiro, linear or branched, optionally substituted ($C_1$-$C_6$)alkoxy, ($C_1$-$C_6$)alkyl-S-, hydroxy oxo (or N-oxide where appropriate), nitro, cyano, —COOR' , —OCOR' , NR'R" ,linear or branched ($C_1$-$C_6$)polyhaloalkyl, trifluoromethoxy, ($C_1$-$C_6$)alkylsulphonyl, halogen, optionally substituted aryl, heteroaryl, aryloxy, arylthio, cycloalkyl, heterocycloalkyl optionally substituted by one or more halogen atoms or alkyl groups, wherein R' and R" independently of one another represent a hydrogen atom or an optionally substituted, linear or branched ($C_1$-$C_6$)alkyl group, wherein the Het group defined in formula (I) may be optionally substituted by from one to three groups selected from linear or branched ($C_1$-$C_6$)alkyl, hydroxy, linear or branched ($C_1$-$C_6$)alkoxy. $NR_1'R_1''$ and halogen, wherein $R_1'$ and $R_1''$ independently of one another represent a hydrogen atom or an optionally substituted, linear or branched ($C_1$-$C_6$)alkyl group, or an enantiomerhr, a diastereoisomer, or an addition salt thereof with a pharmaceutically acceptable acid or base.

2. The compound according to claim 1, wherein $R_4$ represents phenyl substituted in the para position by a group of formula —OPO(OM)(OM'), —OPO(OM)(O$^-$$M_1^+$), —OPO(O$^-$$M_1^+$)(O$^-$$M_2^+$), —OPO(O$^-$)(O$^-$)$M_3^{2+}$, —OPO(OM)(O[$CH_2CH_2O$]$_n$$CH_3$), or —OPO(O$^{-M}{}_1{}^+$)(O[$CH_2CH_2O$]$_n$$CH_3$), wherein M and M' independently of one another represent a hydrogen atom, a linear or branched ($C_1$ -$C_6$)alkyl group, a linear or branched ($C_2$-$C_6$)alkenyl group, a linear or branched ($C_2$ -$C_6$)alkynyl group, a cycloalkyl or a heterocycloalkyl both composed of 5 or 6 ring members, and wherein $M_1^+$ and $M_2^+$ independently of one another represent a pharmaceutically acceptable monovalent cation, and $M_3^{2+}$ represents a pharmaceutically acceptable divalent cation and n is an integer from 1 to 5, wherein the phenyl group may optionally be substituted by one or more halogen atoms.

3. The compound according to claim 1, wherein $R_4$ represents phenyl substituted in the para position by a group of formula —OPO(O⁻Na⁺)(O⁻Na⁺).

4. The compound according to claim 1, wherein X represents a carbon atom and Y represents a nitrogen atom.

5. The compound according to claim 1, wherein the group:

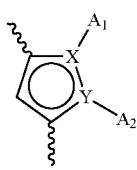

represents a 5,6,7,8-tetrahydroindolizine, an indolizine or a dimethylated pyrrole, 6. The compound according to claim 1, wherein T represents a methyl, (morpholin-4-yl)methyl or 3-(morpholin-4-yl)propyl group.

7. The compound according to claim 1, wherein $R_a$ and $R_d$ each represent a hydrogen atom and ($R_b$, $R_c$), together with the carbon atoms carrying them, form a 1,3dioxolane group or a 1,4-dioxane group; or $R_a$, $R_c$ and $R_d$ each represent a hydrogen atom and $R_b$ represents a hydrogen atom or a halogen atom.

8. The compound according to claim 1, wherein $R_a$ and $R_d$ each represent a hydrogen atom, $R_b$ represents a halogen atom and R, represents a methoxy group.

9. The compound according to claim 1, wherein $R_a$, $R_b$ and $R_d$ each represent a hydrogen atom and $R_c$ represents a $NR_7R_7'$—CO—($C_0$-$C_6$)alkyl-O-group.

10. The compound according to claim 1, wherein $R_3$ represents a group selected from phenyl, 1H-indoie, 1H-pyrrolo [2,3 -b]pyridine, pyridine, 1H-pyrazole, 1H -pyrrole and 2,3-dihydro-1H-pyrrolo[2,3b]pyridine, those groups optionally having one or more substituents selected from linear or branched ($C_1C_6$alkyl, cyano and trideuteriomethyl.

11. The compound according to claim 1, which is selected from:

4-[{[3-(6-{[(3S)-3-(morpholin-4-ylmethyl)-3,4-dihydroisoquinolin-2(1H) -yl]carbonyl}-1,3-benzodioxol-5-yl)-5,6,7,8-tetrahydroindolizin-1-yl]carbonyl}(phenyl)amino]phenyl disodium phosphate, 4-[{[5-(5-chloro-2-{[(3S)-3-(morpholin-4-ylmethyl)-3,4-dihydroisoquinolin-2(1H) -yl]carbonyl}phenyl)-1,2-dimethyl-1H-pyrrol-3-yl]carbonyl}(pyridin-4-yl) amino]phenyl disodium phosphate, 4-({[5-(5-chloro-2-{[(3S)-3-(morpholin-4-ylmethyl)-3,4-dihydroisoquinolin-2(1H) -yl]carbonyl}phenyl)-1,2-dimethyl-1H-pyrrol-3-yl]carbonyl}[1-(trideuteriomethyl) -1H-pyrazol-4-yl]amino)phenyl disodium phosphate, 4-[{[5-(5-chloro-2-{[(3S)-3-(morpholin-4-ylmethyl)-3,4-dihydroisoquinolin-2(1H) -yl]carbonyl}phenyl)-1,2-dimethyl-1H-pyrrol-3-yl]carbonyl}(5-cyano-1,2-dimethyl -1H-pyrrol-3-yl)amino]phenyl disodium phosphate, 4-[{[5-(5-chloro-2-{[(3S)-3-(morpholin-4-ylmethyl)-3,4-dihydroisoquinolin-2(1H) -yl]carbonyl}phenyl)-1,2-dimethyl-1H-pyrrol-3-yl]carbonyl}(5-cyano-1-methyl-1H -pyrrol-3-yl)amino]phenyl disodium phosphate, 4-[{[5-(5-chloro-2-{[(3S)-3-(morpholin-4-ylmethyl)-3,4-dihydroisoquinolin-2(1H) -yl]carbonyl}phenyl)-1,2-dimethyl-1H-pyrrol-3-yl]carbonyl}(5-cyano-1-methyl-1H -pyrrol-3-yl)amino]phenyl disodium phosphate, 4-[(5-cyano-1,2-dimethyl-1H-pyrrol-3-yl){[5-(5-fluoro-2-{[(3S)-3-(morpholin-4-ylmethyl)-3,4-dihydroisoquinolin-2(1H)-yl]carbonyl}phenyl)-1,2-dimethyl-1H -pyrrol-3-yl]carbonyl}amino]phenyl disodium phosphate, and 4-[{[5-(5-fluoro-2-{[(3S)-3-(morpholin-4-ylmethyl)-3,4-dihydroisoquinolin-2(1H) -yl]carbonyl}phenyl)-1,2-dimethyl-1H-pyrrol-3-yl]carbonyl}(1-methyl-1H -pyrazol-4-yl)amino]phenyl disodium phosphate, or an enantiomer, a diastereoisomer, or an addition salt thereof with a pharmaceutically acceptable acid or base.

12. A pharmaceutical composition comprising the compound according to claim 1 in combination with one or more pharmaceutically acceptable excipients.

13. A composition comprising the compound according to claim 1 in combination with an anti-cancer agent selected from genotoxic agents, mitotic poisons, anti-metabolites, proteasome inhibitors, kinase inhibitors and antibodies.

14. The composition according to claim 13 further comprising one or more pharmaceutically acceptable excipients.

15. A combination comprising the compound according to claim 1 and an anticancer agent selected from genotoxic agents, mitotic poisons, anti-metabolites, proteasome inhibitors, kinase inhibitors and antibodies.

* * * * *

UNITED STATES PATENT AND TRADEMARK OFFICE
CERTIFICATE OF CORRECTION

Page 1 of 2

PATENT NO. : 9,115,159 B2
APPLICATION NO. : 14/337577
DATED : August 25, 2015
INVENTOR(S) : Le Tiran et al.

It is certified that error appears in the above-identified patent and that said Letters Patent is hereby corrected as shown below:

Title Page, item [30], Foreign Patent Doc: "WO 2013/098080" should read -- WO 2013/096060 --.

Title Page, item [57], Formula (I) " 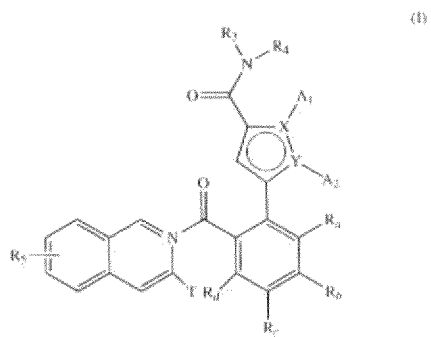 " should read -- 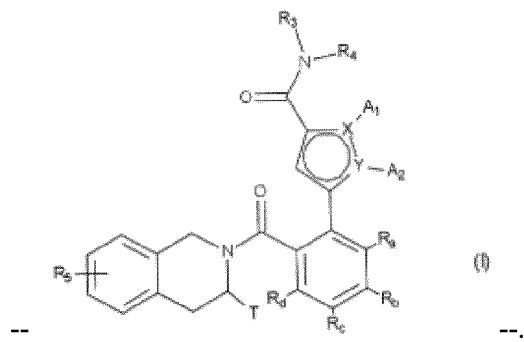 --.

In the claims

Column 53, Line 51, claim 1: "$C_5$" should read -- $C_6$ --.

Column 54, Line 5, claim 1: " -OPO($O^{-M_1^+}$)($O^{-M_2^+}$)" should read -- -OPO($O^-M_1^+$)($O^-M_2^+$) --.

Signed and Sealed this
Seventeenth Day of May, 2016

Michelle K. Lee
*Director of the United States Patent and Trademark Office*

CERTIFICATE OF CORRECTION (continued)
U.S. Pat. No. 9,115,159 B2

Column 54, Lines 8-9, claim 1: "-OPO(O$^-$M$_1^{30}$)(O[CH$_2$CH$_2$O]$_H$CH$_3$)" should read
-- -OPO(O$^-$M$_1^+$)(O[CH$_2$CH$_2$O]$_n$CH$_3$) --.

Column 54, Line 14, claim 1: "M$_1^{30}$" should read -- M$_1^+$ --.

Column 54, Line 20, claim 1: "indenvl" should read -- indenyl --.

Column 54, Line 22, claim 1: "hetcroaryl" should read -- heteroaryl --.

Column 54, Line 28, claim 1: "carboeyclic" should read -- carbocyclic --.

Column 54, Line 30, claim 1: "heterocycloalkyr" should read -- heterocycloalkyl --.

Column 54, Line 57, claim 1: "enantiomerhr" should read -- enantiomer --.